United States Patent
Anderson et al.

(10) Patent No.: US 6,660,836 B1
(45) Date of Patent: *Dec. 9, 2003

(54) METHODS FOR CARBON-CENTERED RADICAL MEDIATED HEAVY HYDROGEN LABELING OF COMPOUNDS

(75) Inventors: Vernon E. Anderson, Shaker Heights, OH (US); Michael B. Goshe, Canton, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/579,112

(22) Filed: May 25, 2000

Related U.S. Application Data

(63) Continuation-in-part of application No. 09/323,741, filed on Jun. 1, 1999.
(60) Provisional application No. 60/129,019, filed on Apr. 13, 1999.

(51) Int. Cl.[7] .................................................. C07K 1/13
(52) U.S. Cl. ........................ 530/345; 530/333; 436/86; 436/89
(58) Field of Search .............................. 530/333, 345; 436/86, 89

(56) References Cited

U.S. PATENT DOCUMENTS

| | | | | |
|---|---|---|---|---|
| 4,428,859 A | | 1/1984 | Koch et al. ............. | 252/301.17 |
| 4,767,994 A | * | 8/1988 | Hopkins et al. ............. | 324/438 |
| 4,996,062 A | * | 2/1991 | Lehtonen et al. ............... | 426/8 |
| 5,434,084 A | * | 7/1995 | Burgess, Jr. .................. | 436/52 |

OTHER PUBLICATIONS

Riesz (J Am Chem Soc 88, 872, 1966).*
Segal, Anthony W. (Annals of the New York Academy of Sciences 832 (Phagocytes: Biology, Physiology, Pathology, and Pharmacotherapeutics), 215–222, 1997).*
Michel, H. (Annual Review of Biophysics and Biomolecular Structure 27, 329–356, 1998).*
Whittaker, James W. (Pure and Applied Chemistry 70(4), 903–910, 1998).*
Martin Saunders et al., 1967, "A Method for Obtaining Three–Dimensional Structural Information about Protein Molecules in Solution," *Journal of the American Chemical Society 89: 2,* 472–473.
Alexander et al., 1955, "Physico–chemical methods of protection against ionizing radiations," In: *Radiobiology Symposium,* pp 49–55, Bacq & Alexander, Academic Press: New York.
Breen and Murphy, 1995, "Reactions of oxyl radicals with DNA," *Free Radic. Biol. Med. 18:* 1033–1077.
Buettner and Mason, 1990, "Spin–trapping methods for detecting superoxide and hydroxyl free radicals in vitro and in vivo," *Methods in Enzymology 186*:127–133.

Davies, 1987, "Protein damage and degradation by oxygen radicals. I. General aspects," *J. Biol. Chem.* 262: 9895–9901.
Davies et al., 1987, "Protein damage and degradation by oxygen radicals. II. Modification of amino acids," *J. Biol. Chem.* 262:9902–9907.
Franchet–Beuzit et al., 1993, "Radiolytic footprinting. Beta rays, gamma photons, and fast neutrons probe DNA–protein interactions," *Biochemistry* 32:2104–2110.
Fu et al., 1995, "Biological fate of amino acid, peptide and protein hydroperoxides," *Biochem. J. 311*:821–827.
Gajewski et al., 1988, "Structure of hydroxyl radical–induced DNA–protein crosslinks in calf thymus nucleohistone in vitro," *Int. J. Radiat. Biol. 54*:445–459.
Garrison, 1987, "Reaction Mechanisms in the Radiolysis of Peptides, Polypeptides, and Proteins," *Chem. Rev. 87*:381–398.
Greiner et al., 1996, "Binding of the sigma 70 protein to the core subunits of *Escherichia coli* RNA polymerase, studied by iron–EDTA protein footprinting," *Proc. Natl. Acad. Sci., U.S.A. 93*:71–75.
Hertzberg and Dervan, 1984, "Cleavage of DNA with methidiumpropyl–EDTA–iron(II): reaction conditions and product analyses," *Biochemistry 23*:3934–3945.
Heyduk and Heyduk, 1994, "Mapping protein domains involved in macromolecular interactions: a novel protein footprinting approach," *Biochemistry 33*:9643–9650.
Karam et al., 1984, "OH radical–induced products of tyrosine peptides," *Int. J. Radiat. Biol. Relat. Stud. Phys. Chem. Med. 46*:715–724.
Maleknia et al., 1999, "Electrospray–assisted modification of proteins: a radical probe of protein structure," *Rapid Communications in Mass Spectrometry 13*:2352–2358.
Rana et al., 1990, "Specific Cleavage of a Protein by an Attached Iron Chelate," *J. Am. Chem. 112*:2457–2458.
Stadtman, 1993, "Oxidation of free amino acids and amino acid residues in proteins by radiolysis and by metal–catalyzed reactions," *Annu. Rev. Biochem. 62*:797–821.
Tullius et al., 1987, "Hydroxyl radical footprinting: a high–resolution method for mapping protein–DNA contacts," *Methods of Enzymology 155*:537–558.

* cited by examiner

*Primary Examiner*—Christopher S. F. Low
*Assistant Examiner*—David Lukton
(74) *Attorney, Agent, or Firm*—Pennie & Edmonds LLP

(57) ABSTRACT

The solvent accessible reduced carbon atoms in a molecule of interest are labeled with heavy hydrogen. The carbon atoms are labeled under anaerobic, aqueous conditions by exposing the molecule of interest to a hydrogen atom abstractor in the presence of a heavy hydrogen source and a heavy hydrogen donor. If the hydrogen atom abstractor is hydroxyl radical, an electron scavenger source is provided. Optionally, an internal reference is provided to facilitate experimental reproducibility.

67 Claims, 23 Drawing Sheets

```
SEQUENCE LISTING

<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Target
      sequence for heavy hydrogen exchange reactions

<400> SEQUENCE: 1

Tyr Ala Gly Phe Leu
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Target
      sequence for heavy hydrogen exchange reactions

<400> SEQUENCE: 2

Ser Asn Glu Gln Lys Ala Cys Lys Val Leu Gly Ile
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Target
      sequence for heavy hydrogen exchange reactions

<400> SEQUENCE: 3

Arg Arg Ala Ser Leu Gly
1               5
```

METHODS FOR CARBON-CENTERED RADICAL MEDIATED HEAVY HYDROGEN LABELING OF COMPOUNDS

This application is a continuation in part of U.S. patent application Ser. No. 09/323,741 filed Jun. 1, 1999, entitled "Methods for Carbon-Centered Radical Mediated Heavy Hydrogen Labeling of Compounds" by Vernon E. Anderson and Michael B. Goshe. Application Ser. No. 09/323,741 claims priority to provisional application No. 60/129,019, filed Apr. 13, 1999.

This research was supported in part by grants GM 36562, AG 14249, and DK 07319 awarded by the National Institutes of Health. The U.S. government may have certain rights to this invention.

BACKGROUND OF THE INVENTION

1. Field of the Invention

The present invention relates to a solution based method for carbon-centered radical mediated protium/heavy hydrogen exchange into the reduced carbon atoms in a molecule of interest. The methods of the present invention can be used to determine which reduced carbon atoms in a molecule are solvent accessible. In particular, the methods of the present invention can be used to determine which carbon atoms in a macromolecule, such as a peptide or protein, are solvent accessible when the macromolecule is in a particular folded state.

2. Background Art

Carbon-centered radical mediated heavy hydrogen labeling of compounds is well known in the art. For example, radiolysis studies have demonstrated that hydroxyl (OH) radical can act as a hydrogen atom abstractor that removes a hydrogen atom from reduced carbon atoms in molecules such as amino acids, peptides, and proteins to form a carbon-centered radical. See e.g. Garrison, 1987, *Chem. Rev.* 87:381–398; von Sonntag, 1987, The Chemical Basis of Radiation Biology, Taylor & Francis: London. However, determining which carbon atoms in a molecule react with the hydroxyl radical has been elusive. In the case of DNA, reaction of DNA with a hydrogen atom abstractor results in strand scission. Thus, the site of the reaction between a hydrogen atom abstractor, such as hydroxyl radical, and the DNA can be inferred by studying DNA cleavage patterns. Hertzberg et al., *Biochemistry* 23:3934–3945.

The predominant mode of hydrogen atom abstractor initiated damage of DNA and proteins is removal of a hydrogen atom from a C—H bond of a reduced carbon atom to produce the corresponding carbon-centered radical. von Sonntag, supra. The carbon-centered radical has various chemical fates including: (1) reaction with molecular oxygen, initially forming a hydroperoxyl species that can result in hydroxylation (Fu et al., 1995, *Biochem. J.* 311:821–827) and DNA (Breen et al., 1995, *Free Radic. Biol. Med.* 18:1033–1077) or protein (Davies, *J. Biol. Chem.* 262:9895–9901) strand scission, (2) recombination of two carbon-centered radicals to form a carbon-carbon crosslink (Karam et al., 1984, *Int. J. Radiat. Biol. Relat. Stud Phys. Chem. Med.* 46:715–724; Davies et al., 1987, *J. Biol. Chem.* 262:9902–9907; Gajewski et al., *Int. J. Radiat. Biol. Relat. Stud Phys. Chem. Med.* 54:445–449); and (3) chemical repair by H atom donation, such as that mediated by sulfhydryls (Alexander et al., 1955, *Radiobiology Symposium*, pp 49–55, Bacq & Alexander, Academic Press: New York). Thus, the initial site of hydroxyl radical attack on a molecule is often obscured by the multiplicity of resulting products.

In DNA, the abstraction of any ribose hydrogen atom and subsequent oxidation leads to chain scission. Thus, carbon-centered radical mediated assays provide a general method for identifying residues that react with the hydrogen atom abstractor. The ability to randomly initiate cleavage of the DNA backbone by enzymatic or chemical means is the most essential chemical step in DNA footprinting. The sites protected by protein binding are excluded from solvent and consequently, are not susceptible to attack by the hydrogen atom abstractor. The absence of these DNA product fragments in electrophoretic separations identify the DNA nucleotides involved in protein-DNA recognition. The footprint resolution is dependent upon the chemical nature of the DNA cleaving reagent. Base resolution can be achieved by using a small, sterically unhindered molecule that is highly reactive and is nonspecific, indiscriminately cleaving at all base positions of the DNA backbone. Hydroxyl radical generated by γ-radiolysis has been experimentally shown to possess all of these attributes and has been used to identify contacts in protein-DNA complexes at base resolution. Franchet-Beuzig, et al., 1993, *Biochemistry* 32:2104–2110.

Despite the success in using carbon-centered radical mediated reactions in DNA footprinting techniques, analogous footprinting techniques to study protein-protein interactions have proven to be unsatisfactory. Small metal chelates have been used to randomly cleave polypeptide chains. The chelate, iron(II)-EDTA, has been utilized in either a tethered or untethered form. The tethered form can be used to map its proximity to neighboring peptide bonds. Rana et al., 1990, *J. Am. Chem.* 112:2457–2458. Using untethered iron(I)-EDTA as a nonspecific protein cleaving agent, Heyduk et al. have studied solvent-accessible sites induced by changes in protein conformation upon ligand binding for cAMP receptor protein in the presence and absence of cAMP. Heyduk et al., 1994, *Biochemistry* 33:9643–9550. In addition, Greiner and coworkers have used iron(II)-EDTA as a nonspecific protein cleaving agent to map the interactions between the subunits of *E. coli* RNA polymerase. Greiner et al., 1996, *Proc. Natl. Acad. Sci., U.S.A.* 93:71–75. In both cases, the peptide fragments were electrophoretically separated and visualized by immunostaining with antibodies specific to the N- and/or C-terminal peptides of the protein. The limitations of this method are (1) iron(II)-EDTA cleavage tends to occur at hypersensitive sites, (2) antibodies for the N- and/or C-termini are required for the proteins of interest, and (3) identification of the sites of protection is usually confined to segments of 10–15 residues in length. Although this protein footprinting methodology permits mapping contact regions of protein domains involved in macromolecular assemblies, the ability of the technique to specifically identify the sites involved in recognition at the amino acid residue level has not been satisfactory.

The failure to achieve single residue resolution in protein footprinting studies despite the success in analogous DNA footprinting studies can also be understood by comparing the reactivity of hydrogen atom abstractors, such as hydroxyl radical, with proteins and DNA. For duplex DNA, hydroxyl radical react with the macromolecule by abstracting a hydrogen atom from solvent-accessible C—H bonds of the deoxyribose ring along the DNA backbone, producing a carbon-centered radical that reacts with $O_2$ and results in strand scission. Breen et al., 1995, *Free Radic. Biol. Med.* 18:1033–1077. Cleavage of globular proteins occurs by a similar mechanism. Stadtman, 1993, *Annu. Rev. Biochem.* 62:797–821. Abstraction of a $C_\alpha$—H of the protein backbone by hydroxyl radical produces a carbon-centered radical that reacts with $O_2$, forming a hydroperoxyl species that leads to protein strand scission. However, the majority of solvent-accessible C—H bonds present on the protein's solvent-accessible surface are not comprised of the backbone ($C_\alpha$—$H_\alpha$) but those of the side chains. Thus, in protein footprinting the major pathway of hydrogen abstractor reactivity with proteins is not exploited.

The reaction of hydroxyl radical with alkyl C—H bonds is rapid, $10^8$ $M^{-1}s^{-}$ (Buxton et al., 1988, (*J. Phys. Chem. Ref. Data* 17:513–886) a value 10–100 fold less than the diffusion limit. This indicates that a hydrogen atom abstraction occurs on average every 10–100 collisions. This high frequency of reaction prevents hydroxyl radical generated in bulk solution from diffusing into the interior of macromolecular complexes. The success of DNA footprinting with hydroxyl radical demonstrates that formation of macromolecular complexes protects the residues at the molecular interface from reacting with hydroxyl radical. Tullius et al., 1987, *Methods of Enzymology* 155:537–558, Wu Ed., Academic Press: New York.

Electron spin resonance studies have also used carbon-centered radical mediated labeling of compounds to study molecules of interest, such as macromolecules. In EPR studies, a hydrogen atom abstractor, such as hydroxyl radical, is used to generate the carbon-centered radical of the molecule of interest. This highly unstable carbon-centered radical is then reacted with a spin trapping agent such as a nitrone. Buettner et al, 1990, *Methods in Enzymology* 186:127–133, Packer & Glazer, Eds., Academic Press: New York. Spin trapping agents are bulky and typically have a mass that exceeds 100 Daltons. The reaction of the carbon-centered radical with the spin trapping agent results in the covalent attachment of the spin trapping agent to the molecule of interest. In the case of molecules of interest such as peptides and proteins, the covalent attachment of bulky spin trapping agents is particularly unsatisfactory because it tends to reduce the solubility of the macromolecule, induces the macromolecule to adopt a nonphysiological conformation, and disrupts potential interactions, such as protein/protein or protein/drug interactions, that are the subject of the investigation.

Rather than using bulky spin trapping agents as taught by EPR studies, it is desirable to use a heavy hydrogen donor to "repair" carbon-centered radicals by donating a heavy hydrogen to the carbon-centered radical as shown FIG. 1. The advantage of such a repair reaction is that the molecule of interest is labeled with heavy hydrogen rather than a bulky spin trapping agent. Thus, the conformation of the molecule of interest is not altered and physiologically relevant information may be obtained. A second major advantage is that because this reaction is an isotope exchange reaction, the chemical nature of the molecule of interest is unchanged. This permits multiple solvent accessible reduced carbon atoms to be monitored in a single molecule, thus enhancing the sensitivity of the method over that of EPR studies. While such a "repair" approach is appealing in theory, reduction of such a reaction to practice has been particularly problematic, especially for molecules of interest that have low solubility in solution. One obstacle to achieving satisfactory results is that the hydrogen atom abstractor used to generate a carbon-centered radical in the molecule of interest tends to preferentially react with the heavy hydrogen donor rather then the molecule of interest. Another obstacle is that exposure of the molecule of interest to hydrogen atom abstractors such as hydroxyl radical tends to decompose the molecule of interest.

Goshe et al., June 1997, describes research directed to addressing the specific obstacles that prevent the attainment of satisfactory results from carbon-centered radical mediated hydrogen/heavy hydrogen labeling of molecules of interest. Goshe et al., June 1997, Meeting Abstract, American Society of Mass Spectroscopy, $45^{th}$ Annual Conference. Goshe et al., June 1997, used hydrogen atom abstractors, such as radiolysis generated hydroxyl radical, to remove hydrogens from reduced carbon atoms in free amino acids. This work raised the possibility that hydroxyl radical may be capable of abstracting a hydrogen atom from a C—H bond of the amino acids leucine and valine, producing a carbon-centered radical that is quenched by a heavy hydrogen donor via heavy hydrogen donation to the C-centered radical by a heavy hydrogen donor. However, even in the simple system described by Goshe et al., June 1997, conventional heavy hydrogen donors, such as ascorbic acid, do not provide for a satisfactory amount of heavy hydrogen incorporation into the molecule of interest. Goshe et al., June 1997, found that using dithiothreitol as a heavy hydrogen donor, rather than ascorbic acid, resulted in improved heavy hydrogen incorporation levels in molecules of interest such as the side chains of the free amino acids leucine and valine. Although Goshe et al., June 1997, supra, teaches an improved heavy hydrogen donor reagent, the conditions taught by Goshe et al., June 1997, remain unsatisfactory for the general study of molecules of interest. Under the conditions of Goshe et al., June 1997, the hydrogen atom abstractor preferentially oxidizes the heavy hydrogen donor rather than the molecule of interest. As a result, the heavy hydrogen donor supply in the reaction is rapidly depleted and the highly unstable carbon-centered radicals are not repaired with a hydrogen isotope. Rather, the carbon-centered radicals undergo a variety of undesirable reactions such as hydroxylation and crosslinking which degrades and/or denatures the molecule of interest. Further, if the hydrogen atom abstractor is hydroxyl radical concomitantly generated by radiolysis, solvated electrons generated by the radiolysis tend to also degrade the molecule of interest. This is particularly true of proteins and peptides, which the solvated electron readily reacts with, resulting in reductive cleavage of the amide bonds in the backbone. In simple systems, where the molecule of interest is highly soluble in solution and readily available, the problems provided by the Goshe et al., June 1997, reaction conditions can be partially offset by raising the concentration of the molecule of interest in the solution to a very high level. Because a high concentration of the molecule of interest is present in the solution, the small amount of sample that survives the reaction may be sufficient to detect heavy hydrogen incorporation. However, the partial remedy of increasing the concentration of the molecule of interest in the reaction is not a general solution to the problems presented by the Goshe et al., June 1997, reaction conditions because more complex molecules, such as peptides and proteins, do not have the solubility or stability required to overcome the problems presented by the Goshe et al., June 1997, reaction conditions.

According to the above background, there is a need for an improved method for the carbon-centered radical-mediated heavy hydrogen labeling of reduced carbon atoms in molecules of interest.

SUMMARY OF THE INVENTION

This invention provides an improved method for the carbon-centered radical mediated heavy hydrogen labeling of reduced carbon atoms in molecules of interest. Using the methods of the present invention, molecules of interest, including complex macromolecules such as peptides and proteins, can by studied using carbon-centered radical mediated heavy hydrogen labeling techniques. The methods of the present invention can be used to determine which reduced carbons of a molecule of interest are solvent accessible. Further, the methods of the present invention may be used to characterize amino acid residues that are involved in peptide-protein, protein-protein, and/or protein-drug interactions. The methods of the present invention have general utility in the field of life sciences. In particular, the methods of the present invention have significant utility in the fields of biochemistry, structural biology, and rational drug design.

According to the methods of the present invention, a solution containing a heavy hydrogen donor, a heavy hydrogen source, and a molecule of interest is prepared. Dissolved oxygen is removed from this solution, typically by bubbling the solution with an oxygen-free gas. When a substantial amount of oxygen has been removed from the solution, a hydrogen atom abstractor, such as hydroxyl radical, may then be generated in the solution by various methods disclosed herein. The hydrogen atom abstractor removes hydrogen atom from solvent accessible reduced carbons presented by the molecule of interest. As depicted in FIG. 1, the removal of hydrogen atoms from the molecule of interest results in the formation of the corresponding carbon-centered radical. The heavy hydrogen donor present in the solution repairs the carbon-centered radical using available sources of hydrogen present in the solution, including the heavy hydrogen source. Thus, heavy hydrogen is incorporated into a high percentage of the carbon-centered radicals. Because the reaction of the hydrogen atom abstractor with reduced carbons such as those found in alkyls is rapid, the method of the present invention is particularly effective at selectively labeling solvent accessible reduced carbons atoms. An additional feature of the present invention is that the labeling reaction is fast. The rate of the labeling reaction is limited by the rate of reaction of the heavy hydrogen donor with the carbon-centered radical. Thus if a heavy hydrogen donor having a very fast rate constant, such as dithiothreitol, is chosen the labeling reaction may be completed within milliseconds. Once the carbon atoms in the molecule of interest have been labeled with heavy hydrogen, using the methods of the present invention, the location of the heavy hydrogen can be determined by a variety of methods including electrospray ionization-mass spectroscopy, scintillation counting and/or NMR methods.

In a preferred embodiment, the hydrogen atom abstractor is generated using radiolysis. Radiolysis is a preferred technique for generating hydroxyl radical because the rate at which hydroxyl radical is generated in solution by various radiation sources has been accurately determined. Another major advantage of radiolysis is that it requires no additional chemical other than the water necessarily present in aqueous solution. Thus, it is possible to use a radiation source, such as $^{137}$Cs γ-ray source to generate hydroxyl radical in a solution at a very precise rate. By integrating this rate of hydroxyl radical generation over time, the total equivalent concentration of hydroxyl radical generated in a solution can be precisely and accurately determined. This has the advantage of making carbon-centered radical mediated heavy hydrogen labeling experiments highly reproducible. In addition, for a given molecule of interest, a series of labeling experiments using varying total equivalent concentrations of hydroxyl radical can be performed in order to provide an additional dimension of information about the solvent accessibility of particular solvent accessible carbon atoms in a molecule of interest.

If radiolysis is used to generate the hydrogen abstractor, in the methods of the present invention, the solution should be provided with an electron scavenger source prior to exposing the solution to the radiation source. The electron scavenger source absorbs the damaging free electrons that are generated in the solution by the radiation source. If $N_2O$ gas is used to remove a substantial amount of oxygen from the solution, then the $N_2O$ that dissolves into the solution as the $N_2O$ gas is bubbled into the solution serves as a preferred electron scavenger source.

In a preferred embodiment, the solution includes an internal reference. The internal reference serves to normalize the effective hydroxyl radical dose between successive labeling experiments. The internal reference is a molecule having reduced carbon atoms that readily exchanges with heavy hydrogen using the methods of the present invention. A preferred internal reference is leucine or norleucine.

In another preferred embodiment, the carbon-centered radical mediated heavy hydrogen labeling reaction is repeated a multiple number of times in succession on the same sample. Between each exchange reaction, additional reduced heavy hydrogen donor is added to the sample solution to compensate for the heavy hydrogen donor in the sample that is lost during the labeling reaction. Additionally, if the hydrogen atom abstractor is hydroxyl radical generated by radiolysis, additional amounts of electron scavenger source is added to the solution between exchange reactions to compensate for depletion of the electron scavenger source in the exchange reaction. In a preferred embodiment, this electron scavenger source is provided by bubbling the solution with $N_2O$ gas.

In yet another preferred embodiment, the molecule of interest is a peptide or protein. The exchange reaction isotopically labels particular solvent accessible side chains on the peptide or protein. The determination of the amino acid residues containing the isotopic label provides a means of assigning residues of proteins as solvent accessible and can be employed to study protein conformational changes and protein-protein interactions at the amino acid level. The formation of stable carbon-heavy hydrogen bond using carbon-hydrogen/heavy hydrogen exchange has the advantage over amide hydrogen/heavy hydrogen exchange of (1) producing highly stable carbon-heavy hydrogen label and (2) selectively targeting the heavy hydrogen label to solvent accessible side chains, rather than just amide backbones.

DETAILED DESCRIPTION OF THE INVENTION

1. DEFINITIONS

Figure 1:
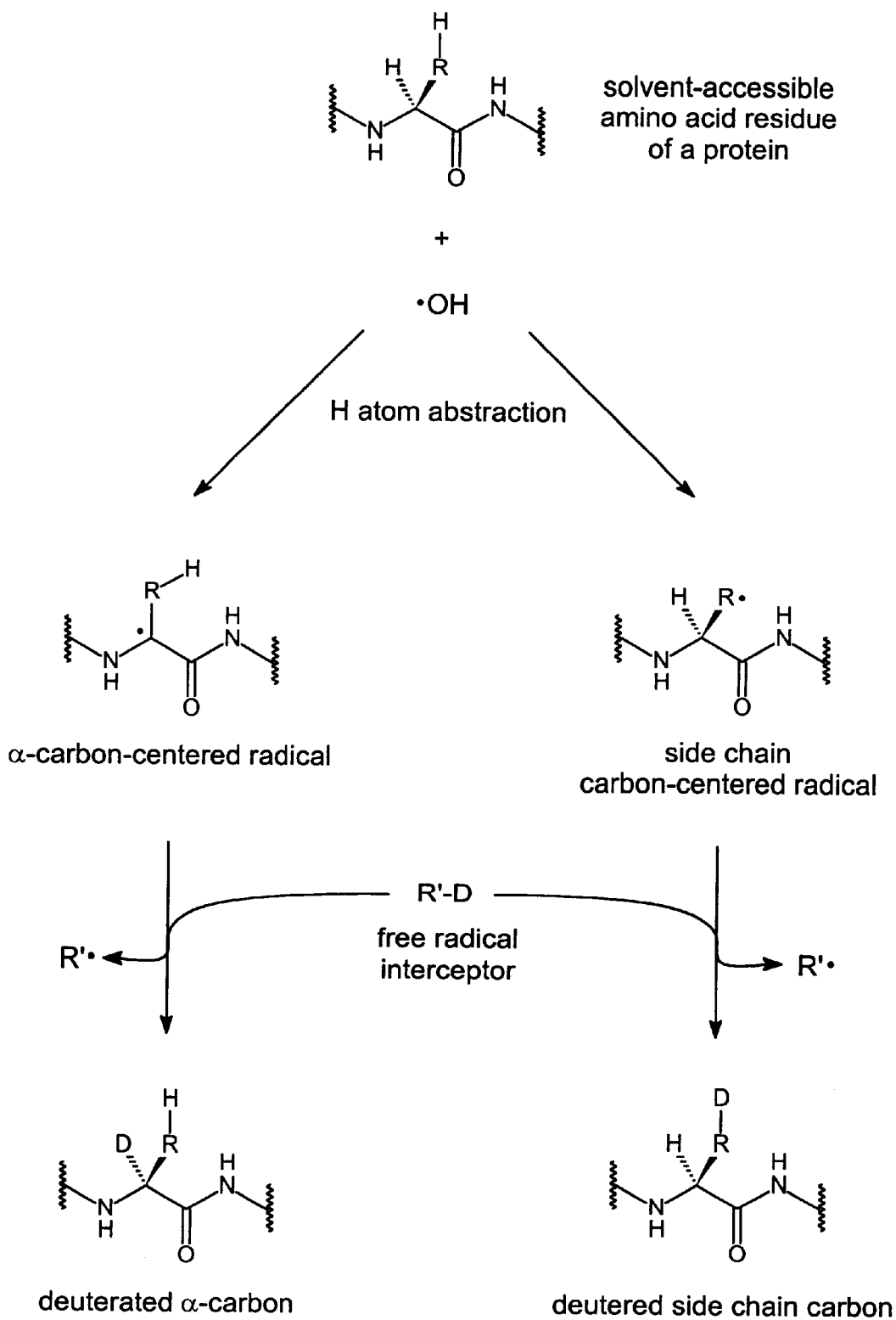
FIG. 1 is a schematic of the potential chemical fates of a C-centered radical in an amino acid residue of a protein (or peptide) when a free radical interceptor is present.

As used herein, the following terms shall have the following meanings:

"hydroxyl radical" refers to OH radical, OD radical and/or TO radical. The hydroxyl radical can be generated in aqueous solutions by radiolysis, commonly effected by γ-ray emission in $^{60}$Co and $^{137}$Cs irradiators. The interaction of ionizing radiation with matter results in ionization and electronic excitation. In aqueous solutions, reactions I and II will occur:

$$H_2O \xrightarrow{\text{ionizing radiation}} H_2O^{+\bullet} + e^- \quad \text{I}$$

and $$H_2O \xrightarrow{\text{ionizing radiation}} H_2O^* \quad \text{II}$$

Reactions I and II initiate a series of other reactions. For example, $H_2O^+$ is a strong acid and rapidly loses a proton to the surrounding water molecules in the aqueous solution to produce hydroxyl radical according to the following reaction:

$$H_2O^+ + H_2O \rightarrow H_3O^+ + \cdot OH \quad \text{III}$$

Further electron ($e^-$) formed in reaction I becomes solvated, resulting in an aqueous electron ($e^-_{aq}$).

$$e^- + nH_2O \rightarrow e^-_{aq} \quad \text{IV}$$

The excited water molecules ($H_2O^*$) formed in reaction II can break up into hydrogen atoms and hydroxyl radicals:

$$H_2O^* \rightarrow H\cdot + \cdot OH \quad \text{V}$$

The solvated electron ($e^-_{aq}$) generated via reaction IV can be used to form hydrogen atoms:

$$e^-_{aq} + H^+ \rightarrow H\cdot \quad \text{VI}$$

In addition, hydrogen peroxide ($H_2O_2$) and hydrogen gas ($H_2$) can be produced according to the following reactions:

$$H\cdot + H\cdot \rightarrow H_2 \quad \text{VII}$$

$$e^-_{aq} + e^-_{aq} \rightarrow H_2 + 2OH^- \quad \text{VIII}$$

$$\cdot OH + \cdot OH \rightarrow H_2O_2 \quad \text{IX}$$

The radicals formed within a spur, which is a small packet of energy deposited by an ionizing particle passing through absorbing matter, may be combined as shown in reactions X to XII.

$$H\cdot + \cdot OH \rightarrow H_2O \quad \text{X}$$

$$e^-_{aq} + \cdot OH \rightarrow OH^- \quad \text{XI}$$

$$H^+ + OH^- \rightarrow H_2O \quad \text{XII}$$

Although reactions VI through XII are nearly diffusion limited, a considerable number of the radicals escape the spur and can be intercepted in solution by other chemical species, such as peptides and proteins.

To generate a more restricted radical source than a mixture of hydroxyl radical, hydrogen atom, and $e^-_{aq}$, electron scavenger sources can be added to a solution. For example, saturating water with nitrous oxide ($N_2O$) can produce a radical yield of 90% hydroxyl radical and 10% hydrogen atoms. $N_2O$ converts $e^-_{aq}$ into hydroxyl radicals according to the reaction:

$$e^-_{aq} + N_2O \rightarrow \cdot OH + N_2 + OH^- \quad \text{XIII}$$

"heavy hydrogen" refers to deuterium or tritium.

"sample" and "sample solution" refers to the solution containing the molecule of interest that is subjected to the labeling method of the present invention.

"total equivalent concentration of hydroxyl radical" refers to the total amount of hydroxyl radical that is generated in the sample during one hydroxyl radical generation step divided by the volume of the sample. The total amount of hydroxyl radical generated in the sample during one hydroxyl radical generation step is determined by integrating the rate at which hydroxyl radical is created in the solution over the length of time of the generation step. For example consider an embodiment of the present invention in which the sample has a volume of 1 mL. During the hydroxyl radical generation step, the sample is exposed to $^{137}$Cs γ-ray source for a period of time. At any given instant during the hydroxyl radical generation step the concentration of hydroxyl radical in the sample may only be in the nM to low $\mu$M range because the hydroxyl radical is very reactive and is rapidly consumed. However, if the time period of the hydroxyl radical generation step is sufficiently long, the integrated total amount of hydroxyl radical generated in the sample becomes quite large. By dividing the integrated total amount (mM) of hydroxyl radical generated in the sample by the volume of the sample, the total equivalent concentration of hydroxyl radical is computed.

"radiolysis" or "pulse radiolysis" is a technique used in the study of the kinetics of radiation-induced reactions involving free radicals and unstable chemical intermediates. The technique employs a radiation pulse that is short relative to the time scale of the chemical reaction being monitored. The radiation pulse can vary from nanoseconds to submicroseconds and must generate a sufficient amount of the chemical species suitable for detection. A variety of detection systems have been developed that include UV-VIS spectophotometry, Raman spectroscopy conductometry, polarography, light scattering, and electron spin resonance (EPR). Radiolysis has been used to determine the rate constants of hydroxyl radical reacting with many organic compounds, including all naturally occurring free amino acids. For amino acid rate constants see Buxton et al., 1988, *J. Phys. Chem. Ref. Data* 17:513–886.

"alkyl" refers to a saturated branched, straight chain or cyclic hydrocarbon radical. Typical alkyl groups include, but are not limited to, methyl, ethyl, propyl, isopropyl, cyclopropyl, butyl, isobutyl, t-butyl, cyclobutyl, pentyl, isopentyl, cyclopentyl, hexyl, cyclohexyl and the like. Alkyl groups include ($C_1$–$C_{50}$) alkyls, more preferably ($C_1$–$C_{25}$) alkyls and most preferably ($C_1$–$C_{10}$) alkyls.

"alkenyl" refers to an unsaturated branched, straight chain or cyclic hydrocarbon radical having at least one carbon-carbon double bond. The radical may be in either the cis or trans conformation about the double bond(s). Typical alkenyl groups include, but are not limited to, ethenyl, vinylidene, propenyl, propylidene, isopropenyl, isopropylidene, butenyl, butenylidene, isobutenyl, tert-butenyl, cyclobutenyl, pentenyl, isopentenyl, cyclopentenyl, hexenyl, cyclohexenyl and the like. In preferred embodiments, the alkenyl group is ($C_2$–$C_8$) alkenyl, more preferably ($C_2$–$C_6$) alkenyl and most preferably ($C_2$–$C_3$) alkenyl.

"alkynyl" refers to an unsaturated branched, straight chain or cyclic hydrocarbon radical having at least one carbon-carbon triple bond. Typical alkynyl groups include, but are not limited to, ethynyl, propynyl, butynyl, isobutynyl, pentynyl, hexynyl and the like. In preferred embodiments, the alkynyl group is ($C_2$–$C_8$) alkynyl, more preferably ($C_2$–$C_6$) and most preferably ($C_2$–$C_3$) alkynyl.

"substituted alkaryl" refers to an alkaryl radical wherein one or more hydrogen atoms on the aryl moiety are each independently replaced with another substituent. Typical substituents include, but are not limited to, —OR, —SR, —NRR, —CN, —NO$_2$, —C(O)R, —C(O)OR, —C(O)NRR, —C(S)NRR, —C(NRR)NR, —NR—C(O)R, —C(NRR)=NOR, —C(O)NROR, —NR—C(O)—NRR, -halogen and -trihalomethyl, where each R is independently —H, alkyl, alkenyl, alkynyl, aryl, alkaryl, heteroaryl or alk-heteroaryl as defined herein.

"cycloalkyl" refers to a cyclic or polycyclic saturated or unsaturated hydrocarbon radical. Typical cycloalkyl groups include, but are not limited to, cyclopropanyl, cyclobutanyl, cyclopentanyl, cyclohexanyl and higher cycloalkyls, adamantyl, cubanyl, prismanyl and higher polycylicalkyls, etc. In preferred embodiments, the cycloalkyl is (C$_3$–C$_{10}$) cycloalkyl. Representative cycloalkyls are cyclohexanyl and adamantyl.

"substituted cycloalkyl" refers to a cycloalkyl or radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, (C$_1$–C$_{50}$) alkyl, (C$_5$–C$_{25}$) aryl, and (C$_6$–C$_{10}$) alkaryl as defined herein.

"heterocycloalkyl" refers to a cycloalkyl moiety wherein one of the ring carbon atoms is replaced with another atom such as N, P, O, S, As, Ge, Se, Si, Te, etc. Typical heterocycloalkyls include, but are not limited to, imidazolidyl, piperazyl, piperidyl, pyrazolidyl, pyrrolidyl, quinuclidyl, etc. In preferred embodiments, the heterocycloalkyl is 5–10 membered. Representative heterocycloalkyls are morpholino, tetrahydrofuryl, and pyrrolidyl.

"substituted heterocycloalkyl" refers to a cycloheteroalkyl radical wherein one or more hydrogen atoms are each independently replaced with another substituent. Typical substituents include, but are not limited to, —R, —OR, —SR, —NRR, —CN, —NO$_2$, —C(O)R, —C(O)OR, —C(O)NRR, —C(NRR)=NR, —C(O)NROR, —C(NRR)=NOR, —NR—C(O)R, -tetrazol-5-yl, —NR—SO$_2$—R, —NR—C(O)—NRR, —NR—C(O)—OR, -halogen and -trihalomethyl where each R is independently —H, (C$_1$–C$_8$) alkyl, (C$_2$–C$_8$) alkenyl, (C$_2$–C$_8$) alkynyl, (C$_5$–C$_{20}$) aryl, (C$_6$–C$_{26}$) alkaryl, 5–20 membered heteroaryl, and 6–26 membered alk-heteroaryl as defined herein.

"aryl" refers to an unsaturated cyclic hydrocarbon radical having a conjugated π electron system. Typical aryl groups include, but are not limited to, penta-2,4-dienyl, phenyl, naphthyl, aceanthrylyl, acenaphthyl, anthracyl, azulenyl, chrysenyl, indacenyl, indanyl, ovalenyl, perylenyl, phenanthrenyl, phenalenyl, picenyl, pyrenyl, pyranthrenyl, rubicenyl and the like. In preferred embodiments, the aryl group is (C$_5$–C$_{20}$) aryl, more preferably (C$_5$–C$_{10}$) aryl and most preferably phenyl.

"alkaryl" refers to a straight-chain alkyl, alkenyl or alkynyl group wherein one of the hydrogen atoms bonded to the terminal carbon is replaced with an (C$_5$–C$_{20}$) aryl moiety. Alkaryl also refers to a branched-chain alkyl, alkenyl or alkynyl group wherein one of the hydrogen atoms bonded to a terminal carbon is replaced with an aryl moiety. Typical alkaryl groups include, but are not limited to, benzyl, benzylidene, benzylidyne, benzenobenzyl, naphthalenobenzyl and the like. Representative alkaryl groups include (C$_6$–C$_{26}$) alkaryl, i.e., the alkyl, alkenyl or alkynyl moiety of the alkaryl group is (C$_1$–C$_6$) and the aryl moiety is (C$_5$–C$_{20}$).

"heteroaryl" refers to an aryl moiety wherein one or more carbon atoms has been replaced with another atom, such as N, P, O, S, As, Ge, Se, Si, Te, etc. Typical heteroaryl groups include, but are not limited to acridarsine, acridine, arsanthridine, arsindole, arsindoline, benzodioxole, benzothiadiazole, carbazole, β-carboline, chromane, chromene, cinnoline, furan, imidazole, indazole, indole, isoindole, indolizine, isoarsindole, isoarsinoline, isobenzofuran, isochromane, isochromene, isoindole, isophosphoindole, isophosphinoline, isoquinoline, isothiazole, isoxazole, naphthyridine, perimidine, phenanthridine, phenanthroline, phenazine, phosphoindole, phosphinoline, phthalazine, piazthiole, pteridine, purine, pyran, pyrazine, pyrazole, pyridazine, pyridine, pyrimidine, pyrrole, pyrrolizine, quinazoline, quinoline, quinolizine, quinoxaline, selenophene, tellurophene, thiazopyrrolizine, thiophene and xanthene. In preferred embodiments, the heteroaryl group is a 5–20 membered heteroaryl, with 5–10 membered heteroaryl being particularly preferred.

"alk-heteroaryl" refers to a straight-chain alkyl, alkenyl or alkynyl group where one of the hydrogen atoms bonded to a terminal carbon atom is replaced with a heteroaryl moiety. Representative alk-heteroaryl groups are 6–26 membered alk-heteroaryls, i.e., the alkyl, alkenyl or alkynyl moiety of the alk-heteroaryl is (C$_1$–C$_6$) and the heteroaryl moiety is a 5–20-membered heteroaryl.

"molecule of interest" refers to any molecule that includes one or more reduced carbon atoms. Representative molecules of the present invention include, but are not limited to, molecules having one or more alkyls, substituted alkyls, cycloalkyls, substituted cycloalkyls, heterocycloalkyls, substituted heterocycloalkyls, aryls, alkaryls, and/or heteroaryls. Molecules of interest include peptides and proteins that comprise residues derived from naturally occurring and/or unnatural amino acids. See e.g. Stryer, 1988, Biochemistry 3$^{rd}$ Edition, W.H. Freeman and Company, New York; Sigma, 1998, "Biochemicals and Reagents for Life Science Research", Sigma, St. Louis, Mo.

"labeled with heavy hydrogen" A reduced carbon atom in a molecule of interest is considered labeled with heavy hydrogen if the isotopic ratio of heavy hydrogen to hydrogen for that particular reduced carbon atom in a sample of the molecule of interest increases by a detectable amount as a result of the carbon-centered radical mediated heavy hydrogen labeling reaction of the present invention. A detectable increase in the isotopic ratio is dependent upon the method used to analyze the isotopic ratio. If the mass spectroscopy or NMR is used, an increase of less then one percent in the heavy hydrogen to hydrogen isotope ratio may be detected.

"heavy hydrogen source" refers to a heavy hydrogen source is any compound that can serve as a source of deuterium or tritium. In a preferred embodiment, the heavy hydrogen source is D$_2$O.

"heavy hydrogen donor" refers to any compound that is capable of donating a hydrogen atom to a carbon-centered radical under aqueous anaerobic conditions. Representative hydrogen donors include, but are not limited to, reduced water soluble thiols, dithiothreitol, H$_2$S, L-Ascorbic Acid, (±)-α-tocopherol, phenols, and phosphine or phosphites having a P—H, P—D or P—T bond.

"solvent accessible residues" refers to a residue in a molecule of interest that has over twenty percent of its surface area contacted by a 1.4 Angstrom test sphere as described by Connolly. Connolly, 1983, Science, 221:709–13. Similarly, a solvent accessible reduced carbon atom is one having over twenty percent of its surface area contacted by a 1.4 Angstrom test sphere.

"electron scavenger source" refers to any compound that effectively protects the molecule of interest from solvated electrons during the carbon-centered radical mediated heavy hydrogen labeling of the molecule of interest. Electron scavenger sources of the present invention preferably have the following properties: (i) they react with solvated electrons at a rate constant of greater then $10^8$ Moles/Second (ii), they are not reactive with the hydrogen atom abstractor and (iii), they do not degrade or significantly affect the conformation of the molecule of interest. Preferred electron scavengers include, for example, dissolved $N_2O$, ascorbate, tetranitromethane, nitrate ($NO_3$—), $CCl_4$ as well as members of the compound classes listed in Table 1.

TABLE 1

Electron Scavenger Source-Preferred Classes

| Class | Examples |
| --- | --- |
| thiols | cysteine |
| disulfides | oxidized dithiothreitol |
| fluorinated aromatics | hexafluorobenzene |
| nitro aromatics | nitrobenzene, dinitrobenzene, and nitrothiophene |

Additional preferred electron scavenger sources can be found, for example, in Buxton et al., 1988, "Critical Review of rate constants for reactions of hydrated electrons, hydrogen atoms and hydroxyl radicals in aqueous solution", J. Phys. Chem. Ref. Data 17(2):514–886. Further, one of skill in the art will recognize that any mixture of $N_2O$, ascorbate, tetranitromethane, nitrate ($NO_3$—), $CCl_4$, thiols, disulfides, fluorinated aromatics, nitro aromatics, and other suitable electron scavengers may be used in the methods of the present invention. As used herein, fluorinated aromatics refer to a compound having one or more benzyl moieties in which one or more positions on a benzyl ring of the compound is substituted with a fluoro. Similarly, nitro aromatics refer to compounds having one or more benzyl moieties in which one or more of the carbon atoms in a benzyl ring of the compound is substituted with a nitro.

2. THE METHOD

The present invention discloses a method of labeling a reduced carbon atom in a molecule of interest with a heavy hydrogen. The method comprises generating a hydrogen atom abstractor in a solution. The solution includes a molecule of interest, a heavy hydrogen source, and a heavy hydrogen donor. In the method, the hydrogen atom abstractor reacts with the reduced carbon atom in the molecule of interest to form a corresponding carbon-centered radical of the reduced carbon atom, and the heavy hydrogen donor donates the heavy hydrogen to the carbon-centered radical, thereby labeling the reduced carbon atom in the molecule of interest with the heavy hydrogen. When the hydrogen atom abstractor is generated in the solution, the solution must be substantially oxygen free. The method is described in more detail in sections (A)–(E) below.

A. Preparation of a sample. According to the methods of the present invention, a solution containing a heavy hydrogen donor, a heavy hydrogen source, and a molecule of interest is prepared. Any sample volume desired may be used. However, practical limitations on the volume are typically imposed by the fact that the solution must be substantially oxygen free when a hydrogen abstractor is generated (see sections B, C). In a preferred embodiment, 1.5 ml glass vials containing a screw cap and a Teflon-silicone septum are used.

Because the methods of the present invention involve the use of a hydrogen atom abstractor (section C), the solution used in the present invention is preferably aqueous. The use of even small amounts of a cosolvent, while potentially tolerable, is not preferred. If even low concentrations of a cosolvent, such as dimethylsulfoxide are present in the solution, the reactivity of the hydrogen atom abstractor is greatly affected. For example, inclusion of one percent DMSO (v/v) to the solution results in a solution that is in excess of 50 mM DMSO. This DMSO will preferentially react with hydrogen atom abstractors such as hydroxyl radical. The rate constant for the reaction of hydroxyl radical with DMSO is on the order of $5 \times 10^9$ Mol/second. The undesired reaction of the hydroxyl radical with DMSO will result in complete conversion of the hydroxyl radical to methyl radical. Methyl radical is a less reactive hydrogen atom abstractor then hydroxyl radical and therefore is not preferred. Similarly, the reaction of DMSO with hydrogen atom abstractors other then hydroxyl radical result in the generation of significantly less reactive hydrogen atom abstractors that do not facilitate the labeling reaction.

The concentration of the molecule of the interest used in the methods of the present invention is largely determined by the solubility of the molecule of interest in the solution. Further, if the method of the present invention is used to study the interaction of the molecule of interest with a second molecule, such as a protein, peptide, and/or inhibitor, the concentration of the molecule of interest necessary to facilitate an intermolecular interaction with the second molecule must be used. In the absence of such considerations, the methods of the present invention may work when the molecule of interest is present in the solution at a concentration of about 0.05 $\mu$M or less. More preferably the concentration is 0.1 $\mu$M or more and, even more preferably, the concentration is 1 $\mu$M or more. However, the concentration of the molecule of interest typically does not provide any general limitation to the methods of the present invention. Rather, what is typically important is the total amount of the molecule of interest that is used in the labeling reaction. A sufficient amount of the molecule of interest must be used to allow for detection of heavy hydrogen incorporation into the molecule of interest. With existing mass spectrometers, this detection requirement provides a present technical limitation requirement such that about 100 pM to about 1 nM of molecule of interest should be used in the labeling reaction so that the label can be detected. By increasing the volume of the solution, the concentration of the molecule of interest in the solution may be adjusted to any desired concentration. It is widely expected that, with enhanced mass spectrometry facilities, the amount of molecule of interest that must be labeled in order to detect a signal should be reduced 10–100 fold or more in the near future. Consequently, even lower concentrations and amounts of the molecule of interest will be successfully labeled in the future. Further, by using the heavy hydrogen tritium and studying the labeled molecule of interest by scintillation counting, very low amounts of the molecule of interest may be required in the labeling reaction.

The labeling reaction is not sensitive to temperature as long a temperature for the reaction is chosen that does not affect the desired conformation of the molecule of interest. Since physiological states are typically studied using the methods of the present invention, the labeling reaction is typically run at about room temperature, although other temperatures are within the scope of the present invention.

The concentration of heavy hydrogen donor that is present in the solution depends on the type of heavy hydrogen donor that is used. In a preferred embodiment, the heavy hydrogen donor is dithiothreitol, $H_2S$, L-Ascorbic Acid, (±)-α-tocopherol, phenols, and/or phosphines and phosphites having a P—H, P—D or P—T bond. Of these heavy hydrogen donors, dithiothreitol is preferred.

The labeling reaction of the present invention is not dependent upon pH as long as the pH used does not strip the hydrogen atom donor of its reactive hydrogen. Thus, if the hydrogen atom donor is dithiothreitol, then any pH below 9 may be used in the labeling reaction. Despite the pH independent nature of the labeling reaction, buffers are used in a preferred embodiment because they standardize the results of successive labeling experiments and they place sample, such as peptides and proteins, in a reproducible state. If irradiation is used to generate a hydrogen atom abstractor, only buffers that will not react with the hydroxyl radical and solvated electrons that are generated by the irradiation may be used as buffers in the labeling reaction. Such buffers include phosphate and cacodylate. Buffers such as that of Goode et al. are not desirable because they have chemical functionality that reacts with the hydrogen atom abstractor.

In principle, very low concentrations of heavy hydrogen may successfully be used in the present invention. For example, even if as little as 0.1% mole fraction of $D_2O$ to total solution is used in the labeling reactions, a meaningful isotope ratio signal could be measured. In a preferred embodiment, the solution comprises 80% (v/v) $D_2O$ or more to enhance the amount of label incorporated into the molecule of interest.

The labeling reaction is not sensitive to the amount of pressure that is applied to the solution. Typically, the labeling reaction is run at normal atmospheric pressure (1 atm, 760 torr). However, as detailed below, using a lower pressure than 1 atm could facilitate the removal of oxygen from the solution. Alternatively, imposing a higher pressure, using an oxygen free gas, may be desirable in order to minimize the amount of oxygen dissolved in the solution.

B. Removal of oxygen from the sample. When a hydrogen atom abstractor is generated in the solution containing the molecule of interest, the solution must be substantially oxygen free. That is, a substantial amount of the dissolved oxygen normally present in a solution under atmospheric pressure (one atm, 760 torr) must be removed from the solution containing the molecule of interest. The extent to which the solution must be substantially oxygen free is somewhat dependent upon the nature of the molecule of interest. If the solution is not substantially oxygen free, then an unsatisfactory small percentage of the solvent accessible carbon-centered radicals formed by the reaction of the reduced carbon atoms in the molecule of interest and the hydrogen atom abstractor will become labeled with heavy hydrogen. Rather, undesirable reactions will occur that result in, among other things, the oxidation of the reduced carbon atoms. The adverse effects of oxygen in radiolysis using solution with no oxygen removed from the solution have been explored in, for example, King. King, 1993, Ph.D. Thesis, Brown University Chemistry Department. King studied aerobic radiolysis of molecules of interest, such as amino acids and peptides, and determined that (i) the undesired oxidization of the molecule of interest predominantly localizes to the side chains of the amino acids and (ii) there is a large number of undesired products generated when even a simple peptide was subjected to radiolysis under aerobic conditions.

In a preferred embodiment, the solution is substantially oxygen free when carbon-centered radicals are preferentially repaired with hydrogen rather then oxidized. When using the reaction conditions of this embodiment, a measurable percentage of the hydrogen that react with the carbon-centered radicals will be a heavy hydrogen isotope. If less then a substantial amount of oxygen is removed from the solution in this embodiment, then the isotope repair reaction of the carbon-centered radicals will not be favored over oxidation reactions. The resulting oxidation of the solvent accessible carbons atoms on the molecule of interest will adversely affect the conformation of the molecule to the point that the labeling information derived from the reaction will be of very little value.

The following additional embodiments serve to further illustrate the substantially free oxygen requirement of the present invention.

In a preferred embodiment, the solution is substantially oxygen free when at least one solvent accessible reduced carbon atom in the molecule of interest is labeled with a heavy hydrogen using the carbon-centered radical mediated heavy hydrogen labeling reaction of the present invention. In a more preferred embodiment, the solution is substantially oxygen free when at least five percent of the solvent accessible reduced carbon atoms in the molecule of interest are labeled with heavy hydrogen using the carbon-centered radical mediated heavy hydrogen labeling reaction of the present invention.

In another embodiment, the solution is substantially oxygen free when a heavy hydrogen is donated by the heavy hydrogen donor to at least one carbon-centered radical formed by the reaction of the hydrogen atom abstractor with a reduced carbon atom in the molecule of interest. In a more preferred embodiment, the solution is substantially oxygen free when at least five percent of the carbon-centered radicals, which are formed by the reaction of the hydrogen atom abstractor with the reduced carbon atoms in the molecule of interest, are labeled with heavy hydrogen. In still a more preferred embodiment, the solution is substantially oxygen free when at least fifty percent of the carbon-centered radicals, which are formed by the reaction of the hydrogen atom abstractor with the reduced carbon atom in the molecule of interest, are labeled with heavy hydrogen. In still a more preferred embodiment, the solution is substantially oxygen free when at least eighty percent of the carbon-centered radicals, which are formed by the reaction of the hydrogen atom abstractor with the reduced carbon atom in the molecule of interest, are labeled with heavy hydrogen.

In another preferred embodiment, the solution is substantially oxygen free when it has been contacted with a gas, having less than about 3000 parts per million $O_2$, for at least an amount of time that is sufficient to make the concentration of dissolved $O_2$ dissolved in the solution 6 $\mu$M or less. Suitable gases used in this embodiment of the invention, include, but are not limited to, $N_2O$, $N_2$, argon, helium, and anoxic mixtures thereof. In one embodiment, the solution is contacted with the gas by bubbling the gas into the solution.

In still another preferred embodiment, the solution is substantially oxygen free when it has been contacted with a $N_2O$ gas, having less than about 3000 parts per million $O_2$, for a sufficient amount time such that at least five percent of the carbon-centered radicals, which are formed by a reaction of the hydrogen atom abstractor with reduced solvent accessible carbon atoms in the molecule of interest, are repaired by donation of a hydrogen isotope by the heavy hydrogen donor.

A considerable number of methods are known for making a solution anaerobic. Such conventional methods are within the scope of the present invention as long as they facilitate the labeling reaction. A preferred method for providing anaerobic conditions is to contact the solution with an oxygen free gas. If the gas is bubbled into the solution, then the length of time that it takes to remove a substantial amount of dissolved oxygen from the solution is significantly shortened. That is because, as the oxygen free gas is bubbled into the solution, oxygen from the dissolved solution equilibrates with the oxygen-free air bubble, thus rapidly depleting the amount of dissolved oxygen that remains in the solution. Any oxygen free gas that does not interfere with the labeling reaction is within the scope of the present invention. Suitable oxygen free gases include, but are not limited to, $N_2O$, $N_2$, argon, helium, and anoxoxic mixtures thereof. A typical anoxoxic mixture may comprise, for example, 10% $N_2O$ in 90% $N_2$. In a preferred embodiment, the oxygen-free gas is Medipure™ U.S.P. grade $NO_2$ gas, which contains 300 parts per million $O_2$. In an even more preferred embodiment, the oxygen free gas is Semiconductor Grade 4.8 $NO_2$ gas containing less than 1 ppm $O_2$ (PraxAir, Cleveland, Ohio).

In some embodiments of the present invention, the study of particularly difficult molecules of interest may require that the solution have a dissolved oxygen concentration of less then 10 nM when the hydrogen atom abstractor is generated. If this is the case, a coupled enzymatic system, potentially glucose oxidase, glucose, and catalase may be used to lower the amount of oxygen in the solution below the required threshold. The glucose oxidase takes $O_2$ and the substrate glucose and generates $H_2O_2$ and a two electron oxidized substrate (gluconic acid). The catalase disproportionates the $H_2O_2$ into $H_2O$ and $O_2$ (the net being the loss of ½ $O_2$). This enzymatic scavenging of $O_2$ is exceptionally effective at reducing $O_2$ concentrations to 1 nM or less.

C. Generation of a hydrogen atom abstractor. When a substantial amount of oxygen has been removed from the solution, a hydrogen atom abstractor is generated in the solution. As used herein, a hydrogen atom abstractor is any entity that is capable of abstracting a hydrogen from a C—H bond under anaerobic conditions. Such hydrogen atom abstractors include, but are not limited to, peroxonitrous acid, the hydrogen atom, hydroperoxyl radical, alkoxyl radicals, alkyl radicals, singlet oxygen, metal oxo species such as the ferryl oxo species from the reaction of heme Fe with $H_2O_2$, and the hydroxyl radical. The most preferred hydrogen atom abstractor of the present invention is the hydroxyl radical.

Hydrogen atom abstractors other then the hydroxyl radical have the disadvantage that they are almost universally more selective than hydroxyl radical in their reaction, thus fewer potential sites of solvent accessibility on the molecule of interest are probed. When hydrogen atom abstractors other then hydroxyl radical are used, the ratio of reactivity with the molecule of interest and the heavy hydrogen donor becomes less favorable, so that a greater fraction of the oxidative species reacts directly with the heavy hydrogen donor rather than having the reaction mediated by an intermediate reduced carbon radical. Finally, the alternative hydrogen atom abstractors are larger than hydroxyl radical, leading to a lower resolution probe of the solvent accessible surfaces.

The hydrogen atom abstractor removes hydrogen atom from solvent accessible reduced carbons on the molecule of interest. The removal of hydrogen atoms from the molecule of interest results in the formation of the corresponding carbon-centered radical. The heavy hydrogen donor present in the solution repairs the carbon-centered radical using available sources of hydrogen present in the solution, including the heavy hydrogen source. Thus, heavy hydrogen is incorporated into a percentage of the carbon-centered radicals. Because the reaction of the hydrogen atom abstractor with reduced carbons such as those found in alkyls is rapid, the method of the present invention is particularly effective at selectively labeling solvent accessible reduced carbons atoms. An additional feature of the typically fast reaction rate of hydrogen atom abstractors of the present invention with reduced carbons is that the repair reaction is completed within milliseconds.

The hydroxyl radical may be generated by several different means. For example, the hydroxyl radical may be generated by subjecting the solution to radioactive source such as $^{60}Co$ or $^{137}Cs$. Radioactive phosphate ($^{32}PO_4$), which has been successfully used in the DNA-protein footprinting field, will also work in the methods of the present invention. Alternatively the sample may be exposed to x-rays, such as Cu $K_\alpha$ or molybdenum $K_\alpha$ radiation from a standard source such as Rigaku generator, in order to generate the hydroxyl radical. The sample may also be exposed to synchrotron radiation in order to generate the hydroxyl radical. Hydroxyl radical may also be generated in the sample by exposing the sample to a neutron source such as the neutron source provided by the Brookhaven National Light Source (New York). It is possible that hydroxyl radicals may also be generated using an electronic plasma that is generated by radio frequency or high voltage. For example, hydroxyl radical may be generated as described in Maleknia et al. Maleknia et al., *Rapid Communications in Mass Spectroscopy* 13:2352–2358, 1999.

In an alternative embodiment, hydroxyl radicals are generated in the solution by using ultra violet (UV) light sensitive hydroperoxides. In this alternative embodiment, a UV light sensitive hydroperoxide is added to the solution and the solution is exposed to UV light. The UV light photolyzes the hydroperoxide to hydroxyl radical and an organic alkoxyl radical.

In yet another embodiment, hydroxyl radical can be generated using Fe-EDTA-$H_2O_2$ and similar reduced metal ions to reduce $H_2O_2$ to hydroxyl radical. There are several different types of metals that may be used to reduce $H_2O_2$ to hydroxyl radical. This type of reaction is well known in the art as "Fenton chemistry" and the metals according to this embodiment of the invention are referred to in the art as Fenton reagents.

In a preferred embodiment radiolysis is used in the methods of the present invention because it is chemically clean and there is no need to add any additional chemical to the solution, which is a prerequisite in several of the other embodiments. Preferably, radiolysis using $^{137}Cs$ is used in the methods of the present invention.

D. Determining the location of heavy hydrogen label in the molecule of interest.

Once the carbon atoms in the molecule of interest have been labeled with heavy hydrogen, the location of the heavy hydrogen can be determined by a variety of methods. Representative methods include electrospray ionization-mass spectroscopy, scintillation counting, and/or nuclear magnetic resonance. In particular, as described in the examples section (Section 3), whole molecule isotope ratios of molecules of interest may be determined using mass spectroscopy techniques such as, for example, gas chromatography-mass spectrometry (GC-MS), electrospray ionization-mass spectrometry (ESI-MS), and/or reversed phase high performance liquid chromatography-electrospray ionization-mass spectrometry (HPLC-ESI-MS or LC-MS).

E. Modeling experiments using heavy hydrogen labeling data. The heavy hydrogen isotope ratio data obtained using the methods of the present invention may be used to model the solvent accessible area of a molecule of interest. For example, models may be built using HyperChem® software (Hypercube, Inc.) using surface area calculations performed with ChemPlusTM: extensions for HyperChem® (Hypercube, Inc.). For peptides and proteins, the solvent-accessible surface area is typically calculated by a grid method. For such calculations a solvent probe radius of 1.4 Å, three body correction, and 20 points on a cube side is often used.

Using radiolysis to generate hydroxyl radical. In a preferred embodiment, the hydrogen atom abstractor is hydroxyl radical generated by radiolysis. Radiolysis is a preferred technique for generating hydroxyl radical because the rate at which hydroxyl radical is generated in solution by various radiation sources has been accurately determined. Primary radiolysis reactions are extraordinarily rapid. See e.g. Kupperman, 1961, The Chemical and Biological Actions of Radiation, M. Haissinsky Ed. Academic Press. Another major advantages of radiolysis is that it requires no additional chemical other than the water necessarily present in aqueous solution. Thus, it is possible to use a radiation source, such as $^{137}$Cs γ-rays to generate hydroxyl radical in a solution at a very precise rate. By integrating this rate of hydroxyl radical generation over time, the total equivalent concentration of hydroxyl radical generated in a solution can be precisely and accurately determined. This has the advantage of making carbon-centered radical mediated heavy hydrogen labeling experiments highly reproducible. In addition, for a given molecule of interest, a series of labeling experiments using varying total equivalent concentrations of hydroxyl radical can be performed in order to provide an additional dimension of information about the solvent accessibility of particular carbon atoms in a molecule of interest. If radiolysis is used to generate the hydrogen abstractor in the methods of the present invention, the solution should be supplemented with an electron scavenger source prior to exposing the solution to the radiation source. The electron scavenger source absorbs the damaging free electrons that are generated in the solution by the radiation source.

If $N_2O$ gas is used to remove a substantial amount of oxygen from the solution, then the $N_2O$ that dissolves into the solution as the $N_2O$ gas is bubbled into the solution serves as an excellent electron scavenger source. Therefore, in a preferred embodiment, the solution is saturated with $N_2O$ and the radiolysis experiments are performed under reductive anaerobic conditions, typically with 1.5 ml glass vials containing a screw cap and a Teflon-silicone septum. Each sample is irradiated using a $^{137}$Cs source to generated the desired total equivalent concentration of hydroxyl radical. Because the sample is saturated with $N_2O$, it is possible to precisely determine how long the sample must be exposed to $^{137}$Cs in order to generate the desired total equivalent concentration of hydroxyl radical. Using a $^{137}$Cs dose rate of 0.52 Gy s$^{-1}$ (Dosage$_{Rads/min}$) and the $G_{value}$ for hydroxyl radical in $N_2O$ saturated solutions (22 mM) of 5.6 10$^{-7}$ mol J$^{-1}$, the amount of time (time$_{min}$) that a given sample must be exposed to $^{137}$Cs in order to obtain the desired total equivalent concentration of hydroxyl radical ([OH radical]$_{mM}$) in the sample can be calculated using the relationship:

$$time_{min} = \frac{[OH\ radical]_{mM}}{Dosage_{Rads/min} \times G_{value} \times 1.04 \times 10^{-6}\ mM}$$

Using an internal reference to calibrate the labeling experiment. In a preferred embodiment, an internal reference is present during the labeling process. The internal reference serves to normalize the effective hydroxyl radical dose between successive labeling experiments. The internal reference is a molecule having reduced carbon atoms that readily exchanges with heavy hydrogen using the methods of the present invention. A preferred internal reference is leucine or norleucine. Specific embodiments of the present invention in which an internal reference is used are described in the examples section (Section 3). In particular, see Example 5.

Repeating the labeling reaction. In another preferred embodiment, the carbon-centered radical mediated heavy hydrogen labeling reaction is repeated a multiple number of times in succession on the same sample. Between each exchange reaction, additional reduced hydrogen donor is added to the sample solution to compensate for the hydrogen donor in the sample that is lost during the labeling reaction. Additionally, if the hydrogen atom abstractor is hydroxyl radical generated by radiolysis, additional amounts of electron scavenger source is added to the solution between exchange reactions to compensate for depletion of the electron scavenger source in the exchange reaction. In a preferred embodiment, this electron scavenger source is provided by bubbling the solution with $N_2O$ gas.

In a preferred embodiment, $O_2$ is removed from the solution by contacting the solution with a $N_2O$ gas, having less than about 20 parts per million $O_2$, until a concentration of $O_2$ dissolved in the solution when the hydrogen atom abstractor is generated is such that at least two percent of the corresponding carbon-centered radicals, formed by the reaction of the hydrogen atom abstractor with reduced carbon atoms in the molecule of interest, are repaired by donation of a hydrogen isotope by the heavy hydrogen donor. An illustrative $N_2O$ gas according to this embodiment is Semiconductor Grade 4.8 $N_2O$ gas containing less than 1 ppm $O_2$ (PraxAir, Cleveland, Ohio). In another preferred embodiment a positive pressure is maintained against the solution with a $N_2O$ gas, having less than 20 parts per million $O_2$ when the hydrogen atom abstractor is generated.

Another preferred embodiment comprises a method of labeling a reduced carbon atom in a peptide or protein with a heavy hydrogen, the method comprising:

(i) generating a total equivalent concentration of hydroxyl radical of at least about 10 μM in a solution that comprises a peptide or protein, an electron scavenger source, a heavy hydrogen source, and a heavy hydrogen donor;

(ii) adding an amount of a heavy hydrogen donor to the solution; and (iii) repeating steps (i) and (ii) until a cumulative total equivalent concentration of hydroxyl radical generated in the solution is, at a minimum, sufficient to produce a carbon-centered radical of the reduced carbon atom; wherein when the total equivalent concentration of hydroxyl radical is generated in step (i), the concentration of $O_2$ dissolved in the solution is such that at least five percent of the carbon-centered radicals formed in step (i) are repaired by donation of a hydrogen isotope by the heavy hydrogen donor. In a preferred aspect of this embodiment, the electron scavenger source is selected from the group consisting of solvated $N_2O$, ascorbate, tetranitromethane, nitrate, $CCl_4$, a thiol, a disulfide, a fluorinated aromatic, and a nitro aromatic. In another preferred aspect of this embodiment, the heavy hydrogen source in the solution is $D_2O$ present in the solution at a molar ratio to total solution of at least about 0.1 percent. In yet another preferred aspect of this embodiment, the heavy hydrogen donor is selected from the group consisting of a reduced water soluble thiol, $H_2S$, L-Ascorbic Acid, ($\pm$)-$\alpha$-tocopherol, a phenol, a water soluble phosphine, and a water soluble phosphite;

with the proviso that if the heavy hydrogen donor is a water soluble phosphine or water soluble phosphite, the heavy hydrogen donor contains a bond selected from the group consisting of P—H, P—D, and P—T.

In another preferred aspect of this embodiment, the total equivalent concentration of hydroxyl radical is generated by a method selected from the group consisting of exposing a light sensitive hydroperoxide to light, radiation, γ-rays, accelerated electrons, β-radiation, Fenton chemistry, $^{137}Cs$ radiolysis, $^{60}Co$ radiolysis, $^{32}PO_4$ radiolysis, Cu $K_\alpha$ radiation, molybdenum $K_\alpha$ radiation, synchrotron radiation, and neutron radiation.

Another preferred embodiment provides a method of labeling a reduced carbon atom in a peptide or protein with a deuterium, the method comprising generating a total equivalent concentration of hydroxyl radical of at least about 10 $\mu$M in an aqueous $N_2O$ saturated solution that includes at least about 50 picomoles of the peptide or protein, a molar ratio of $D_2O$ to total solution of at least 0.1 percent, and at least about 5 $\mu$M reduced dithiothreitol; wherein the hydrogen atom abstractor reacts with the reduced carbon atom in the peptide or protein to form a corresponding carbon-centered radical of the reduced carbon atom and the reduced dithiothreitol donates the deuterium to the carbon-centered radical thereby labeling the reduced carbon atom in the molecule of interest with the deuterium; with the proviso that when the total equivalent concentration of hydroxyl radical is generated, the solution has an $O_2$ concentration of less than about 6 $\mu$M. In a preferred aspect of this embodiment, the total equivalent concentration of hydroxyl radical is generated by a method selected from the group consisting of exposing ultraviolet light sensitive hydroperoxide to ultraviolet light, radiation, Fenton chemistry, $^{137}Cs$ radiolysis, $^{60}Co$ radiolysis, $^{32}PO_4$ radiolysis, Cu $K_\alpha$ radiation, molybdenum $K_\alpha$ radiation, synchrotron radiation, and neutron radiation. In a particularly preferred aspect of this embodiment, the total equivalent concentration of hydroxyl radical in generated by $^{137}Cs$ radiolysis.

In yet another preferred embodiment of the present invention, a method of labeling a reduced carbon atom in a peptide or protein with deuterium is provided. In this embodiment, the method comprises the steps of:

(i) irradiating an $N_2O$ saturated aqueous solution with a $^{137}Cs$ γ-ray source for a period of time sufficient to generate a total equivalent concentration of hydroxyl radical of at least about 10 $\mu$M, the solution comprising at least about 50 picomoles of the peptide or protein, a molar ratio of $D_2O$ to total solution of at least 0.1 percent, and at least about 5 $\mu$M reduced dithiothreitol;

(ii) adding an amount of reduced dithiothreitol to the solution;

(iii) contacting the solution with $N_2O$ gas, having less than 3000 parts per million $O_2$, for at least five minutes; and (iv) repeating steps (i) thru (iii) until a cumulative total equivalent concentration of hydroxyl radical of 10 $\mu$M to about 10 mM is generated in the $N_2O$ saturated aqueous solution.

In a particularly preferred embodiment, the molecule of interest is a protein or peptide that is labeled as described in any of the preceding embodiments or any of the methods detailed in the Claims. Subsequently, the molecule of interest is hydrolyzed into a plurality of amino acids after the hydrogen atom abstractor is generated. These hydrolyzed amino acids are purified, and an amount of deuterium associated with a carbon atom of a amino acid in said plurality of amino acids is quantified. By this approach, a labeled carbon atom in the molecule of interest is identified. In a preferred embodiment, an amount of heavy hydrogen associated with a carbon atom in an amino acid selected from the plurality of amino acids is determined by mass spectroscopy.

Determining the solvent accessible area of a peptide or protein. In yet another preferred embodiment, the molecule of interest is a peptide or protein. The exchange reaction isotopically and irreversibly labels particular solvent accessible side chains on the peptide or protein. The determination of the amino acid residues containing the isotopic label provides a means of assigning residues of proteins as solvent accessible and can be employed to study protein conformational changes and protein-protein interactions at the amino acid level. The formation of stable carbon-heavy hydrogen bond using carbon-hydrogen/heavy hydrogen exchange has the advantage over amide hydrogen/heavy hydrogen exchange of (1) producing highly stable carbon-heavy hydrogen label and (2) selectively targeting the heavy hydrogen label to solvent accessible side chains, rather than just amide backbones.

Figure 2:
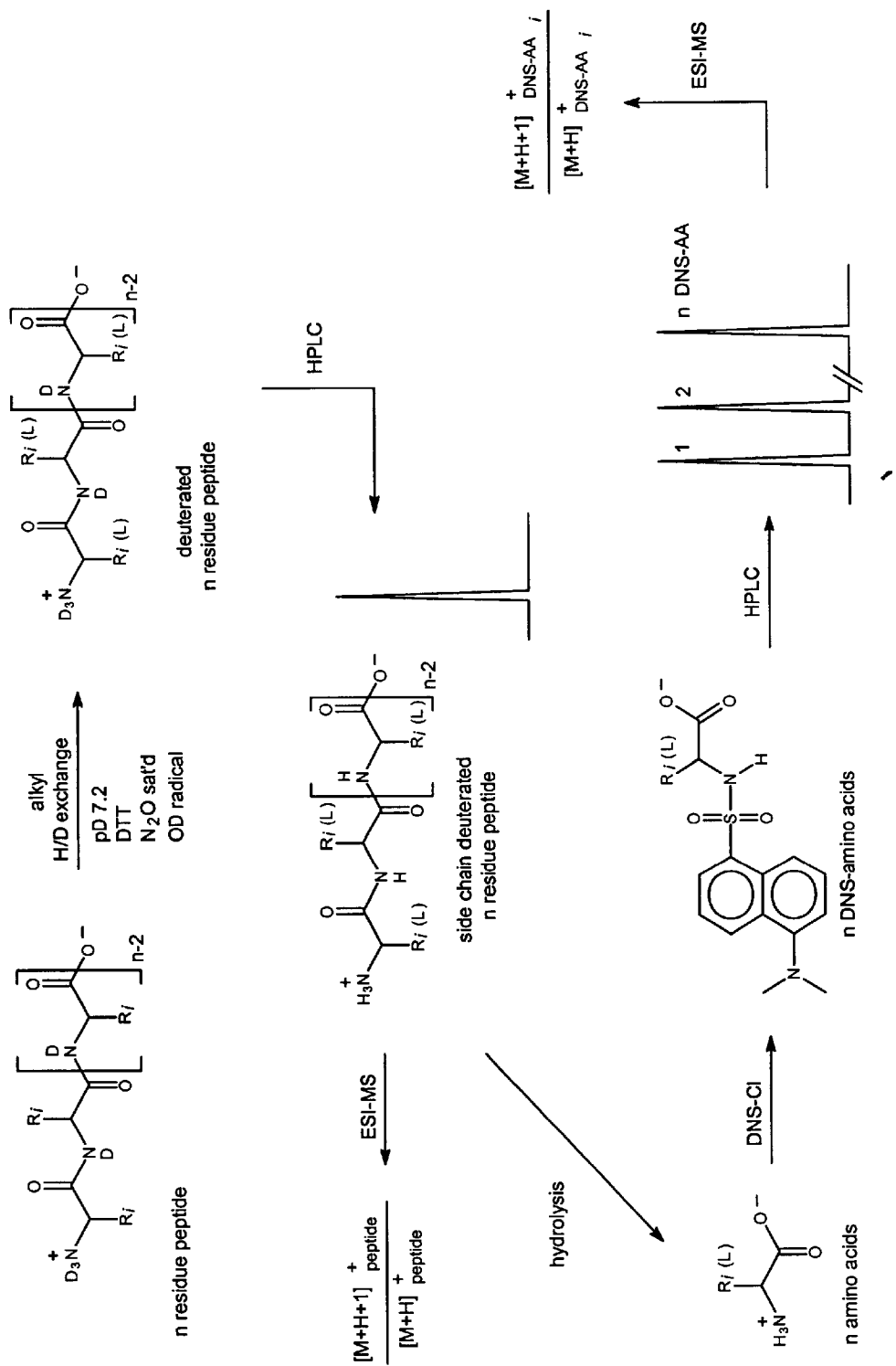
FIG. 2 is a schematic of a novel physico-chemical method that may be used to characterize amino acids residues that have been labeled according to the methods of the present invention. This novel method can be used to characterize amino acid residues involved in peptide-protein, protein-ligand, protein-inhibitor, or protein-protein interactions.

Application to Mapping Peptide Interactions. CTP (SEQ ID NO: 2) was used in Example 5 to examine alkyl $^1H/^2H$ exchange in peptides because the length of CTP (SEQ ID NO: 2) is representative of the size of peptides produced by tryptic digestion. In heavy hydrogen labeling of proteins, the amino acid residues susceptible to exchange cannot be assigned simply by employing protein hydrolysis with subsequent DNS-Cl derivatization, reversed-phase HPLC purification and ESI-MS analysis as shown in FIG. 2 because sequence information is completely lost and determination of solvent accessibility is difficult. Subjecting the protein to tryptic digestion allows for determination of heavy hydrogen exchange into the various peptides by examining the change in the mass centroid of peptide peaks present in the mass spectra obtained with a quadrupole mass analyzer using liquid chromatography-mass spectrometry (LC/MS). By identifying the peptides that exchanged, amino acid residues within the peptide can be analyzed as described in Example 5 to determine the extent of heavy hydrogen incorporation in the component amino acid residues and hence residue solvent accessibility. The LC/MS methods described herein can separate the DNS-amino acids by reversed-phase HPLC with online SIM acquisitions of each DNS-amino acid, thus permitting isotope ratio measurements to be measured concurrently with chromatographic separation. CTP (SEQ ID NO: 2) is a peptide fragment of the C-terminal portion of the third intracellular loop of the 5-hydroxytryptamine$_{2A}$ receptor which has been shown to bind to the G-protein, $G_{\alpha q}$. Receptor-G-protein coupling is an important area of research, however, precise details of interaction and activation are difficult to examine. Using LC/MS to (1) identify peptides containing $^2H$ from proteins subjected to heavy hydrogen labeling and (2) quantifying the extent of heavy hydrogen labeling in the component amino residues of those peptides greatly expedites sample analysis and enhances the amenability of the labeling reaction to study protein-protein interactions such as the interaction between CTP (SEQ ID NO: 2) and $G_{\alpha q}$.

3. EXAMPLES

The materials used in the following examples were obtained from commercial chemical sources and were used without further purification. Amino acids, as the free acid, were obtained from commercial sources. Methanol (HPLC and OPTIMA grade) and acetic acid (ACS reagent grade) were from Fisher Scientific. N,N-Diisopropylethylamine was purchased from Biosearch. $d_8$-DL-Valine was from Cambridge Isotope Laboratories. Dithiothreitol (DTT) was from Boehringer Mannheim. Dansyl chloride (DNS-Cl) was from Acros Organics/Fisher Scientific. Ammonium bicarbonate (Certified) and acetonitrile (HPLC grade) were from Fisher Scientific. Trifluoroacetic acid (1 ml sealed ampules) and iodoacetic acid (sodium salt, 99 % purity) were from Sigma. Acetic anhydride and tert-butylmethylether were from Aldrich. α-Bromo-2,3,4,5,6-pentafluorotoluene (pentafluorobenzylbromide) was purchased from Sigma-Aldrich. $D_2O$ (99.9 atom % D) was from Aldrich. $N_2O$ used was either Medipure™ U.S.P. grade containing 300 ppm $O_2$ or Semiconductor Grade 4.8 containing less than 1 ppm $O_2$ from PraxAir (Cleveland, Ohio). The He gas used was 99.995% pure and was obtained form PraxAir (Cleveland, Ohio). The peptide (Ala$^2$)-leucine enkephalin (YAGFL) (SEQ ID NO: 1) was obtained from BACHEM (King of Prussia, Pa.). The C-terminal peptide (SNEQKACKVLGI, abbreviated as CTP) (SEQ ID NO: 2) of the third intracellular loop of the 5-hydroxytryptamine$_{2A}$ receptor (obtained from Research Genetics) was a generous gift from Dr. Bryan L. Roth at Case Western Reserve University. CTP (SEQ ID NO: 2) was further purified by reversed-phase HPLC prior to $^1H/^2H$ exchange.

Example 1

Isotope Ratio Measurements of Amino Acids Using Gas Chromatography-mass Spectrometry Leucine Derivatization. N-acetyl-L-leucine NAL (1.8 mg, 10 μmol) was added to 10 ml of 0.23 M Na phosphate buffer, pH 6.9, to produce a stock solution of 1 mM NAL. From this stock solution, 1 ml of 578 μM NAL was prepared. HCl (600 μl of 1 M) was added to a 50 μl aliquot of 578 μM NAL. NAL was extracted three times with equal volumes of tert-butyl methyl ether. The organic extracts were pooled and evaporated under a stream of air. The NAL was esterified by the addition of 100 μl acetonitrile, 10 μl pentafluorobenzylbromide, and 10 μl N,N-diisopropylethylamine with heating at 45° C. for twenty minutes, which is a sufficient length of time to promote complete esterification of the NAL. The solvent was removed under a stream of air, and the remaining residue, N-acetyl-1-leucine-pentafluorobenzyl ester (NAL-PFB ester), was dissolved in 1 ml of methanol. This produced a 5 ng/μl NAL standard solution, assuming that the extraction and derivatization were quantitative. After mixing, this solution was immediately transferred to a screw top GC vial with an open cap and a Teflon/silicone septum. Less concentrated NAL-PFB ester solutions were made by dilutions from this stock.

GC-MS Instrumentation. The NAL standards were analyzed on an Extrel Benchmark gas chromatograph-mass spectrometer system. The system employed a Varian Star 3400 gas chromatograph with a septum-equipped programmable (SPI) injector and a Varian 8200 AutoSampler coupled via an Omega CN350 flexible interface to an Extrel Benchmark quadrupole mass spectrometer (formally Extrel, now ABB Extrel, Pittsburgh, Pa.) equipped with a 20 cm (4 mm inscribed radius) quadrupole mass filter with an m/z range of 0–2000. NAL-PFB ester standards (1.0 μl) were injected via the autosampler and separated on a SE-54 GC phase, 15 m×0.25 mm ID×0.25 μm film capillary column (Alltech). The He carrier gas had a volumetric flow rate of 1 mL/minute. The GC-MS interface was maintained at 285° C.

GC and Injector Temperature Gradients. The GC oven was programmed to increase in three intervals: from 120° C. to 170° C. at 30° C./min, from 170° C. to 192° C. at 5° C./min while the NAL-PFB ester eluted, and from 192° C. to 280° C. at 50° C./min. The oven was held at 280° C. in order to elute any remaining material. To increase the width of the peak to a greater extent, an injector program was developed. The initial injector temperature was 120° C. After injection the temperature was held for 1 minute, increased to 270° C. at a rate of 50° C./minute, and maintained at 270° C. for 5 minutes to purge the injector of any remaining material. While using the same column program, the injector program allows the peak width to be about 4 times wider with a retention time delay of approximately 1.5 min when compared to no injector program (injector at a constant temperature of 270° C.).

MS Settings: Calibration and Data Acquisition. The analysis of NAL-PFB ester was determined with electron capture-negative chemical ionization (EC-NCI) with methane as the ionizing gas at approximately 1 torr (exterior pressure 4×10$^{-4}$ torr) with an ion source temperature of 250° C. A filament voltage of 300 eV with an emission current of 6 mA was used. The data were collected using selected ion monitoring (SIM) with the following m/z values and scan times: 171.0 (5 ms), 172.0 (40 ms), 173.0 (40 ms), 174.0 (10 ms), and 175.0 (5 ms). After each 100 ms scan, a scan delay of two ms was applied. For each injection, data was collected for eight minutes. In an effort extend the filament lifetime, the emission filament was turned on one minute after the injection was made, to avoid the solvent spike, and turned off after the SIM acquisition. The instrument was calibrated using perfluorotributylamine and tuned to produce peak widths that lead to [M−H−1]$^-$ peaks of less than one percent in SIM.

Integration of Chromatographic Ion Peaks. The chromatographic peaks of molecular ions [M−H]$^-$ (172 m/z) and [M−H+1]$^-$ (173 m/z) were integrated using Extrel software (Extrel formerly, now ABB Extrel, Pittsburgh, Pa.) and corrected for background. The background corrected area values were used to calculate the isotope ratio, [M−H+1]$^-$/[M−H]$^-$, for each NAL-PFB ester injection.

Background Area Determination. In a region before each chromatographic ion peak, a region of approximately 600 scans was selected and used to determine the mean background (background/scan). This value was used to correct each integrated peak for background. The 172 and 173 background regions each were chosen to have the same starting and ending scan number.

Peak Area Determination. The starting and ending scan numbers used for peak integration were determined as follows. The more abundant m/z 172 chromatogram was used to determine the scan range for integration. In determining the starting scan number, the region just before the 172 peak begins its ascent is probed using a scan window of approximately 20 scans. Each probe produces an average background for this window. When this average background increases by one scan, the scan number just before this jump occurs becomes the starting scan number. In determining the ending scan number, the average background (determined with the 600 scans) is added to 0.02 times the maximum peak height (minus the average background) to get the intensity that marks two percent of the maximum. Approximately twenty scans are used as described above for the determination the starting scan number, except the peak is approached from the tailing side; the ending scan number is the scan number where the calculated average intensity at two percent of the maximum drops one scan. The scan window selection algorithm generated averages over 760 scans, and the same starting and ending scan numbers are used for integrating the 172 and 173 chromatographic ion peaks. It should be noted that the peak is being considered Gaussian in shape; however, in most instances tailing occurs, and this causes the peak shape to be skewed.

Example 2

Isotope Ratio Measurements of Amino Acids Using Electrospray Ionization-mass Spectrometry Amino Acid Standards. Standard solutions of 1.0 mg/ml of L-leucine, L-arginine, and L-proline were prepared by weight. The carrier solvent consisted of 1:1 (v:v) methanol: 2% acetic acid filtered and degassed with He. Standard dilutions of the amino acids were made with the same solvent.

Electrospray Optimization. The amino acid standards were analyzed on an Extrel Benchmark mass spectrometer equipped with a prototype electrospray interface (Extrel formerly, now ABB Extrel, Pittsburgh, Pa.) and a 20 cm (4 mm inscribed radius) quadrupole mass filter with an m/z range of 0–2000. A Pharmacia pump (Model P-500) provided a flow rate of 33 $\mu$l/min that was reduced to 2–3 $\mu$l/minute by an Alltech "T" flow splitter preceding the injection valve. The split ratio was controlled by an Alltech back pressure regulator on the waste line coming from the flow splitter. The injector (Rheodyne) was equipped with a 20 $\mu$l sample loop which permitted direct introduction of the entire sample to the electrospray interface. The electrospray needle (aluminum clad fused silica, SGE Inc.) was held at a potential between +2 to +3 kV. The dynode and multiplier voltages were 5000 V and 2000 V, respectively, while the nozzle voltage, position of the needle tip relative to the nozzle, and the flow rate were adjusted for optimal spraying as determined by the height of the $H_3O^+$ or $CH_3OH_2^+$ peaks with the pure solvent. The skimmer 1, skimmer 2, ion energy, extractor lens, ELFS lens, and exit lens were adjusted to optimize the intensity and width of the $H_3O^+$ or $CH_3OH_2^+$ peaks.

Mass Spectrometer Calibration and Data Acquisition. For the amino acid analyses the instrument was calibrated using an amino acid cocktail containing glycine, L-proline, L-leucine, L-glutamic acid, and L-arginine each at concentrations of 50–500 ng/$\mu$L in carrier solvent. During calibration the $[M+H]^+$ peaks were set to 76, 116, 132, 148 and 175, respectively. After calibration with the amino acid cocktail, a separate injection of the amino acid of interest was made, and the instrument adjusted to produce a peak width at half height of $\leq 0.5$ Thompson for the monoprotonated ion. This step was necessary since the peak shapes and intensities for the $[M+H]^+$ ions were different between the cocktail sample and a sample consisting of a single amino acid. The ability to obtain precise isotope ratios depended on optimal tuning for the amino acid to be measured. After these adjustments and prior to the acquisition of data for the isotope ratio determination, twenty $\mu$l of the amino acid sample was injected and data collected utilizing a profile acquisition from $[M+H-2]^+$ to $[M+H+4]^+$ at a step size of 1/16th of a Thompson with a scan delay of eight ms. The mass spectrum produced by this acquisition showed that the $[M+H]^+$ and $[M+H+1]^+$ ions are effectively baseline resolved and clearly demonstrated that the instrument can discriminate between ions at a one Thompson resolution with virtually no overlap of the $[M+H]^+$ and $[M+H+1]^+$ or $[M+H-1]^+$ ion peaks at their mass centers. For determining the isotope ratio, subsequent injections of twenty $\mu$l of the amino acid sample were made, and the data acquired using the selected ion monitoring (SIM) mode. The SIM program consisted of a one hundred ms scan (with an eight ms scan delay) of the following positive ions and their acquisition times: $[M+H-1]^+$ 5 ms, $[M+H]^+$ forty ms, $[M+H+1]^+$ forty ms, $[M+H+2]^+$ ten ms, and $[M+H+3]^+$ five ms.

Integration of the Selected Ion "Chromatograms." The intensities for each selected ion were averaged over identical time periods (scan numbers) that the ion current was effectively constant, defined as within 90% of the maximum intensity using the manufacturer's software. The $[M+H]^+$ chromatographic ion peak (SIM profile) was used to determine the starting and ending scan times. In an area before the peak a range of approximately 1 min was integrated, and from the resulting mass spectrum the average intensities per scan for the background for $[M+H]^+$ and $[M+H+1]^+$ ions were recorded. For determining the average intensity per scan for the $[M+H]^+$ and $[M+H+1]^+$ ions, a scan of 0.04 min (~20 scans) was taken with the peak maximum in the middle, and an average intensity per scan for the $[M+H]^+$ ion was obtained. This value was corrected for background by subtracting the background value of the average intensity per scan for the $[M+H]^+$ ion. The resulting value represented the maximum average intensity per scan in the absence of background.

In examining the SIM chromatographic ion profiles, the flat part was integrated of the peak since this part of the peak has the greatest signal to noise ratio. Thus, ninety percent of the background corrected average intensity per scan of the $[M+H]^+$ ion was used as the lower limit of integration. The background corrected average intensity per scan was multiplied by 0.90 and to this number was added the average intensity per scan for the background to produce the average intensity per scan that will be used to determine the starting and ending scan times for integration. The starting scan number was determined by probing the front of the peak using a window of 0.04 min (~20 scans). The starting time for integration was determined when the average intensity increased above the calculated value (e.g. 190000 to 190100 or approximately 0.1% of the calculated value). Since the jump may occur within the five scans that are in a 0.01 min time frame, the few extra scans were included in this time. The ending scan time was determined approaching the tailing side of the peak. After determining the starting and ending scan times, the mass spectrum for this time interval was produced and the average intensity per scan for $[M+H]^+$ and $[M+H+1]^+$ ions were recorded. This is a significant difference between the measurement of whole molecule isotope ratios by electrospray and by GC. The entire peak must be integrated when measuring isotope ratios by GC since the chromatographic separation routinely introduces isotopic separation.

The isotope ratio was determined by calculating the ratio of the background corrected average intensity per scan for the [M+H+1]+ ion divided by the background corrected average intensity per scan for the [M+H]+ ion as shown in the equation $$[M+H+1]^+/[M+H]^+ = ([M+H+1]^+_m - [M+H+1]^+_b)/([M+H]^+_m - [M+H]^+_b)$$

where m and b represent the measured and background average intensity per scan, respectively.

Amino Acid, DNS-Amino Acid, and Peptide Isotope Ratio Measurements Using ESI-MS. For all the $^1H/^2H$ exchange experiments conducted, the amount of $^2H$ incorporated into the amino acid, DNS-amino acid, or peptide was determined using electrospray ionization-mass spectrometry (ESI-MS) as previously described. For each reaction, the isotope ratio [M+H+1]+/[M+H]+ of the standard was determined prior to the $^1H/^2H$ exchange reaction sample. In experiments using $d_8$-DL-valine, the isotope ratio of [M+H-1]+/[M+H]+ was measured. Isotope ratio measurements of amino acids, DNS-amino acids, and YAGFL (SEQ ID NO: 1) were performed on an Extrel Benchmark mass spectrometer equipped with a prototype electrospray interface (ABB Extrel, formerly Extrel, Pittsburgh, Pa.) and a 20 cm (4 mm inscribed radius) quadrupole mass filter with an m/z range of 0–2000. Samples were dissolved in an appropriate amount of two percent acetic acid and diluted with an equal volume of methanol. Mass spectral analysis of carboxymethylated CTP (SEQ ID NO: 2) (cm-CTP) and the internal reference (as the DNS-Leu derivative) were performed on a Micromass Quattro II Triple Quadrupole Mass Spectrometer with m/z range of 0–4000. Samples were dissolved in an appropriate amount of 0.6% formic acid and diluted with an equal volume of acetonitrile. The SIM acquisitions used for isotope ratio measurements of the amino acids, DNS-amino acids, and YAGFL (SEQ ID NO: 1) consisted of a 1 second scan (with an 8 millisecond scan delay) of the following positive ions and their dwell times: [M+H-1]+ 50 ms, [M+H]+ 400 ms, [M+H+1]+ 400 ms, [M+H+2]+ 100 ms, and [M+H+3]+ 50 ms. The SIM acquisitions for cm-CTP and the internal reference DNS-Leu used a 100 ms dwell time for each ion.

Example 3

Isotope Ratio Measurements of Amino Acids Using Reversed-phase High Performance Liquid Chromatography-electrospray Ionization-mass Spectrometry Dansyl-Amino Acid Isotope Ratio Determination Using LC-MS. The LC-MS analysis was performed using a Vydac $C_{18}$ column (1.0×150 mm, 5 μ) and a Hewlett Packard Model 1100 liquid chromatograph equipped with an autosampler coupled to a Micromass Quattro II Triple Quadrupole Mass Spectrometer. In order to facilitate an accurate solvent gradient at a relatively low flow rate (usually between 25–35 μl/min) through the $C_{18}$ column, the solvent flow (150–200 μl/min) was split before the autoinjector using a stainless steel tee. An old $C_{18}$ column (2.1× 250 mm, 5 micron) fitted with a backpressure regulator (Upchurch scientific) was attached to the waste line. The sample line was introduced into a Vydac $C_{18}$ column (1.0× 150 mm, 5 micron) equipped with a micro $C_{18}$ guard column (Optimize Technologies). An imide-clad fused silica capillary (75 μm I.D.) was used to couple the column to the ESI interface. The sample flow rate was determined by measuring the flow out of this transfer capillary. Occasionally after sample analysis, the sample flow rate was reduced by about 15%. This flow rate was increased by adjusting the overall solvent flow controlled by the liquid chromatograph.

In an effort to eliminate potential contaminants that may be deleterious to LC-MS analysis, the DNS-amino acids were extracted prior to LC-MS analysis. The DNS-amino acids were extracted using three equal volumes of water saturated ethyl acetate, the extracts were pooled, and the ethyl acetate removed under a stream of dry $N_2$ gas. The remaining residue was stored at −20° C. until LC-MS analysis. On the day of analysis the sample was dissolved by adding an appropriate amount of Solvent A to achieve 30 μM DNS-amino acid concentration (based on the peak areas of the standard and irradiated purified peptides).

The reversed-phase HPLC method was as follows: solvent and gradient changes were made to facilitate LC-MS analysis for isotope ratio measurements of DNS-amino acids. Solvent A contained 1.0 mM $NH_4HCO_3$ in acetonitrile:$H_2O$ (5:95, v:v), and solvent B contained 1.0 mM $NH_4HCO_3$ in acetonitrile:$H_2O$ (90:10, v:v). The column was equilibrated for 20 min with 100% of solvent A. A volume of 10 μl of a 30 μM DNS-amino acid mixture was introduced by autoinjection. The gradient program consisted of a sequence of linear gradients: 35 min linear gradient from 0 to 20% of solvent B; 20 min linear gradient from 20 to 25% of solvent B; 25 min linear gradient from 25 to 82% of solvent B; 5 min linear gradient from 82 to 94% of solvent B. After the run, the column was washed for 20 min with 94% of solvent B, then re-equilibrated for 20 min with 100% of solvent A. The flow rate in the capillary was measured and adjusted, if necessary, by increasing the overall solvent flow rate. Usually, a 5 μl/min decrease in the sample flow rate required a 10–15 μl/min increase in the overall solvent flow rate to achieve the desired sample flow rate.

Example 4

$^1H/^2H$ Exchange Into Amino Acids $^1H/^2H$ Exchange in the Presence of DTT. The reductive anaerobic reaction in $D_2O$ contained 100 μM amino acid with DTT in the presence of various total equivalent concentrations of hydroxyl radical in 100 mM Li phosphate pD 7.2 (pD=pH meter reading in $D_2O$+0.4; at room temperature (20–25° C.). The solutions were treated prior to radiolysis with either (i) $N_2O$ for 30 minutes or (ii) Ar for 30 minutes then bubbled with $N_2O$ for 5 minutes. The $^2H/^1H$ exchange reaction of $d_8$-DL-valine was in phosphate buffered $H_2O$ (pH 6.8).

$^1H/^2H$ Exchange in the Presence of Ascorbic Acid Exchange experiments using radiolysis with L-ascorbic acid as the deuterium atom donor were performed in a similar manner as described for DTT.

Example 5

$^1H/^2H$ Exchange Into Peptides

In this example, various embodiments of the method, according to FIG. 2, are illustrated and representative experimental results are presented.

$^1H/^2H$ Exchange into YAGFL (SEQ ID NO: 1) and the Corresponding Free Amino Acids in the Presence of DTT. Exchange reactions involving YAGFL (SEQ ID NO: 1) and the corresponding free amino acids (irradiated simultaneously in separate vials) were similar to those described for amino acids (Example 4). The reductive anaerobic reaction in $D_2O$ contained 100 μM amino acid, 33 μM DTT, and a total equivalent concentration of hydroxyl radical of 50 μM in 10 mM phosphate buffer pD 7.2 at room temperature (20–25° C.). Each solution was gassed for 30 minutes with $N_2O$ and irradiated within 30 minutes. Radiolysis was performed using a $^{137}Cs$ source for a specified period of time. Two sets of experiments were conducted. One set of reactions contained a total reaction volume of 1.75 ml using Li phosphate buffer. The peptide and amino acids were desalted using cation-exchange chromatography. The other set contained a total volume of 1.0 ml containing Na phosphate buffer. The peptide was purified by reversed-phase HPLC, in the manner described in Example 8 for peptides, and amino acids were derivatized with DNS-Cl, in the manner described in Example 10, and then extracted.

$^1H/^2H$ Exchange into YAGFL (SEQ ID NO: 1) at Various Total OH Radical Concentrations. The $^1H/^2H$ exchange reaction conditions described in Example 4 were used several times in succession, concomitant with reduced DTT and $N_2O$ addition, to facilitate $^1H/^2H$ exchange into YAGFL (SEQ ID NO: 1). Each reaction (1.75 ml) contained 100 μM YAGFL (SEQ ID NO: 1), 29 μM DTT, and a total equivalent concentration of hydroxyl radical of 0.050 to 1.6 mM in 10 mM phosphate buffer (pD 7.2) at room temperature (20–25° C.). Each solution was gassed for 30 minutes with $N_2O$ and irradiated within 30 minutes. Each sample was exposed to a total equivalent concentration of hydroxyl radical of 0.050 mM, then forty percent of the original amount of reduced DTT present (20 nM) was added to the reaction and the sample gassed for 10 minutes with $N_2O$. The samples were then exposed to another total equivalent concentration of hydroxyl radical of 0.050 mM. This process was repeated until the desired cumulative total equivalent concentration of hydroxyl radical generated was achieved. The sample exposed to a cumulative total equivalent concentration of hydroxyl radical of 1.6 mM was the exception: the last exposure was a total concentration of hydroxyl radical of 0.80 mM.

$^1H/^2H$ Exchange into CTP (SEQ ID NO: 2). The $^1H/^2H$ exchange reaction with CTP (SEQ ID NO: 2) was performed in a similar manner as conducted with YAGFL (SEQ ID NO: 1). The reaction (0.5 ml) contained 100 μM CTP, 20 μM leucine, 25 μM DTT, and a total equivalent concentration of hydroxyl radical of 0.40 mM in 10 mM phosphate buffer (pD 7.2) at room temperature (20–25° C.). Leucine served as an internal reference to normalize the hydroxyl radical doses. A cumulative total equivalent concentration of hydroxyl radical of 0.40 mM was achieved by successive exposures, in which each exposure generated a total equivalent concentration of hydroxyl radical of 0.050 mM. After each successive exposure, DTT and $N_2O$ were added to the sample as described above for YAGFL (SEQ ID NO: 1). Isolation of leucine from the reaction mixture was achieved by removing an aliquot equivalent to 1 nM of leucine, derivatizing it with DNS-Cl, in the manner described in Example 6, and then purifying the DNS-Leu by reversed-phase HPLC, in the manner described for peptides in Example 8. The remaining CTP (SEQ ID NO: 2) was carboxymethylated, in the manner described in Example 10, and then purified by reversed-phase HPLC in the manner described for peptides in Example 8.

Work up. The quantitation of the sulfhydryl groups of DTT and the CTP (SEQ ID NO: 2) was performed using the DTNB assay described in Example 9. In addition, the quantization of amines was performed with the TNBS assay described in Example 9. Peptide hydrolysis was as described in Example 8. Amino acid derivatization using DNS-Cl was as described in Example 10. Extraction of DNS-amino acids and Reverse-Phase HPLC purification of DNS-amino acids was as described in Example 8.

Isotope Ratio Measurements Using ESI-MS. For all the $^1H/^2H$ exchange experiments conducted in Example 5, the amount of $^2H$ incorporated into the amino acid or peptide was determined using electrospray ionization-mass spectrometry (ESI-MS). For each reaction, the isotope ratio $[M+H+1]^+/[M+H]^+$ of the standard was determined prior to the $^1H/^2H$ exchange reaction sample. Isotope ratio measurements of amino acids, DNS-amino acids, and YAGFL (SEQ ID NO: 1) were performed on an Extrel Benchmark mass spectrometer equipped with a prototype electrospray interface (ABB Extrel, formerly Extrel, Pittsburgh, Pa.) and a 20 cm (4 mm inscribed radius) quadrupole mass filter with an m/z range of 0–2000. Samples were dissolved in an appropriate amount of 2% acetic acid and diluted with an equal volume of methanol. Mass spectral analysis of carboxymethylated CTP (SEQ ID NO: 2) (cm-CTP) and the internal reference (as the DNS-Leu derivative) were performed on a Micromass Quattro II Triple Quadrupole Mass Spectrometer with m/z range of 0–4000. Samples were dissolved in an appropriate amount of 0.6% formic acid and diluted with an equal volume of acetonitrile. The SIM acquisitions used for isotope ratio measurements of the amino acids, DNS-amino acids, and YAGFL consisted of a one second scan (with an eight millisecond scan delay) of the following positive ions and their dwell times: $[M+H-1]^+$ 50 ms, $[M+H]^+$ 400 ms, $[M+H+1]^+$ 400 ms, $[M+H+2]^+$ 100 $[M+H+3]^+$ 50 ms. The SIM acquisitions for cm-CTP (SEQ ID NO: 2) and the internal reference DNS-Leu used a 100 ms dwell time for each ion. The extent of $^1H/^2H$ exchange was calculated as described in Example 11.

$^1H/^2H$ Exchange into YAGFL (SEQ ID NO: 1) and its Constitutive 3S Amino Acids in the Presence of DTT. The isotope ratios of each amino acid standard and irradiated sample were determined using ESI-MS and appear in Table 5-1. The isotope ratios presented in Table 5-2 are for the DNS-amino acids. The DNS-amino acids were derivatized after the free amino acids were subjected to $^1H/^2H$ exchange. Thus, Tables 5-1 and 5-2 are two parallel $^1H/^2H$ exchange experiments with $^2H$ incorporation determined by ESI-MS of free and DNS-amino acids, respectively.

TABLE 5-1

Hydroxyl Radical Induced Hydrogen/Deuterium Exchange into Amino Acids Tyr, Ala, Gly, Phe, and Leu: Free Amino Acid Isotope Ratio Measurements.

| Amino Acid[a] (μM) | DTT[a] (μM) | Total Equivalent Concentration of Hydroxyl Radical Generated (μM) | Mean Isotope Ratio ± Standard Deviation (n[b]) | Efficiency[c] (%) |
|---|---|---|---|---|
| 50 μM l-Tyr standard[d] 100 (155) | 33 (20) | 50 | 0.291 ± 0.024 (3) | n.d.[e] |
| 50 μM l-Ala standard 100 (121) | 33 (18) | 50 | 0.0434 ± 0.0011 (4) 0.0461 ± 0.0017 (4) | 0 |
| 50 μM Gly standard 100 (108) | 33 (18) | 50 | 0.0351 ± 0.0019 (3) 0.0338 ± 0.0014 (4) | 0 |
| 50 μM l-Phe standard 100 (116) | 33 (20) | 50 | 0.117 ± 0.002 (5) 0.101 ± 0.003 (4) | 0 |

TABLE 5-1-continued

Hydroxyl Radical Induced Hydrogen/Deuterium Exchange into Amino Acids Tyr, Ala, Gly, Phe, and Leu: Free Amino Acid Isotope Ratio Measurements.

| Amino Acid[a] ($\mu$M) | DTT[a] ($\mu$M) | Total Equivalent Concentration of Hydroxyl Radical Generated ($\mu$M) | Mean Isotope Ratio ± Standard Deviation (n[b]) | Efficiency[c] (%) |
|---|---|---|---|---|
| 100 $\mu$M l-Leu standard 100 (89) | 33 (18) | 50 | 0.0816 ± 0.0006 (4) 0.192 ± 0.006 (4) | 22 |

[a]The value in parentheses is the amount of amino acid or DTT remaining after radiolysis.
[b]The number of consecutive injections used in the ESI-MS analysis.
[c]The efficiency was calculated as described in Example 11.
[d]The isotope ratio for each standard was determined prior to the $^1H/^2H$ exchange sample.

TABLE 5-2

Hydroxyl Radical Induced Hydrogen/Deuterium Exchange into Amino Acids Tyr, Ala, Gly, Phe, and Leu: Dansyl Amino Acid Isotope Ratio Measurements.

| Dansyl Amino Acid[a] ($\mu$M) | DTT[a] ($\mu$M) | Total Equivalent Concentration of Hydroxyl Radical Generated ($\mu$M) | Mean Isotope Ratio ± Standard Deviation (n[b]) | Efficiency[c] (%) |
|---|---|---|---|---|
| 100 $\mu$M DNS-Tyr standard[d] 100 (150) | 33 (20) | 50 | 0.278 ± 0.003 (4) 0.387 ± 0.009 (4) | 22 |
| 50 $\mu$M DNS-Ala standard 100 (112) | 33 (17) | 50 | 0.209 ± 0.001 (4) 0.207 ± 0.004 (4) | 0 |
| 50 $\mu$M DNS-Gly standard 100 (112) | 33 (17) | 50 | 0.196 ± 0.001 (4) 0.187 ± 0.002 (4) | 0 |
| 50 $\mu$M DNS-Phe standard 100 (116) | 33 (20) | 50 | 0.277 ± 0.001 (4) 0.266 ± 0.002 (4) | 0 |
| 100 $\mu$M DNS-Leu standard 100 (103) | 33 (17) | 50 | 0.242 ± 0.004 (4) 0.356 ± 0.008 (4) | 23 |

[a]The value in parentheses is the amount of amino acid or DTT remaining after radiolysis.
[b]The number of consecutive injections used in the ESI-MS analysis.
[c]The efficiency was calculated as described in Example 11.
[d]The isotope ratio for each standard was determined prior to the $^1H/^2H$ exchange sample.
[e]The isotope ratio was not determined because of high [M + H + 1] background ion current.

The YAGFL (SEQ ID NO: 1) peptide was subjected to a series of $^1H/^2H$ exchange reactions at various total equivalent concentrations of hydroxyl radical. After the $^1H/^2H$ exchange reactions were complete, the peptides were purified using reversed-phase HPLC. The isotope ratios of the YAGFL (SEQ ID NO: 1) standard and $^1H/^2H$ exchange samples appear in Table 5-3.

TABLE 5-3

Hydroxyl Radical Induced Hydrogen/Deuterium Exchange into YAGFL.(SEQ ID NO: 1)

| YAGFL[a] (SEQ ID NO: 1) (mM) | DTT (mM) | Total Equivalent Concentration of Hydroxyl Radical Generated (mM) | Mean Isotope Ratio ± Standard Deviation (n[b]) | Efficiency[c] (%) |
|---|---|---|---|---|
| 50 mM standard[d] | | | 0.344 ± 0.001 (3) | |
| 100 (100) D % $^2H$[e] | 29 | 0.050 | 0.403 ± 0.002 (3) 5.9 | 12 |
| 100 (117) D % $^2H$ | 29 | 0.10 | 0.456 ± 0.004 (3) 11.2 | 11 |
| 100 (130) D % $^2H$ | 29 | 0.20 | 0.542 ± 0.003 (3) 19.8 | 9.9 |
| 100 (122) D % $^2H$ | 29 | 0.40 | 0.692 ± 0.011 (3) 34.8 | 8.7 |
| 100 (83) D % $^2H$ | 29 | 0.80 | 0.878 ± 0.006 (3) 53.4 | 6.7 |
| 100 (61) D % $^2H$ | 29 | 1.6 | 1.00 ± 0.05 (3) 65.6 | 4.1 |

[a]The value in parentheses is the amount of peptide remaining after radiolysis.
[b]The number of consecutive injections used in the ESI-MS analysis.
[c]The efficiency was calculated as described in Example 11.
[d]The isotope ratio for each standard was determined prior to the $^1H/^2H$ exchange sample.
[e]Δ % $^2H$ was calculated as described in Example 11.

$^1H/^2H$ Exchange into YAGFL (SEQ ID NO: 1): Isotope Ratio Determination of Amino Acid Residues. After determining the YAGFL (SEQ ID NO: 1) peptide isotope ratio, the remaining material (approximately 50 nmol) was used to determine the extent of $^1H/^2H$ exchange into each amino acid residue. The peptide was hydrolyzed into its constitutive amino acids, the amino acids were derivatized with DNS-Cl, and the DNS-amino acids separated using reversed-phase HPLC. The isotope ratios of each DNS-amino acid standard and $^1H/^2H$ exchange residue were determined by ESI-MS and are presented in Table 5-4.

TABLE 5-4

Isotope Ratio Measurements of DNS-Amino Acid Residues of YAGFL (SEQ ID NO: 1) Subjected to Alkyl $^1H/^2H$ Exchange. Mean Isotope Ratio ± Standard Deviation (n[a])

| Total Equivalent Concentration of Hydroxyl Radical Generated ($\mu$M) | DNS-Tyr | DNS-Ala | DNS-Gly | DNS-Phe | DNS-Leu |
|---|---|---|---|---|---|
| 0[b] | 0.268 ± 0.002 (4) | 0.201 ± 0.002 (3) | 0.181 ± 0.004 (3) | 0.254 ± 0.001 (3) | 0.220 ± 0.005 (4) |
| 0.050 D % $^2H$[c] | 0.281 ± 0.003 (3) 1.3 | 0.205 ± 0.007 (3) 0 | 0.188 ± 0.003 (2) 0 | 0.256 ± 0.002 (3) 0 | 0.270 ± 0.007 (3) 5.0 |
| 0.10 D % $^2H$ | 0.300 ± 0.004 (3) 3.2 | 0.206 ± 0.005 (3) 0 | 0.177 ± 0.003 (3) 0 | 0.250 ± 0.006 (3) 0 | 0.315 ± 0.015 (3) 9.5 |
| 0.20 | 0.308 ± 0.005 (4) | 0.215 ± 0.006 (3) | 0.181 ± 0.004 (3) | 0.261 ± 0.002 (3) | 0.397 ± 0.028 (3) |

TABLE 5-4-continued

Isotope Ratio Measurements of DNS-Amino Acid
Residues of YAGFL (SEQ ID NO: 1) Subjected to Alkyl $^1$H/$^2$H Exchange.
Mean Isotope Ratio ± Standard Deviation (n[a])

| Total Equivalent Concentration of Hydroxyl Radical Generated ($\mu$M) | DNS-Tyr | DNS-Ala | DNS-Gly | DNS-Phe | DNS-Leu |
|---|---|---|---|---|---|
| D % $^2$H 0.40 | 4.0 0.336 ± 0.009 (2) | 1.4 0.224 ± 0.004 (4) | 0 0.199 ± 0.004 (3) | 0.7 0.259 ± 0.001 (3) | 17.7 0.496 ± 0.011 (3) |
| D % $^2$H | 6.8 | 2.3 | 1.8 | 0.5 | 27.6 |

[a]The number of consecutive injections used in the ESI-MS analysis.
[b]The isotope ratio for each standard was determined prior to the $^1$H/$^2$H exchange sample.
[c]D % $^2$H was calculated as described in Example 11.
Differences not statistically significant were assigned zero.

$^1$H/$^2$H Exchange into CTP (SEQ ID NO: 2). The CTP (SEQ ID NO: 2) was subjected to the $^1$H/$^2$H exchange reaction in which a total equivalent concentration of hydroxyl radical generated was 0.40 mM. The labeling reaction was done in presence of leucine, which served as an internal reference. After the $^1$H/$^2$H exchange reaction, the peptide was carboxymethylated, purified using reversed-phase HPLC, then analyzed by ESI-MS. The relative intensity of each ion monitored during the SIM acquisition of the cm-CTP (SEQ ID NO: 2) standard and $^1$H/$^2$H exchange sample were determined and appear in Table 5-5. The internal reference leucine was converted into DNS-Leu, purified by reversed-phase HPLC, then analyzed by ESI-MS. The relative intensity of each ion monitored during the SIM acquisition is shown in Table 5-5.

TABLE 5-5

Hydroxyl Radical Induced Hydrogen/Deuterium Exchange into the C-Terminal Peptide (SEQ ID NO: 2) in the Presence of the Internal Reference Leucine.

| Compound | Relative Intensity[a] (%) | | | | % $^2$H[b] |
|---|---|---|---|---|---|
| | [M + H]$^+$ | [M + H + 1]$^+$ | [M + H + 2]$^+$ | [M + H + 3]$^+$ | |
| Standard[c] | | | | | |
| DNS-Leu | 71.7 | 16.2 | 9.8 | 2.4 | |
| cm-CTP (SEQ ID NO: 2) | 40.9 | 31.0 | 17.8 | 10.3 | |
| $^1$H/$^2$H Exchange | | | | | |
| DNS-Leu | 52.1 | 31.6 | 12.5 | 3.8 | 25.0 |
| cm-CTP (SEQ ID NO: 2) | 25.0 | 27.6 | 25.4 | 22.0 | 67.5 |

[a]The relative intensity (%) was calculated as described in Example 11.
[b]% $^2$H was calculated as described in Example 11.
[c]The isotope ratio for each standard was determined prior to the $^1$H/$^2$H exchange sample.

$^1$H/$^2$H Exchange into C—H Bonds of Peptides. A method was developed to improve methods for carbon-centered radical mediated heavy hydrogen labeling of peptides while minimizing peptide decomposition and to determine the extent of $^2$H incorporation within each residue of a peptide by measuring the isotope ratio using ESI-MS. $^1$H/$^2$H exchange into various peptides was facilitating by exposing the peptide to additional radiolytic doses that were each sufficient to generate a total equivalent concentration of hydroxyl radical of 50 $\mu$M. Reduced DTT was added to the solution after each radiolytic exposure. Based on previous studies with the amino acids it was determined that ~40% of the reduced DTT is oxidized after a radiolytic exposure that is capable of generating a total equivalent concentration of hydroxyl radical of 50 $\mu$M, so the amount of reduced DTT added was 40% of the amount present prior to radiolysis (Table 5-3).

Using this method YAGFL (SEQ ID NO: 1) was exposed to varying concentrations of hydroxyl radical (Table 5-3). Each exposure resulted in larger isotope ratios of the peptide. However, based on the reversed-phase HPLC chromatographs at 220 nm, the amount of peptide remaining after each hydroxyl radical dosage was diminished. At 400 mM total equivalent concentration of hydroxyl radical, the peptide was decomposed by ~40%, and at 800 mM and 1.6 mM the amount of unoxidized peptide was significantly less. This decomposition could be the result of peptide oxidation, resulting from $O_2$ introduction by gassing with $N_2O$ (containing 300 ppm $O_2$). As described herein, decreased oxidation of peptides has been achieved by employing semiconductor grade $N_2O$ and maintaining a positive $N_2O$ pressure with a balloon.

Quantitation of $^1$H/$^2$H Exchange into the Individual Residues of a Peptide. Increase in the isotope ratio of YAGFL (SEQ ID NO: 1) was observed for the peptide following the $^1$H/$^2$H exchange protocol (Table 5-3). These data indicate that $^2$H is being exchanged into the peptide, but do not provide information on the residue(s) involved in exchange. Tandem mass spectrometry can be used in a limited fashion to examine isotope incorporation, but it is not the method of choice. Rather then use tandem mass spectroscopy, the peptide was chemically hydrolyzed into its amino acid constituents and separated from the hydrolysate. If the hydrolysate is desalted using cation-exchange chromatography, the sample will contain a mixture of amino acids. Because the sample is ionized by electrospray, measuring the isotope ratio of each amino acid in this mixture would require approximately five times the amount of each amino acid than if the amino acid were analyzed separately, assuming equally diminished ionization efficiencies. In this case, more material would be necessary because each amino acid SIM acquisition would require one injection of the entire sample when using direct flow injection analysis. A SIM acquisition could be programmed to monitor all [M+H]$^+$ and [M+H+1]$^+$ ions in the mixture. However, the number of data points for each isotope ratio would be diminished and contribute to the error in measurement. In addition, the peptide may contain different amino acids that are within m/z values that interfere in isotope ratio determination, e.g., Glu (148.1 Th), and Lys (147.2 Th), and would require separation prior to isotope ratio measurements. To circumvent these problems, the amino acids were derivatized in the hydrolysate, separated, and analyzed using ESI-MS.

A variety of reagents can be use to derivatize amino acids. DNS-Cl was chosen for several reasons. First, dansylation results in a 233 Thompson increase in the amino acid [M+H]$^+$ ion, a change in mass that permits formation of the monoprotonated ion under the conditions used for ESI-MS isotope ratio measurements and improves the signal to noise ratio of the [M+H]$^+$ ion while retaining the unit mass resolution necessary for accurate isotope ratio determination. This advantage is experimentally demonstrated when comparing the data presented in Tables 5-1 and 5-2. The isotope ratio of the free amino acid tyrosine in Table 5-1 could not be determined because of the high background ion current overlapping the tyrosine $[M+H+1]^+$ ion. When this background was subtracted from the $[M+H+1]^+$ ion current of tyrosine, the resulting average intensity per scan was too low, and an accurate isotope ratio determination was not possible. This could be circumvented by using more material in the analysis, but this would reduce the utility of the method for studying alkyl $^1H/^2H$ exchange on complexes in which only small amounts of material are available. The ratios in Table 5-1 and Table 5-2 were calculated from a mass spectrometer equipped with a prototype ESI interface having a lower ionization efficiency than more sophisticated designs now commercially available. The shift in m/z for the $[M+H]^+$ ion from 182.2 m/z (Tyr) to 415.2 m/z (DNS-Tyr) permitted an isotope ratio determination with the prototype ESI interface. In addition the data in Tables 5-1 and 5-2 show that isotope ratio determination of the free amino acids and DNS-amino acids are comparable, indicating that converting the amino acids to their dansyl counterparts did not compromise isotope ratio measurements.

Another benefit of using DNS-Cl is that the DNS-amino acids can be purified by reversed-phase HPLC and the effluent monitored by UV absorbance or fluorescence. Various methods are available for HPLC separation of DNS-amino acids, but what is preferred are methods that separate all possible DNS-amino acids using a volatile buffer, in order to facilitate ESI-MS analysis.

One drawback in the developed method (FIG. 2) becomes apparent when the peptide contains two or more residues of the same amino acid. If the corresponding DNS-amino acid is determined by ESI-MS not to contain $^2H$, there is no problem. However, if the data indicate significant alkyl $^1H/^2H$ exchange occurred, the extent of reaction with each residue will be ambiguous. If the distinction is important two possible solutions exist. First selectively cleaving the peptide between the two residues and separating the product peptides prior to hydrolysis. The second alternative is to subject the peptide to Edman degradation with separate isolation of each of the phenylthiohydantoin (PTH) amino acids.

After determining that the peptide was isotopically labeled (Table 5-3), the remaining material (approximately 50 nmol) was hydrolyzed, derivatized with DNS-Cl, and the isotope ratio of each DNS-amino acid determined by ESI-MS (Table 5-4). The resulting isotope ratios for DNS-Leu indicate that a substantial amount of the $^2H$ incorporated within the peptide is contained within the side chain of this residue. At a total equivalent concentration of hydroxyl radical of 50 $\mu M$, $^1H/^2H$ exchange occurs in leucine and to a lesser extent tyrosine. The isotope ratios produced for the free amino acids irradiated separately (Table 5-2) indicate that tyrosine is the only residue, other than leucine, prone to a measurable amount of alkyl $^1H/^2H$ exchange at a total equivalent concentration of hydroxyl radical of 50 $\mu M$. As the total equivalent concentration of hydroxyl radical is increased (in 50 $\mu M$ increments and concomitant with DTT and $N_2O$ addition) the other residues undergo enough exchange so that the $^1H/^2H$ exchange becomes detectable.

When examining the overall $^1H/^2H$ exchange into the peptide and its residues, it is important to note that the isotope ratio of YAGFL (SEQ ID NO: 1) reported in Table 5-3 was for the $[M+H+1]^+/[M+H]^+$ ratio. Hence, the contributions of isotopically labeling the M+1 species (~23% of the peptide sample prior to alkyl $^1H/^2H$ exchange32) and M+2 species (~5% of the peptide sample) of the peptide were not accounted for, resulting in an underestimate of the total $^2H$ incorporation. In the SIM acquisition, the majority of the scanning time was spent on the $[M+H]^+$ and $[M+H+1]^+$ ions (400 ms each) and not the $[M+H+2]^+$ and $[M+H+3]^+$ ions (100 ms and 50 ms, respectively), thus only the isotope ratio of $[M+H+1]^+/[M+H]^+$ was reported. Thus, the sum of the D % $^2H$ values for each residue in Table 5-4 is greater than the D % $^2H$ value for the corresponding peptide in Table 5-3. By examining the isotope ratio of each residue as the DNS-amino acid derivative it has been demonstrated that residues of a peptide are capable of being labeled using the developed alkyl $^1H/^2H$ exchange methodology. Table 5-4 shows that the susceptibility of the amino acid residues of YAGFL (SEQ ID NO: 1) toward alkyl $^1H/^2H$ exchange is L>Y>A~F>G, in order of decreasing reactivity. This trend in reactivity for the alkyl amino acids corresponds to the second order rate constants for reaction of hydroxyl radical with the N-glycyl derivatives. The ratio of $^1H/^2H$ exchange being 15:1.3:1 (based on the $[M+H+1]^+/[M+H]^+$ isotope ratio, using a total equivalent concentration of hydroxyl radical of 400 mM, with the ratio of rate constants being 19:1.4:134. The faster reaction with hydroxyl radical observed for leucine is presumably due to the presence of secondary and tertiary carbons on the side chain. The greater stability of the generated secondary and tertiary carbon-centered radicals, as compared to primary carbon-centered radicals, facilitate the $^2H$ donation by DTT, resulting in the observed isotope ratio.

Reaction of Hydroxyl Radical with Aromatic Amino Acids. The aromatic residues tyrosine and phenylalanine behave in a quite different manner than the aliphatic residues. Radiolysis of tyrosine and phenylalanine under aerobic conditions results in ring hydroxylation, and radiolysis of YAGFL (SEQ ID NO: 1) under aerobic conditions results largely in hydroxylation of the phenylalanine residue. However, under the anaerobic conditions used in these $^1H/^2H$ exchange reactions (Table 5-2), tyrosine exhibited $^1H/^2H$ exchange but phenylalanine did not. The diminished $^1H/^2H$ exchange efficiency of phenylalanine relative to tyrosine was also observed in YAGFL (SEQ ID NO: 1) (Table 5-4). Radiolysis studies indicate that the hydroxyl radical reacts preferentially with tyrosine. Phenylalanine and tyrosine share two potential mechanisms of undergoing $^1H/^2H$ exchange: abstraction of the a-H or the benzylic b-Hs, resulting in exchange similar to that observed in the alkyl amino acids. Addition of the hydroxyl radical to the aromatic ring as the first step in hydroxylation could result in exchange if the reductive conditions of the exchange reaction result in formation of a 1-hydroxy-[6-$^2H$] cyclohexadiene which rearomatizes by dehydration. Tyrosine could undergo $^1H/^2H$ exchange via two reactions of the tyrosyl radical: either $^2H$-atom donation to the ortho position followed by enolization to regenerate tyrosine or by $1e^-$ oxidation to the quinone methide and subsequent $2e^-$ reduction back to tyrosine. These pathways are precedented by the trapping of the phenoxyl radical by spin traps at the ortho carbon and the observed $1e^-$ oxidation of alkyl phenoxyl radicals to quinone methides. Because of the much greater $^1H/^2H$ exchange observed with tyrosine, it suggests that at least one of the tyrosine specific pathways is contributing to the observed exchange.

$^1H/^2H$ Exchange into a Peptide in the Presence of an Internal Reference. The $^1H/^2H$ exchange reaction was applied to a 12 residue peptide (SNEQKACKVLGI) (SEQ ID NO: 2), the C-terminal peptide (CTP) of the third intracellular loop of the 5-hydroxytiyptamine$_{2A}$ receptor, in the presence of leucine as an internal reference. Alkyl $^1H/^2H$ Exchange was shown to occur in both molecules and is clearly demonstrated by the method and is summarized in Table 5-5. For the monoprotonated form of cm-CTP (SEQ ID NO: 2), the most abundant ion shifted from [M+H]$^+$ (before exchange) to [M+H+1]$^+$ (after exchange), and the incorporation was 68 atom percent excess $^2$H. In fact a shift towards higher m/z for all ions in the monoprotonated isotopic envelope is observed as a result of $^1$H/$^2$H exchange. For DNS-Leu the most abundant ion remained the [M+H]$^+$ species, and the $^1$H/$^2$H exchange generated a 25 atom percent excess $^2$H. Since the extent of $^1$H/$^2$H exchange has been shown to be a function of the total equivalent concentration of hydroxyl radical generated, the concentration of DTT, and the presence of other competing substrates present in the irradiated volume, a method of normalizing the amount of exchange is desirable.

Figure 3:
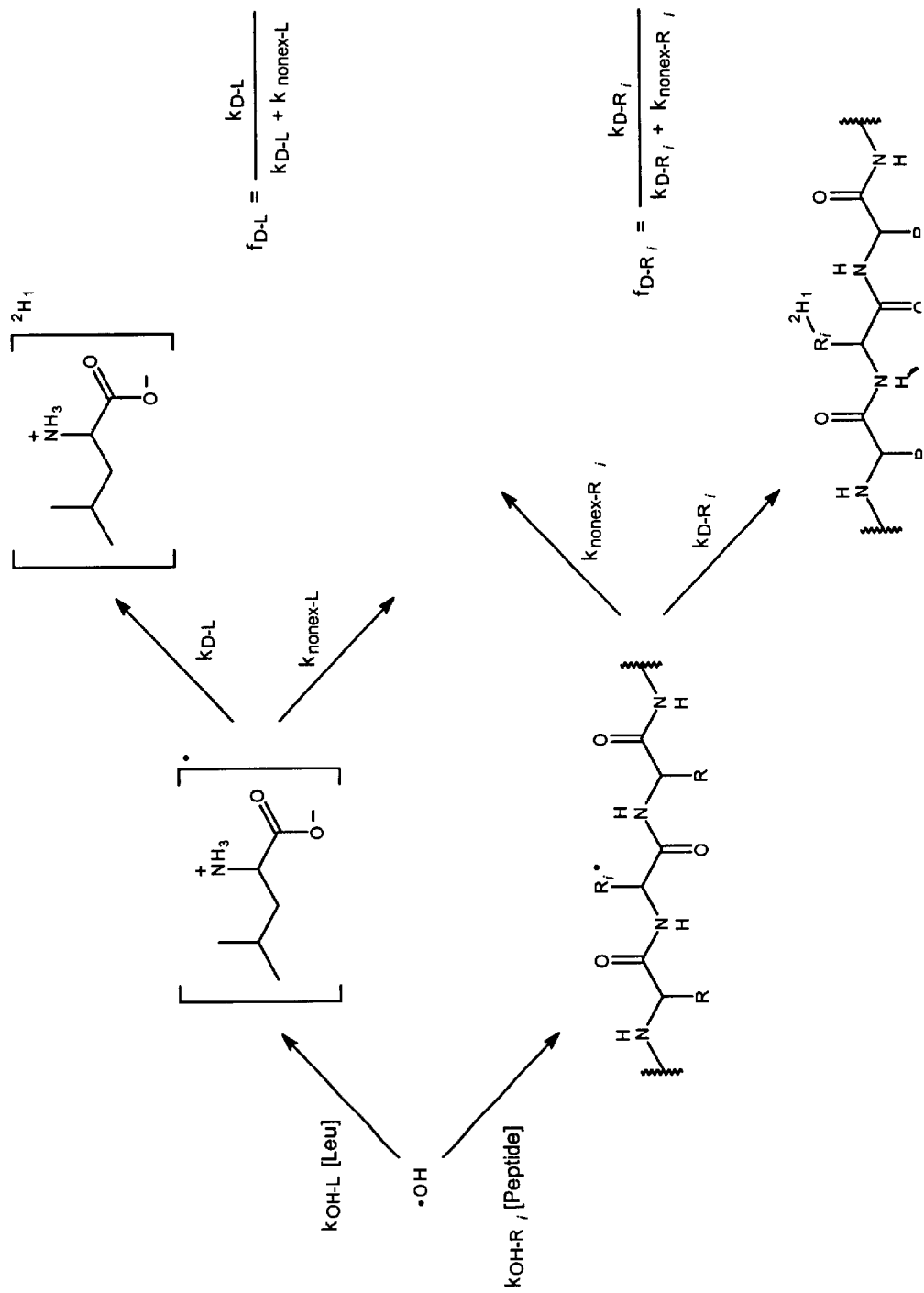
FIG. 3 is a schematic that outlines the usage of an internal reference.

Leucine or norleucine is a preferred internal reference for the exchange reaction. Our goal is to determine the rate constant for the reaction of hydroxyl radical with the peptide as an aggregate and with each individual residue within the peptide. As suggested by FIG. 3, the following equations describe the time course for the $^1$H/$^2$H exchange:

$$d[^2H]Leu/dt = k_{OH-L} \times [Leu] \times [.OH] \times f_{D-L} \qquad 5\text{-}1$$

$$d[^2H]R_i/dt = k_{OH-R^i} \times [R_i] \times [.OH] \times f_{D-R^i} \qquad 5\text{-}2$$

where $k_{OH-L}$ and $k_{OH-R^i}$ are the second order rate constants for the reaction of hydroxyl radical with the reference leucine and the $i_{th}$ residue of the peptide, respectively, and $f_{D-L}$ and $f_{D-R^i}$ are the fraction of the generated radicals that are quenched by $^2$H atom incorporation for the reference leucine and the $i_{th}$ residue, respectively. According to FIG. 3, this fraction is determined by the rate constant for $^2$H incorporation divided by the sum of the effective first order rate constants for all other decomposition processes. Hence, the fractions for the reference leucine and the $i_{th}$ residue would be given by:

$$f_{D-L} = k_{D-L}/(k_{D-L} + k_{nonex-L}) \qquad 5\text{-}3$$

$$f_{D-Ri} = k_{OH-R^i}/(k_{OH-R^i} + k_{nonex-R^i}) \qquad 5\text{-}4$$

Assuming that only the concentration of hydroxyl radical varies with time, integration of Equations 5-1 and 5-2 yield:

$$[^2H]Leu/Leu = k_{OH-L} \times f_{D-L} \int_0^t [OH] dt \qquad 5\text{-}5$$

$$[^2H]R_i/R_i = k_{OH-Ri} \times f_{D-Ri} \int_0^t [OH] dt \qquad 5\text{-}6$$

So, $$[^2H]R_i/R_i/[^2H]Leu/Leu = k_{OH-Ri} \times f_{D-Ri}/k_{OH-L} \times f_{D-L} \qquad 5\text{-}7$$

The virtue of the internal reference, as shown by Equation 5-7, is that the ratio of $^2$H incorporation into each residue to the incorporation into the reference eliminates the dependence on the variability of hydroxy radical with time. An additional virtue of using leucine as an internal reference is that previous results strongly suggest that $f_{D-L}$ is near unity so that $k_{OH-L} \times f_{D-L}$ can be closely approximated as the second order rate constant for the reaction of hydroxyl radical with the zwitterion of leucine determined by radiolysis studies of $1 \times 10^9$ M$^{-1}$s$^{-1}$. This permits the $^1$H/$^2$H exchange observed into a peptide of a given sequence to be predicted based on the known rate constants for hydroxyl radical reaction with given amino acids, assuming that $f_{D-AA}$ is unity for aliphatic amino acids except cysteine, where $f_{D-cys}$ is assumed to be 0 because the rate constant reflects abstraction of the solvent exchangeable S—H hydrogen.

This prediction is born out for CTP (SEQ ID NO: 2): the sum of the rate constants for the individual residues predicts that ther should be 3.1-fold greater $^1$H/$^2$H exchange into CTP (SEQ ID NO: 2) than for leucine which is in accordance with the obseved ratio of 2.7 (Table 5-5).

Example 6

$^1$H/$^2$H Exchange Into the C-Terminal Peptide-$G_{\alpha q}$ Protein (SEQ ID NO: 2) Complex Protein Purification and Preparation for $^1$H/$^2$H Exchange. The $G_{\alpha q}$ protein was expressed as the $G_{\alpha q}$-glutathione S-transferase fusion protein ($G_{\alpha q}$-GST). After purification the protein concentration was about two mg/ml in 50 mM Tris buffer, 10 mM EDTA, pH 8.0. Since the $^1$H/$^2$H exchange reaction buffer is 10 mM Na phosphate, pD 7.2 in D$_2$O, step dialysis was used. Step dialysis was chosen for three reasons. First, the protein sample contained a modest amount of glutathione that would scavenge hydroxyl radical and require removal prior to $^1$H/$^2$H exchange. Second, the difference in ionic strength and pD in the final buffer may cause the protein to precipitate if dialysis were performed in one step. Third, the dialysis tubing contains glycerol and other contaminants that would deleterious to $^1$H/$^2$H exchange and would be effectively removed using multiple dialysis steps. The dialysis consisted of three Na phosphate buffers at pH 6.8: (1) 100 mM Na phosphate 50 mM NaCl, 100 $\mu$M DTT, (2) 100 mM Na phosphate, 20 mM NaCl, 100 $\mu$M DTT, and (3) 100 mM Na phosphate, 50 $\mu$M DTT. The protein (sample volume of 12.5 ml) was then dialyzed against two D$_2$O buffers each containing 100 mM Na phosphate and 50 $\mu$M DTT (each at a volume of 12.5 ml). Before the $^1$H/$^2$H exchange studies the protein was step dialyzed against several buffers resulting in a concentration of 50 $\mu$M $G_{\alpha q}$-GST in 100 mM sodium phosphate pD 7.2 with 50 $\mu$M DTT.

$^1$H/$^2$H Exchange of Free and Bound Peptide. The 1H/$^2$H exchange reaction was performed in a manner as previously described. The reaction conditions consisted of (1) 25 mM peptide, 50 mM $G_{\alpha q}$GST, 20 mM 2,4-dinitrophenyl-leucine (2,4-DNP-Leu) in the presence of 50 mM DTT in 100 mM Na phosphate, pD 7.2 (pD=pH meter reading in D$_2$O+0.4; or (2) 30 mM peptide, 15.6 mM $G_{\alpha q}$-GST, 12.5 mM 2,4-dinitrophenyl-leucine (2,4-DNP-Leu) in the presence of 35 mM DTT in 70 mM Na phosphate, pD 7.2. The sample was irradiated such that a total equivalent concentration of hydroxyl radical produced was 50 mM. This was accomplished by exposing the sample to the $^{137}$Cs source for a specified period of time as determined using a dose rate of 0.52 Gy s$^{-1}$ and the G(OH radical) value of 5.6×10$^{-7}$ mol J$^{-1}$ for N$_2$O saturated solutions (22 mM). After radiolytic exposure, an additional 20 mM of reduced DTT was added by transferring an aliquot 4 ml from a 2.5 mM DTT solution previously gassed with N$_2$O, and then the sample was exposed to another equivalent dose. Exposure to O$_2$ during the transfer was minimized by providing a positive pressure of N$_2$O over the sample using a needle attached to a balloon filled with N$_2$O. The process was repeated a total of eight times for a cumulative total equivalent concentration of hydroxyl radical of 400 mM. The concentrations of CTP (SEQ ID NO: 2) and DTT were determined by quantization of the sulfhydryl groups using a DTNB assay described herein. The concentration of $G_{\alpha q}$-GST was determined using the Bradford assay.

Example 7

$^1$H/$^2$H Exchange Into Leucine Using Peroxynitrous Acid Decomposition

ONOOLi Synthesis. Because the amino acid desalting method utilized the precipitation of Li phosphate, the synthesis of ONOO⁻ was a slightly modified version of King (King, Peter A. Ph.D. Thesis, Brown University Chemistry Department 1993) where 1.0 M LiOH replaced 1.0 M KOH. A volume of 20 ml of 0.6 M $NaNO_2$ was rapidly added to a stirring solution of 20 ml of 0.9 M $H_2O_2$ in 0.6 M HCl on ice (1±1° C.) and quenched three to five seconds later by the addition of 20 ml of 1.0 M LiOH. The pH of the solution was usually between 12.3–12.6. If the pH was lower, it was raised by adding 1.0 M LiOH. This synthesis was repeated two more times, and the solution producing the highest concentration of ONOO⁻ ($\epsilon$=1670 $M^{-1}cm^{-1}$ at 302 nm) was retained. The excess $H_2O_2$ was removed from the ONOOLi solution by adding 500 mg $MnO_2$ 50 weight % on activated carbon. The solution was filtered using a 3 ml syringe and a 0.45 $\mu$m filter (Millipore). Aliquots of 1 ml were placed in 1.5 ml Eppendorf tubes and stored at −80° C. Typically, the concentration of ONOO⁻ was around 150 mM.

$^1H/^2H$ Exchange in the Presence of DTT. A reaction volume of 2.0 ml contained 100 $\mu$M L-leucine and 50 $\mu$M DTT in 220 mM Li phosphate pD 6.7 at 4° C. The solution was placed on ice and gassed with Ar for thirty minutes to achieve anaerobic conditions. The ONOOLi solution was stored at −80° C. and was thawed immediately before use. The solution was placed on ice and the concentration of the ONOO⁻ ion was determined spectrophotometrically ($\epsilon_{302\ nm}$=1670 $M^{-1}cm^{-1}$). The $^1H/^2H$ exchange reaction was performed by adding 2 $\mu$l of 114 mM ONOOLi to the reaction vessel, measuring the concentration of reduced DTT that remained using a DTNB assay, followed by the addition of 2 $\mu$l of 50 mM DTT. After five additions of ONOOLi, an aliquot of 450 $\mu$l (called an "addition point") was removed from the reaction vessel. This procedure was repeated until a total of four addition points had been taken.

L-Ascorbic Acid as the Deuterium Atom Donor. The $^1H/^2H$ exchange reaction was also performed with 25 or 50 $\mu$M L-ascorbic acid. The amount of L-ascorbic acid remaining after ONOOLi addition was quantified using a ferriphenanthroline (FPA) assay.

Example 8

Preparation of Samples for Isotope Ratio Measurements

Desalting Amino Acids and Peptides for ESI-MS Analysis. An AG 50W-X8 (Bio-Rad) column was made by suspending 50 mg of the H⁺-form in 1 ml of 1.0 M $NH_4OH$ (freshly prepared) and filtering the suspension through a glass wool plug in a Pasteur pipette. The resin was washed with 1.0 ml of 1.0 M HCl and three times with 1.0 ml of 0.010 M HCl. After Li phosphate removal by ethanol precipitation, the amino acid or peptide sample (pH 1.3 by addition of HCl after ethanol evaporation) was loaded, washed three times with 1.0 ml of 0.010 M HCl, and subsequently eluted with 0.10 M $NH_4OH$. The second through sixth 1.0 ml fractions were pooled and the solvent removed by vacuum centrifugation. The residue was dissolved in ethanol and dried by vacuum centrifugation to remove any residual $NH_3$. This residue was dissolved in 1:1 methanol:2% acetic acid (v/v) for ESI-MS analysis.

Reversed-Phase HPLC Purification of Peptides. All peptides were purified by reversed-phase HPLC using a Macrosphere $C_{18}$ column (4.6 mM×250 mM) (Alltech) and a Perkin-Elmer Series 400 liquid chromatograph. The peptides were monitored by measuring the absorbance between 220 and 340 nM using a Hewlett Packard 8452A diode array spectrophotometer. The solvents used were 0.1% TFA (solvent A) and acetonitrile containing 0.1% TFA (solvent B) at a flow rate of 1 ml/min. The column was equilibrated for ten minutes with 100% of solvent A. After loading the sample, the column was washed for ten minutes with 100% of solvent A, followed by a sixty minute linear gradient from 0 to 100% of solvent B. The column was washed for ten minutes with 100% of solvent B, and then a five minute step gradient, followed by a ten minute wash with 100% of solvent A, was used to equilibrate the column for the next injection. The appropriate one mL fractions were pooled and the solvent removed via vacuum centrifugation. Several one mL additions of water were added, then removed, prior to storing the samples at −20° C. until needed.

Peptide Hydrolysis. Peptides were hydrolyzed into their constitutive amino acids by acid hydrolysis. The reversed-phase HPLC purified peptide was dissolved in 0.5 ml of distilled-deionized $H_2O$, and then 0.5 ml of concentrated HCl was added. The sample was placed into a 1 ml glass ampule and gassed with $N_2$ for 30 minutes, and then immediately flame sealed. The sealed ampule was placed into a heating block at 110° C. for twelve hours. Acid catalyzed proton exchange does not occur with side chain C—H bonds and only to a limited extent at the $C_\alpha$ position.

Extraction of DNS-Amino Acids. The amino acids subjected to $^1H/^2H$ exchange were derivatized with DNS-Cl as described herein. Since DTT was also present in the reaction, the DNS-DTT and diDNS-DTT derivatives were extracted prior to the DNS-amino acid derivatives. After the DNS-Cl derivatization reaction was complete, the volume of the solution was increased to 0.4 ml by the addition of $H_2O$. Then, three equal volumes of water saturated ethyl acetate were used to extract the DTT adducts. The aqueous layer was acidified using 800 $\mu$L of 10% (v/v) formic acid. The DNS-amino acid derivatives were extracted using three equal volumes of water saturated ethyl acetate. The extracts were pooled and the ethyl acetate removed under a stream of dry $N_2$. The remaining residue was stored at −20° C. until ESI-MS analysis.

Reversed-Phase HPLC Purification of DNS-Amino Acids. The purification of DNS-amino acid derivatives was performed using reversed-phase HPLC using a Macrosphere $C_{18}$ column (4.6 mm×250 mm) (Alltech) and a Perkin-Elmer Series 400 liquid chromatograph. The DNS-amino acids were monitored by measuring the absorbance between 220 and 340 nm using a Hewlett Packard 8452A diode array spectrophotometer. Solvent A contained 0.2 M $NH_4HCO_3$ in acetonitrile:$H_2O$ (10:90, v:v), and solvent B contained 0.2 M $NH_4HCO_3$ in acetonitrile:$H_2O$ (45:55, v:v). The column was equilibrated for ten minutes with 100% of solvent A. After loading the sample, the column was washed for ten minutes with 100% solvent A, followed by a series of linear gradients: 25 minute linear gradient from 0 to 30% of solvent B; 20 minute linear gradient from 30 to 45% of solvent B; and 15 minute linear gradient from 45 to 100% of solvent B. The column was washed for 15 minutes with 100% of solvent B, and then a 5 minute step gradient, followed by a 10 minute wash with 100% of solvent A, was used to equilibrate the column for the next injection. The appropriate 1 ml fractions were pooled and the solvent removed via vacuum centrifugation. Then, 0.5 ml of 10% (v/v) formic acid was added to each residue and the solvent removed via vacuum centrifugation. The samples were stored in the dark at −20° C. until ESI-MS analysis.

HPLC Purification of CTP (SEQ ID NO: 2) and 2,4-DNP-Leu. After $^1H/^2H$ exchange reactions, the free and bound $^1H/^2H$ exchange samples may be treated similarly. Initially, the peptide-protein interaction is disrupted by lowering the sample pH to 4 by acetic acid addition. The protein is subsequently removed by filtering the sample through a Centricon 10 concentrator (Amicon, Inc.). The filtrate is collected and the pH titrated to 6.8 by NaOH addition. To prevent peptide dimerization via disulfide formation, the cysteine sulfhydryls are carboxymethylated using iodoacetate. The carboxymethylated CTP (SEQ ID NO: 2) (cm-CTP) and 2,4-DNP-Leu are stored at 4° C. until purification using reversed-phase HPLC. cm-CTP and 2,4-DNP-Leu are purified by using a Vydac $C_{18}$ column (2.1×150 mm, 5 m) and a Perkin-Elmer Series 400 liquid chromatograph. The peptides (including the 2,4-DNP-Leu) were monitored between 200 and 400 nM by photodiode array (PDA) detection using a Hewlett Packard 8452A diode array spectrophotometer. The solvents used were 0.1% TFA (solvent A) and acetonitrile containing 0.1% TFA (solvent B). The column was equilibrated with 100% of solvent A for 20 minutes at a flow rate of 0.25 m/min. After loading the sample, the column was washed for 10 minutes with 100% of solvent A, followed by a 60 minute linear gradient from 0 to 100% of solvent B. The column was washed for 10 minutes with 100% of solvent B, then a 5 minute step gradient followed by a 20 minute wash with 100% of solvent A were used to equilibrate the column for the next injection. Chromatographs generated using 220 nm were used to identify peptide peaks and those generated using 350 nm were used to identify 2,4-DNP-Leu. The appropriate 0.25 ml fractions were pooled and the solvent removed via vacuum centrifugation. The samples were stored at −20° C. until needed.

Example 9

Quantitative Assays 5,5'-Dithiobis(2-nitrobenzoic Acid) (DTNB) Assay. The quantification of the sulfhydryl groups of DTT and CTP (SEQ ID NO: 2) was performed using the DTNB assay. The solutions used were (1) the assay buffer consisting of 0.12 M K phosphate containing 1 mM EDTA, pH 7.2 and (2) the DTNB solution containing 10 mM DTNB in 50 mM $K_2HPO_4$. For each determination mL of the DTNB solution were added to 460 mL of the assay buffer in a cuvette. The reaction was initiated by the addition of 10 mL of sample and was allowed to continue for 5 minutes at room temperature (20–25° C.). The concentration of thiols was determined by measuring the absorbance of 2-nitro-5-thiobenzoate (NTB) at 412 nm ($e_{412\ nm}$=13,600 $M^{-1}cm^{-1}$).

Ferriphenanthroline (FPA) Assay. A stock solution of 1.8 mM FPA (256 mg o-phenanthroline (1,10-phenanthroline) and 87 mg $FeNH_4(SO_4)_2.12H_2O$ in 100 of $H_2O$ that was adjusted to pH 5 by HCl addition) was diluted 1:10 in 0.1 M imidazole buffer, pH 8.0, to generate the FPA assay solution. After the addition of 10 μL of sample to 490 μL of FPA assay solution, the absorbance of the o-ferrophenanthroline complex at 515 nM was immediately recorded, using L-ascorbic acid (0 to 100 μM) to generate a standard curve.

2,4, 6-Trinitrobenzenesulfonic Acid (TNBSC) Assay. A borate assay buffer was made by adding 25 mL of 0.1 M $Na_2B_4O_7$ in 0.1 M NaOH to 24 mL of $H_2O$. The sulfite solution (made fresh daily) contained 0.15 mL of 0.4 M $Na_2SO_3$ (made fresh weekly) and 9.85 mL of 0.4 M $NaH_2PO_4$. A solution of 1.1 M TNBS (100 mg in 200 μL $H_2O$) was made fresh weekly and stored at −20° C. To perform the assay, 10 μL of sample were added to 490 μt of the borate assay buffer in a cuvette. A blank was measured simultaneously using 10 μL of $H_2O$. To initiate the reaction 10 μL of 1.1 M TNBS were added. After five minutes the reaction was quenched by the addition of 250 μL of the sulfite solution. The concentration of the TNP-amino acid-sulfite complex was determined by measuring the absorbance at 420 nM. A standard curve for L-leucine reaction concentrations between 0 and 500 μM was generated.

2-Nitro-5-thiosulfobenzoate (NTSB) Assay. A stock solution consisting of 50 mM glycine, 100 mM $Na_2SO_3$, and 3 mM EDTA, pH 9.5 was prepared, and 2-nitro-5-thiosulfobenzoate (NTSB) was prepared. The NTSB assay solution was made by 1:100 dilution of NTSB with the assay buffer with the pH adjusted to 9.5 by NaOH addition. For each determination 10 μL of the sample were added to 490 μL of the NTSB assay solution in a cuvette. The reaction was allowed to continue for 5 minutes at room temperature (20–35 25° C.). The concentration of disulfides was determined by measuring the absorbance of 2-nitro-5-thiobenzoate (NTB) at 412 nm ($e_{412\ nm}$=13,600 $M^{-1}s^{-1}$). Because the disulfide bond concentrations are determined by sulfitolysis followed by the free thiols reacting with NTSB, the free thiol concentration needed to be measured using the DTNB assay in order to determine the disulfide bond concentration.

Example 10

Derivatization

Amino Acid Derivatization Using DNS-Cl. The hydrolyzed amino acids in 6 N HCl were dried down via vacuum centrifugation. The resulting residue was dissolved in 200 μL of 0.5 M $NaHCO_3$, then 100 μL of a dansyl chloride (DNS-Cl) solution containing a 10-fold excess over the total of all reactive groups was added. A solution containing the appropriate amount of DNS-Cl in acetone was made. Material not dissolving in the acetone was removed by centrifugation at 15000×g for 1 minute; the supernatant was removed and used for the derivatization reaction. The reaction was incubated for 1 hour at 37° C., followed by the addition of 800 μL of 10% (v/v) formic acid. The DNS-amino acids were stored at 4° C. and did not decompose under these conditions.

Leucine Derivatization Using 2,4-Dinitrofluorobenezene. Leucine (13 mg) was dissolved in 400 μL of 6 M Guanidine HCl in 0.1 M Na phosphate pH 8, followed by the addition of 100 μL of 2,4-DNFB in DMF (1:100 2,4-DNFB:DMF). The reaction was incubated at 60° C. for 30 minutes. Purification 2,4-DNP-Leu was accomplished using reversed-phase HPLC described for cm-CTP purification. Each fraction containing 2,4-DNP-Leu was stored in the dark at −20° C. until needed. For the exchange reactions, a fraction was selected and $D_2O$ (100 μL) was added to produce a 2,4-DNP-Leu stock solution which was quantified using $e_{369\ nm}$=16,000 $M^{-1}cm^{-1}$.

Carboxymethylation of CTP (SEQ ID NO: 2). After the $^1H/^2H$ exchange reaction, approximately five mg of iodoacetate (sodium salt) was added to the sample containing CTP (SEQ ID NO: 2). Since the solution was at neutral pH, only the sulfhydryl groups were carboxymethylated. Within five minutes of iodoacetate addition, the extent of sulfhydryl carboxymethylation was monitored by using the DTNB assay. An additional aliquot of iodoacetate was added if required to complete the carboxymethylation.

Example 11

Calculating the Extent of $^1H/^2H$ Exchange

The extent of $^1H/^2H$ exchange ($\Delta\%\ ^2H$) at low levels of exchange was calculated using the equation:

Δ% $^2H$=(Mean Isotope Ratio of the $^1H/^2H$ Exchange Sample−Mean Isotope Ratio of the Standard)×100

The concentration of deuterated amino acid or peptide resulting from $^1$H/$^2$H exchange was determined using the equation:

$$[[^2H]Product] = \Delta\% \, ^2H \times [Reactant]$$

Efficiency, as used herein, is defined as:

$$Efficiency(\%) = \frac{[[^2H]Product]}{[Total\ OH\ Radical\ Produced]} \times 100$$

For the ESI-MS analysis of cm-CTP and the internal reference leucine (analyzed as DNS-Leu), the relative intensity (%) of each ion is determined using the equation:

$$[M+H+i]^+_{RelativeIntensity} = \frac{[M+H+i]^+_{Intensity}}{\sum_{i=0}^{3} [M+H+i]^+_{Intensity}} \times 100$$

The resulting values for the relative intensities were used to calculate the percentage of $^2$H exchange (% $^2$H)

$$\% \, ^2H = ([M+H+1]^+_{1H/2H} - [M+H+1]^+_{std}) + 2([M+H+2]^+_{1H/2H} - [M+H+2]^+_{std}) + 3([M+H+3]^+_{1H/2H} - [M+H+3]^+_{std})$$

where $^1$H/$^2$H and STD denote the relative intensity of the $^1$H/$^2$H exchange sample and standard, respectively.

Example 12

Examining Alkyl $^1$H/$^2$H Exchange Using NMR Spectroscopy

Radiolysis. $^1$H/$^2$H exchange reactions were performed in D$_2$O and contained 10 mM NaPi, pD 7.2, 100 μM amino acid, 25 μM DTT, and 50 μM OH radical in a volume of 5.0 ml at room temperature (20–25° C.). The $^2$H/$^1$H exchange reaction for the d$_8$-DL-valine experiment was performed in H$_2$O at a pH of 6.8. The samples were degassed for two hours with N$_2$O. The samples were irradiated using a $^{137}$Cs source within 30 minutes after the N$_2$O treatment.

Derivatization of Amino Acids Using 2,4,6-Trinitrobenzenesulfonic Acid. After alkyl $^1$H/$^2$H exchange of the sample, the solvent was removed via vacuum centrifugation and was derivatized using TNBS. A solution of 1 mg/ml TNBS-borate solution was made by dissolving solid TNBS in 4% (w/v) Na$_2$B$_4$O$_7$.10H$_2$O (pH~9.2). To a 100 μl solution containing 1 μmol of amino acid, a volume of 1.0 ml of 1 mg/ml TNBS-borate solution was added. The reaction was incubated at 37° C. for 15 minutes, then allowed to cool to room temperature (20–25° C.). Because the irradiated sample also contained DTT, TNP-DTT and diTNP-DTT derivatives are also present, an extraction procedure was developed to remove these DTT adducts prior to extracting TNP-amino acid. After the reaction solution cools to room temperature, three volumes of 40 percent ethyl acetate:60 percent cyclohexane (v/v) were used to extract the DTT adducts. The solution was acidified by the addition of 0.5 ml of 6 N HCl:5 M NaCl (1:1 v/v). The TNP-amino acid was then extracted with three equal volumes of chloroform. The chloroform extractions were pooled and the solvent was evaporated via vacuum centrifugation. NMR analysis with test compounds indicated that the amino acid derivatization and TNP-amino acid extraction were complete. The TNP-amino acid was stored at −20° C. until a day before the $^1$H-NMR analysis. At this time 200 μl of D$_2$O was added to the sample and the solvent was removed via vacuum centrifugation. This D$_2$O washing was repeated two more times, then 500 μl of D$_2$O was added to the residue and the solution was transferred into an NMR tube.

NMR Conditions. The $^1$H-NMR spectra were collected on a Varian Inova 600 MHz NMR operating at 599.908 MHz. The sweep widths for $^1$H and $^2$H were 6.6 and 1.5 kHz, respectively. The $^1$H data were acquired in D$_2$O at 25° C. with a solvent (H$_2$O) presaturation pulse 1.5 s in duration. A pulse width of 7.9 μs followed by a two second acquisition time was used. The $^2$H spectra were collected on the same instrument operating at 92.090 MHz. The $^2$H data were acquired in $^2$H-depleted H$_2$O at 25° C., and the spectrometer's electronics were optimized for the $^2$H signal. A pulse width of 32 μs followed by a 1.5 second acquisition time was used. Proton decoupling was not used in these acquisitions.

Discussion. Determination of the site(s) of $^1$H/$^2$H exchange of amino acids were initially attempted with $^1$H-NMR using two approaches. The first involved $^2$H/$^1$H exchange with a perdeutero amino acid, d$_8$-DL-valine, with $^1$H-NMR analysis performed before and after radiolysis. It was anticipated that the peaks corresponding to the α, β, and γ hydrogens in the standard could be integrated and compared to the values obtained for the irradiated sample. If deuterium-hydrogen exchange were to occur, the area of the peak corresponding to the site of hydrogen atom donation would increase, allowing the unequivocal assignment of the carbon-centered radical that was quenched by DTT. However, the interpretation of the data was complicated by (1) DTT or some contaminant present in the irradiated sample and not the standard and (2) a lack of a standard peak containing a known number of hydrogens. To facilitate the quantification of hydrogen incorporation, the amino acid required derivatization prior to $^1$H-NMR analysis. This second approach involved derivatizing the amino acid with the amino acid with prior to $^1$H-NMR analysis.

The amino acid was derivatized using 2,4,6-trinitrobenzenesulfonic acid to produce the 2,4,6-trinitrophenyl-amino acid, thus allowing for (1) extraction of the 2,4,6-trinitrophenyl-amino acid from the reaction mixture and (2) providing two aromatic hydrogens that are downfield to the side chain hydrogens and can serve as an internal standard. The peaks corresponding to the side chain hydrogens in the standard were compared to the peaks obtained for the irradiated sample. The differences in the splitting pattern due to deuterium incorporation allowed the assignment of the carbon-centered radicals that were quenched by DTT. The results for leucine demonstrated that the sites of deuterium atom donation were at the methylene and methine carbons of leucine. Because of the overlap between the methylene and methine protons of the TNP-Leu, quantifying the extent of $^1$H/$^2$H exchange and assigning it to either the methylene or the methine positions is not possible. In addition the analysis of TNP-d$_8$-dl-valine provided (1) no detectable difference in the splitting pattern of the α, β, and γ hydrogens peaks and (2) integration of these peaks normalized to the aromatic hydrogens of TNP moiety at approximately 9.0 ppm would not allow for the unequivocal assignment of the sites of exchange due to the low extent of the exchange relative to peak integration error. These data made it clear that $^1$H-NMR spectroscopy was not effective in identifying sites of $^1$H/$^2$H exchange, thus the use $^2$H-NMR spectroscopy was pursued.

There two advantages to using $^2$H-NMR to examine alkyl $^1$H/$^2$H exchange into amino acids. The main advantage is that presence of $^2$H is being monitored and not the changes in $^1$H signal induced by $^2$H incorporation. An additional feature is that no derivatization is required. The ability to generate $^1$H and $^2$H-NMR spectra from the same ample by changing solvent from D$_2$O to H$_2$O enables the identification of oxidized products and sites of $^1$H$^2$H exchange.

mined by infusion using ESI-MS and appear in Table 13-1. The ratio of the differences between the isotope ratios of the free and bound peptide residues are presented in Table 13-1. Using the data in Table 13-1, the protection factors were calculated and are listed in Table 13-3.

TABLE 13-1

Isotope Ratios of the Residues for the C-Terminal Peptide (SEQ ID NO: 2) and the Internal Reference 2,4-Dinitrophenyl Leucine.

| | Compound | | | Isotope Ratio | | | | |
|---|---|---|---|---|---|---|---|---|
| | 50 µM GST-G$_{aq}$/100 µM CTP (SEQ ID NO: 2) | | | 30 µM GST-G$_{aq}$/15.6 µM CTP (SEQ ID NO: 2) | | | | |
| | 200 µM OH Radical | | | 400 µM OH Radical | | 400 mM OH Radical | | |
| | Standard | Free | Bound | Free | Bound | Standard | Free | Bound |
| Residue[a] | | | | | | | | |
| Ser | 0.182 | 0.182 | 0.181 | 0.182 | 0.181 | 0.179 | 0.175 | 0.183 |
| Asp | 0.189 | 0.183 | 0.192 | 0.194 | 0.187 | 0.190 | 0.206 | 0.219 |
| Glu | 0.200 | 0.214 | 0.208 | 0.226 | 0.204 | 0.203 | 0.299 | 0.282 |
| Lys[b] | 0.361 | 0.385 | 0.371 | 0.414 | 0.378 | 0.377 | 0.472 | 0.450 |
| Ala | 0.181 | 0.190 | 0.183 | 0.200 | 0.184 | 0.180 | 0.198 | 0.202 |
| Cys[c] | 0.212 | | | | | | | |
| Val | 0.204 | 0.235 | 0.217 | 0.260 | 0.225 | 0.204 | 0.308 | 0.286 |
| Leu | 0.213 | 0.294 | 0.248 | 0.366 | 0.263 | 0.212 | 0.509 | 0.442 |
| Gly | 0.169 | 0.174 | 0.173 | 0.170 | 0.171 | 0.170 | 0.182 | 0.183 |
| Ile | 0.214 | 0.300 | 0.249 | 0.374 | 0.270 | 0.211 | 0.564 | 0.470 |
| Internal Reference | | | | | | | | |
| 2,4-DNP-Leu | 0.145 | 0.164 | 0.150 | 0.170 | 0.164 | 0.159 | 0.173 | 0.163 |

[a]The isotope ratios listed are those of the corresponding dansyl derivative analyzed by LC-MS.
[b]The value for the Lys residue corresponds to the diDNS-Lys derivative.
[c]The value for the Cys residue corresponds to the carboxymethylated form of DNS-Cys. This residue is destroyed during peptide hydrolysis and is not present in most samples.

Example 13

Measurement of Hydroxyl Radical Promoted Alkyl Hydrogen/Deuterium Protection Factors in Peptide-protein Interactions In this example the interaction between the C-terminal peptide (SNEQKACKVLGI (SEQ ID NO: 2), abbreviated as CTP) of i3 of the 5-HT$_{2A}$ receptor and G$_{aq}$ is examined using a method of alkyl $^1$H/$^2$H exchange. In this study of the CTP-G$_{aq}$ interaction, the extent of $^1$H/$^2$H exchange into the residues of the CTP (SEQ ID NO: 2) is examined in the presence and absence of G$_{aq}$ to determine a protection factor for each residue of the peptide. A large protection factor should be produced if the interaction of the CTP (SEQ ID NO: 2) with G$_{aq}$ results in the reduction of solvent-accessible surface area of the residue.

Figure 4:
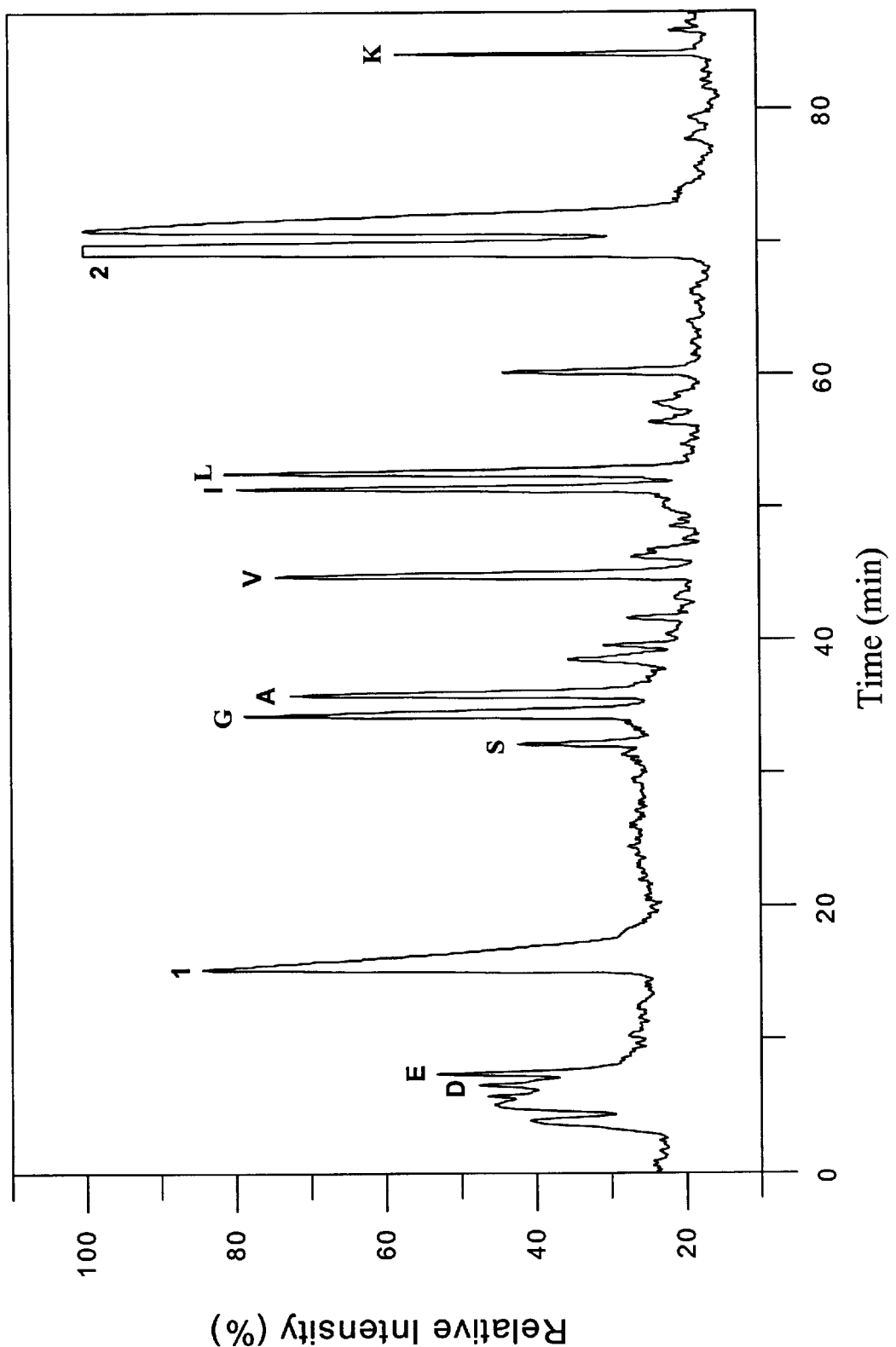
FIG. 4 is a total ion chromatograph of DNS-Amino Acids derived from the C-Terminal Peptide (SEQ ID NO: 2) subjected to $^1H/^2H$ Exchange in the presence of an internal reference. The assignment of each DNS-amino acid was determined by the m/z value of the [M+H]$^+$ ion. Peak 1 is dansyl sulfonic acid (252 m/z) and Peak 2 is the dansyl sulfonic amide (251 m/z).
Figure 5:
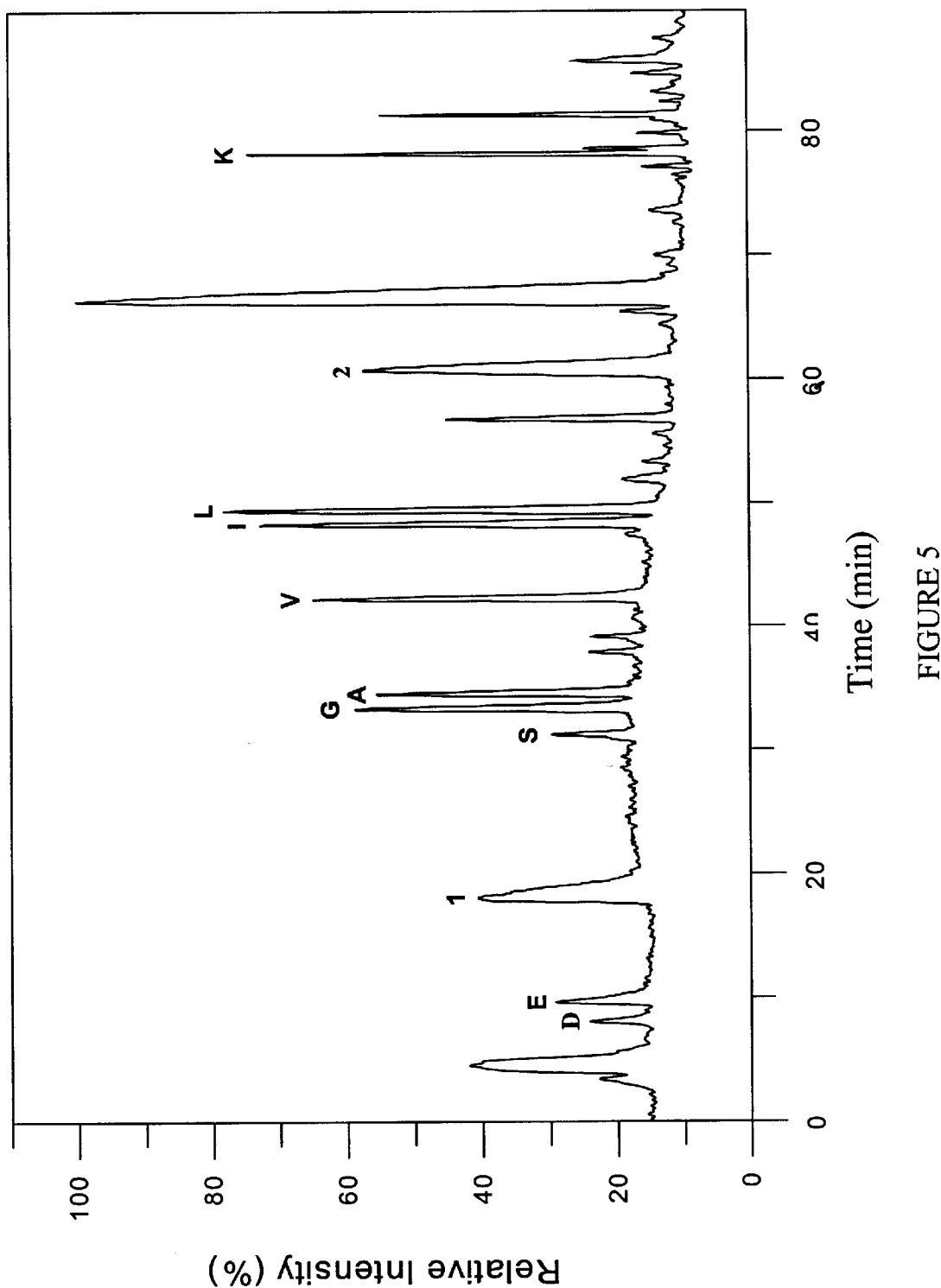
FIG. 5 is a total ion chromatograph of DNS-Amino Acids derived from the C-Terminal Peptide (SEQ ID NO: 2) Subjected to $^1H/^2H$ exchange in the Presence $G_{aq}$ and the Internal Reference. The assignment of each DNS-amino acid was determined by the m/z value of the [M+H]+ ion. Peak 1 is dansyl sulfonic acid (252 m/z) and Peak 2 is the dansyl sulfonic amide (251 m/z).
Figure 6:
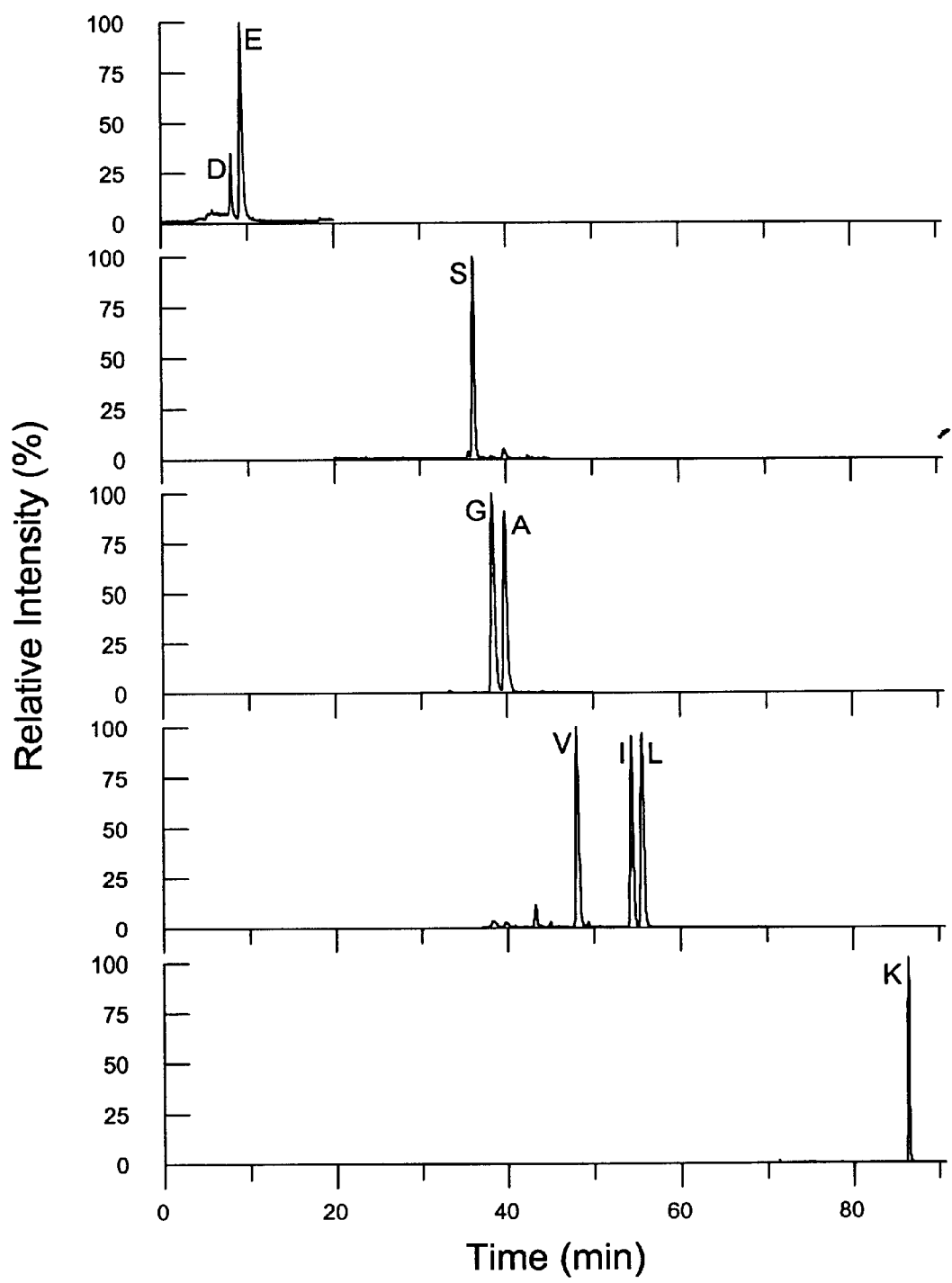
FIG. 6 is selected ion chromatographs of DNS-Amino Acids as described in Example 13. For isotope ratio measurements, each peak corresponding to the [M+H]+ ion was integrated with the appropriate background subtracted. The isotope ratio was determined by taking the ratio of the [M+H+1]+/[M+H]+ integrated areas.
Figure 7:
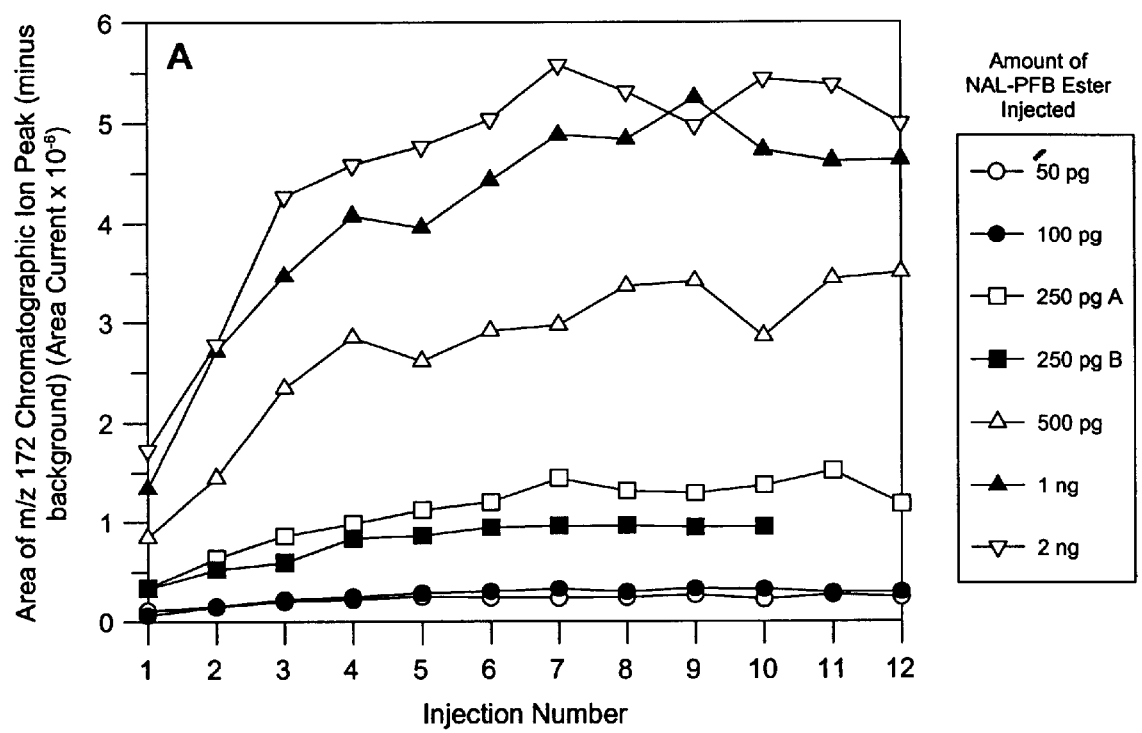
FIG. 7 depicts GC-MS ion peak area dependence based on the injection number. The area of each gas chromatographic peak corresponding to the 172 m/z ion current was integrated and plotted as a function of the injection number.
Figure 8:
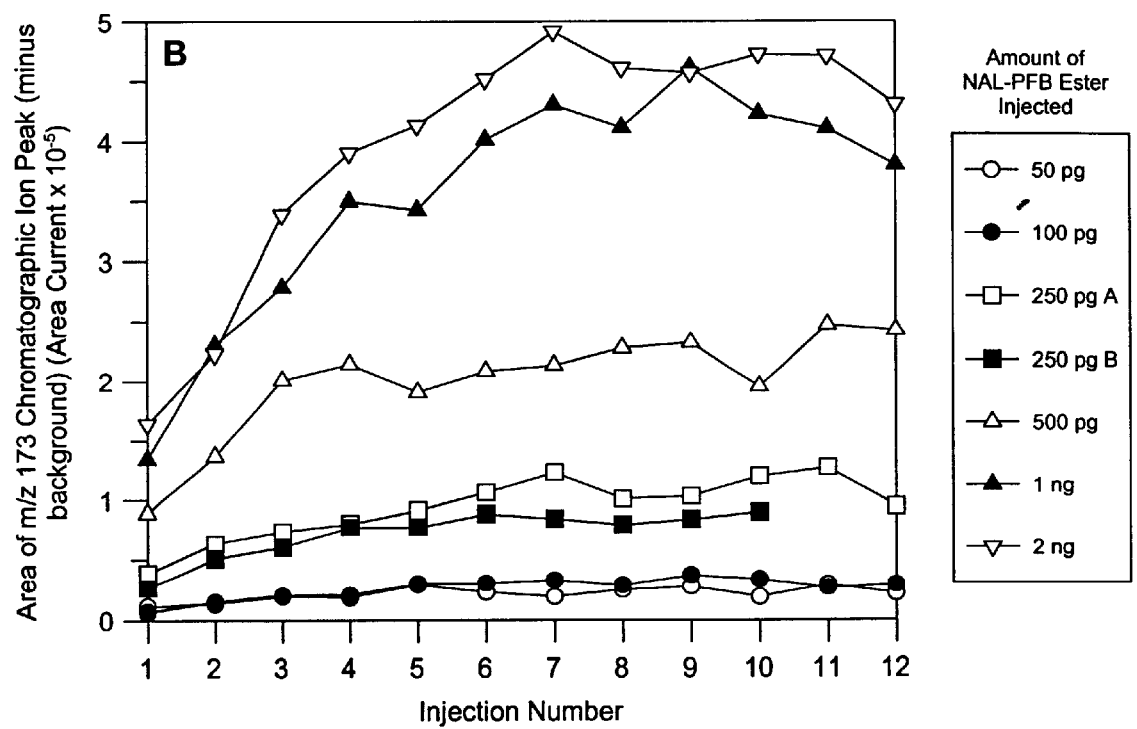
FIG. 8 depicts GC-MS ion peak area dependence based on the injection number. The area of each gas chromatographic peak corresponding to the 173 m/z ion current was integrated and plotted as a function of the injection number.

$^1$H/$^2$H Exchange of Free and Bound Peptide. The $^1$H/$^2$H exchange reaction was performed for the CTP (SEQ ID NO: 2) in the presence and absence of the protein GST-G$_{aq}$. The isotope ratios for each DNS-amino acid produced by the free and bound peptide was determined by LC-MS and appear in Table 13-1. The total ion current (TIC) chromatographs of DNS-amino acids produced by CTP (SEQ ID NO: 2) subjected to $^1$H/$^2$H exchange in the absence and presence of the protein GST-G$_{aq}$ appear in FIGS. 4 and 5, respectively. Selected ion chromatographs generated by a typical SIM acquisition for each DNS-amino acid produced by CTP (SEQ ID NO: 2) hydrolysis is shown in FIG. 6. The isotope ratios of the internal reference 2,4-DNP-Leu were deter-

TABLE 13-2

Comparison of Isotope Ratios for the Residues of C-Terminal Peptide (SEQ ID NO: 2) Subjected to $^1$H/$^2$H Exchange in the Absence or Presence of G$_{aq}$. Δ Isotope Ratio$_{free}$/Δ Isotope Ratio$_{bound}$[a]

| | 50 µM GST-G$_{aq}$/100 µM CTP (SEQ ID NO: 2) | | 30 µM GST-G$_{aq}$/15.6 µM CTP (SEQ ID NO: 2) |
|---|---|---|---|
| Residue | 200 µM OH Radical | 400 µM OH Radical | 400 µM OH Radical |
| Ser | 0 | 0 | −1.2 |
| Asp | −2.0 | −2.5 | 0.53 |
| Glu | 1.8 | 6.5 | 1.2 |
| Lys[b] | 2.4 | 3.1 | 1.3 |
| Ala | 4.5 | 6.3 | 0.80 |
| Val | 2.4 | 2.7 | 1.3 |
| Leu | 2.3 | 3.1 | 1.3 |
| Gly | 1.2 | 0.50 | 0.99 |
| Ile | 2.5 | 2.9 | 1.4 |

[a]Δ Isotope Ratio = Isotope Ratio$_{1H/2H}$-Isotope Ratio$_{standard}$
[b]The value for the Lys residue corresponds to the diDNS-Lys derivative.

TABLE 13-3

The Protection Factors for the Residues of the C-Terminal Peptide (SEQ ID NO: 2). Protection Factor

| Residue | 50 µM GST-G$_{aq}$/100 µM CTP (SEQ ID NO: 2) | | 30 µM GST-G$_{aq}$/15.6 µM CTP (SEQ ID NO: 2) |
|---|---|---|---|
| | 200 µM OH Radical | 400 µM OH Radical | 400 µM OH Radical |
| Ser | 0 | 0 | −0.35 |
| Asp | −0.77 | −1.5 | 0.16 |
| Glu | 0.51 | 6.3 | 0.37 |
| Lys | 0.58 | 2.3 | 0.39 |
| Ala | 2.0 | 7.2 | 0.24 |
| Val | 0.61 | 2.0 | 0.38 |
| Leu | 0.59 | 2.4 | 0.39 |
| Gly | 0.32 | 0 | 0.30 |
| Ile | 0.62 | 2.2 | 0.41 |

The Protection Factor. The isotope ratios of the residues of CTP (SEQ ID NO: 2) subjected to hydroxyl radical promoted $^1$H/$^2$H exchange in the free and bound forms can be corrected for the $^1$H/$^2$H natural isotope abundance by subtracting the isotope ratios for the standards (Δisotope ratio=isotope ratio$_{1H/2H}$–isotope ratio$_{standard}$). In this manner the ratio of the extent of $^1$H/$^2$H exchange for residues of the free form can be normalized to the bound form (Δisotope ratio$_{free}$/Δisotope ratio$_{bound}$). These values appear in Table 13-2. A value of one indicates that exchange occurred to the same extent in the free and bound forms (Δisotope ratio$_{free}$=Δisotope ratio$_{bound}$). A value of zero indicates no exchange occurred in the free form (Δisotope ratio$_{free}$=0). A value less than zero (Δisotope ratio$_{free}$/Δisotope ratio$_{bound}$<0) is meaningless. One may argue that the negative value due to Δisotope ratio$_{bound}$<0 reflects that the residue of the peptide becomes more exposed upon binding to G$_{aq}$. Considering that this is a small peptide of 12 residues and would have most of the residues exposed, binding to the G$_{aq}$ would only protect residues from $^1$H/$^2$H exchange and not enhance it. A negative result may have some importance when considering a protein conformation shift when binding to another protein, but this scenario remains to be examined. In the trivial case, a negative value could also result when Δisotope ratio$_{free}$<0, but this difference would be due a statistical anomaly reflecting isotope ratio measurement error. Since the values in Table 6.2 are the ratio of differences, small changes in Δisotope ration$_{bound}$ could have profound effects on this ratio. Nevertheless, if exchange occurred the amount of exchange for the free peptide would be more than that for the bound peptide and thus the ratio would be greater than one. However, there is a caveat in interpreting a value greater than one. The extent of $^1$H/$^2$H exchange has been shown to be a function of hydroxyl radical generated, the concentration of DTT, and the presence of other competing substrates present in the irradiated volume, hence a method of normalizing the amount of $^1$H/$^2$H exchange into each residue is required. Experimentally, this involves the use of an internal reference.

Internal Reference. In previous examples, leucine was used as the internal reference when examining the extent of $^1$H/$^2$H exchange into CTP (SEQ ID NO: 2). In order to measure the isotope ratio of leucine, an aliquot had to be removed and then derivatized with DNS-Cl, the DNS-Leu purified, and then analyzed by direct infusion ESI-MS. To minimize sample handling the internal reference was changed to 2,4-DNP-Leu. This change enabled (1) the internal reference 2,4-DNP-Leu to be separated from cm-CTP (SEQ ID NO: 2) during reversed-phase HPLC and (2) the elution of 2,4-DNP-Leu to be monitored by PDA detection ($\epsilon_{369\ nm}$=16,000 M$^{-1}$cm$^{-1}$. The isotope ratio measurement for 2,4-DNP-Leu was performed using ESI-MS in the negative mode by direct infusion. The isotope ratios of the 2,4-DNP-Leu (standard and $^1$H/$^2$H exchange) appear in Table 13-1. The difference between the internal reference exchange sample and the standard (Δisotope ratio$_{reference}$) is used to normalize the values of Δisotope ratio$_{free}$ and isotope ratio$_{bound}$ listed in Table 13-2. The resulting value is called the "Protection Factor" and the calculated values appear in Table 13-3.

Example 14

Quantifying $^1$H/$^2$H Exchange Using Mass Spectrometry

Discussion. Measuring isotope ratios of amino acids can play a role in biochemical studies of amino acid metabolism and protein turnover, where the use of nonradioactive tracers is desired. It is also significant in mechanistic enzymology where the determination of kinetic isotope effects is a primary tool for determining the transition state structure of enzyme reactions. For these reasons, isotope ratios of amino acids have been determined by a variety of methods. Typically the compound of interest requires derivatization to a species suitable for GC-MS analysis. Although the derivatization procedures have been well developed, any sample handling always involves the potential for sample loss and the introduction of reaction byproducts that can potentially interfere with the GC-MS analyses. Two other problems are inherent to GC-MS analysis of isotope ratios: first, the ion current is never constant across a chromatographic peak and second, the chromatographic efficiency of many GC columns is great enough to effect partial resolution of the isotopologues. Consequently, the isotope ratio must be determined by integrating each ion peak separately. One advantage of high precision isotope ratio mass spectrometers is their methods of sample introduction, i.e. either a capillary leak for gases or thermal desorption for metal ions, generates a constant ion current.

Electrospray ionization of amino acids has the potential to generate a constant ion current of an amino acid sample by direct flow injection analysis. The work presented in this example demonstrates that amino acid isotope ratio measurements by ESI-MS is possible. The resolution obtained with a standard quadrupole is easily sufficient for isotope ratio measurements on 5–100 nanomole amounts of amino acids. Both direct flow injection and reversed-phase HPLC have been successfully coupled to ESI-MS and are presented. The initial efforts using GC-MS to measure amino acid isotope ratios as N-acetylpentafluorobenzyl esters using electron capture-negative chemical ionization (EC-NCI) are also described and compared to the ESI-MS methods.

Ion Current. Typically, GC-MS analyses are designed to produce very narrow and defined peaks to separate a large mixture of compounds in a relatively short time, as in the case of hydrocarbon analysis. Smaller peak widths increase the peak maximum and enhance resolution between eluting compounds but lowers the number of data points collected for each compound. In GC-MS it is desired to have the peak width become so narrow that it becomes a "spike" whose height is equivalent to the area. However, if the number of scans performed by the mass spectrometer were increased, the number of data points in the peak will be increased and this would potentially contribute to a lower error in measurement. One could keep the same profile and increase the scanning rate to increase the number of data points collected per peak, but thus approach would result in a decrease in the signal to noise ratio and contribute to the error of measurement. Thus, a method using GC-MS was developed to increase the peak width and increasing the number of scans to increase the precision in isotope ratio measurement. The peak width can be adjusted by making changes in the temperature gradient. A variety of temperature gradients were applied to both the column and injector until a satisfactory combination of gradients produced peaks widths that significantly extended the sample ion current.

Precision and Reproducibility. The precision and reproducibility of the isotope ratio measurements are shown in Table 14-2. These measurements indicate that isotope ratios can be measured with standard deviations of around 0.3% with standard errors of the mean about 0.1%. The day to day reproducibility varies on the order of 0.8%, which is not as good the between sequential sample measurements. Consistent measurements are made over a concentration range of 0.25 ng/µl to 2.0 ng/µl permitting measurements to be made on nanomole amounts of amino acid.

is less than 0.5% of the base peak. The minimal size of the $[M+H-1]^+$ is important because it reinforces the observation that the $[M+H]^+$ peak contributes minimally to the $[M+H+1]^+$ intensity and it verifies that there will be no signal from heavy isotopologues contributing to the $[M+H]^+$ peak intensity.

Precision and Reproducibility. The precision and reproducibility of the isotope ratio measurements are shown in Table 14-2. These measurements demonstrate that the isotope ratios can be easily measured with a standard deviation of less than 0.2%. The ease with which multiple determinations may be made, leads to standard errors of the mean (SEM) routinely of less than 0.1%. The day to day reproducibility is almost as good as the reproducibility between sequential samples. The measurements were shown to be independent of sample concentration within 50-fold and 5-fold concentration ranges for leucine and arginine, respectively. Isotope ratios of various concentrations of l-leucine using a new multiplier are listed in Table 14-3. The new

TABLE 14-1

Statistical Analysis of the Calculated Isotope Ratios of N-Acetyl-Leucine Determined by GC-MS Using Dissociative Electron Capture-Negative Chemical Ionization of the N-Acetyl-Leucine-Pentafluorobenzyl Ester.

| NAL-PFB Ester Concentration (ng/ml) | Number of Observations[a] | Peak Width (Number of Scans) | Mean $[M - H + 1]/[M - H]$ | SD | SEM | CV (%) |
|---|---|---|---|---|---|---|
| 0.050[b] | 7 | 676 | 0.09583 | 0.01087 | 0.00411 | 11.3 |
| 0.10[c] | 7 | 801 | 0.1016 | 0.0064 | 0.0024 | 6.3 |
| 0.25[d] | 7 | 883 | 0.08345 | 0.00436 | 0.00165 | 5.2 |
| 0.25[e] | 5 | 843 | 0.08963 | 0.00485 | 0.00217 | 5.4 |
| 0.50[d] | 7 | 747 | 0.06972 | 0.00189 | 0.00071 | 2.7 |
| 1.0[f] | 7 | 663 | 0.08748 | 0.00292 | 0.00110 | 3.3 |
| 2.0[f] | 7 | 743 | 0.08816 | 0.00196 | 0.00074 | 2.2 |

[a]The number of consecutive injections that were used to calculate the isotope ratio $[M - H + 1]^-/[M - H]^-$. The five preceding consecutive injections were not used in the calculation.
[b,c,d,e,f]denote the NAL-PFB esters analyzed on the day b, c, d, e, or f. Abbreviations: SD, standard deviation; SEM, standard error of the mean, SEM = $SD/n^{1/2}$; CV, coefficient of variation, CV = $SD/([M - H + 1]^-/[M - H]^-) \times 100$.

Figure 9:
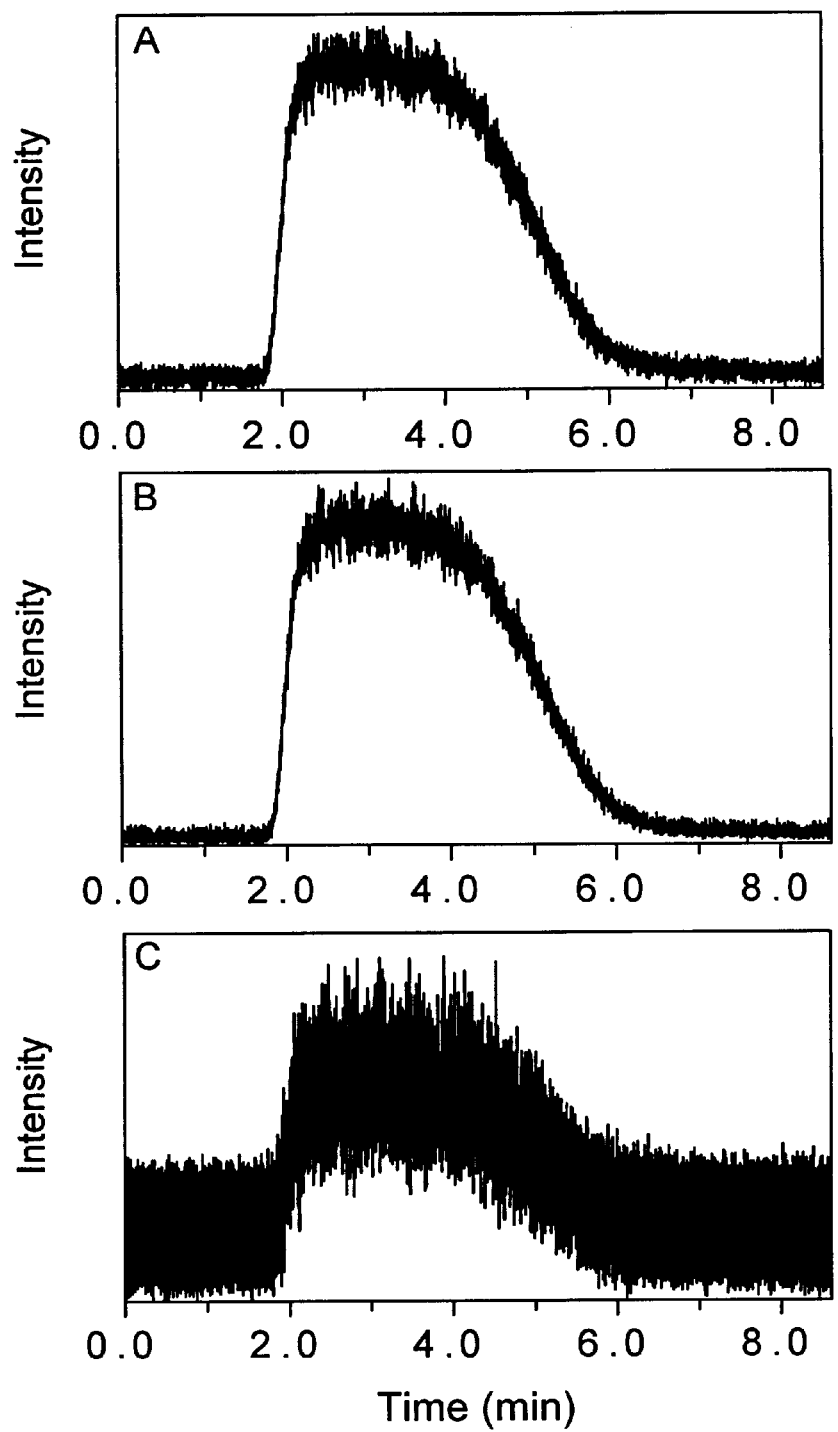
FIG. 9 is an electrospray ion chromatographs of L-Proline. The chromatographic ion profiles of (A) the total ion current, (B) the [M+H]+ ion current at 116.0 m/z, and (C) the [M+H+1]+ ion current at 117.0 m/z are presented. Data was acquired using a SIM acquisition mode. The chromatographs were obtained from the fourth injection of the 0.10 μg/μl L-proline sample listed in Table 14-1 and are representative of the chromatographic ion profiles produced by the other amino acids.

Results for ESI-MS Isotope Ratio Measurements—Constant Ion Current. Direct injection analyses with electrospray ionization can generate long term stable ion currents. This is shown for l-proline in FIG. 9. In addition to the total ion current, the currents for the $[M+H]^+$ and $[M+H+1]^+$ ions at 116.0 and 117.0 m/z, corresponding to the protonated ions for the nominal mass isotopologue of l-proline and its mono substituted isotopologue, are presented. The significant tailing is presumably due to laminar flow in the injector before the electrospray needle. From our flow system it was possible to get about 2 minutes of constant ion current from the 20 µl injection loop. If the need existed, the constant ion current regime could be increased by increasing the length and volume of the injection loop.

Figure 10:
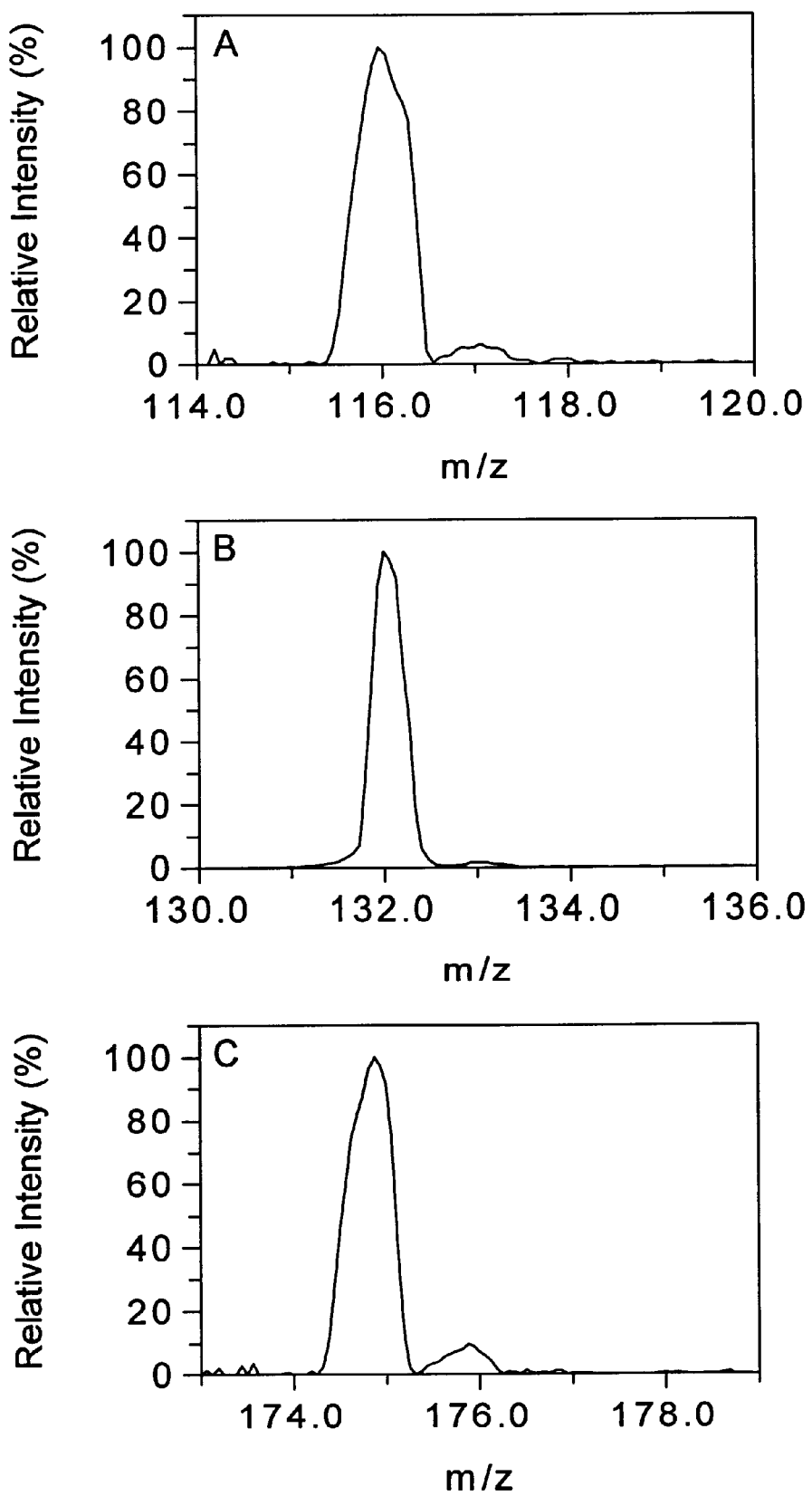
FIG. 10 is the mass spectra of L-Proline, L-Leucine, and L-Arginine. The mass spectra for (A) 100 ng/μl of L-proline, (B) 50 ng/μl of L-leucine, and (C) 50 ng/μl of L-arginine were produced using the profile acquisition mode and are corrected for background. The increased sensitivity for the L-leucine sample is the result of the installation of a new multiplier.

Mass Spectral Resolution. Resolution of the isotopic peaks is essential to the ability to measure precise isotope ratios. The profile spectra are generated as selected ion monitoring spectra with intensities measured every 1/16 Thompson. FIG. 10 shows the profile spectra acquired for l-proline, l-leucine, and l-arginine. There are two important features of these spectra: first, the $[M+H]^+$ and $[M+H+1]^+$ peaks are clearly resolved; and second, the $[M+H-1]^+$ peak multiplier enables precise isotope ratios to be determined for L-leucine samples ranging from 5.0 ng/µl (0.038 mM) to 100 ng/µl (0.76 mM). This fifty fold increase in sensitivity permits the determination of the isotope ratio of subnanomole amounts of amino acid.

Accuracy. The observed $[M+H+1]^+/[M+H]^+$ ratios for L-proline, L-leucine, and L-arginine of 0.0605, 0.0743, and 0.0849 compare to the calculated values of 0.0602, 0.0717, and 0.0833, respectively. The deviation from the calculated values may reflect the source of the L-amino acids used in this study as well as the potential for $^{13}C$ isotope effects on the electrospray process. Consequently, the accuracy of these measurements is well within that expected for an uncalibrated mass spectrometric method. Since the determination of isotope effects requires only determining a change in the ratio of $[M+H+1]^+/[M+H]^+$, the accuracy of the measurement is not as important as the precision. The accuracy of the measurement was a function of the amount of amino acid present. When excessively high concentrations of amino acid were analyzed, the isotope ratio was high. Under these conditions, the profile spectrum clearly showed that the $[M+H]^+$ peak was contributing to the $[M+H+1]^+$ peak.

TABLE 14-2

Statistical Analysis of the Calculated Isotope Ratios of Various L-Amino Acids Determined by ESI-MS

| L-Amino Acid | Concentration ($\mu g/\mu l$) | Number of Observations[a] | Mean $[M + H + 1]^+/[M + H]^+$ | SD | SEM | CV (%) |
|---|---|---|---|---|---|---|
| L-Leucine | 0.020 | 5 | 0.07647 | 0.00862 | 0.00386 | 11.3 |
|  | 0.050 | 5 | 0.07375 | 0.00556 | 0.00248 | 7.5 |
|  | 0.10[b] | 5 | 0.07331 | 0.00613 | 0.00274 | 8.3 |
|  | 0.10[c] | 6 | 0.08086 | 0.01026 | 0.00419 | 12.7 |
|  | 0.25[b] | 5 | 0.07547 | 0.00084 | 0.00038 | 1.1 |
|  | 0.25[c] | 3 | 0.07446 | 0.00331 | 0.00191 | 4.4 |
|  | 0.50 | 5 | 0.07332 | 0.00101 | 0.00045 | 1.4 |
|  | 1.0 | 5 | 0.07411 | 0.00124 | 0.00056 | 1.7 |
| L-Arginine | 0.050 | 5 | 0.08163 | 0.01069 | 0.00478 | 13.1 |
|  | 0.10[b] | 6 | 0.08634 | 0.00150 | 0.00061 | 1.7 |
|  | 0.10[c] | 4 | 0.08469 | 0.00062 | 0.00031 | 0.7 |
|  | 0.25 | 8 | 0.08369 | 0.00147 | 0.00052 | 1.8 |
| L-Proline | 0.10 | 5 | 0.06048 | 0.00080 | 0.00036 | 1.3 |

[a] is the number of observations represent consecutive 20 $\mu l$ injections.
[b,c] denote the same l-amino acid sample analyzed on different days. Abbreviations: SD, standard deviation; SEM, standard error of the mean, SEM = $SD/n^{1/2}$; CV, coefficient of variation, CV = $SD/([M + H + 1]^+/[M + H]^+) \times 100$.

TABLE 14-3

Statistical analysis of the calculated isotope ratios of various L-Leucine Samples determined by ESI-MS using a new multiplier

| L-Leucine Concentration (ng/$\mu l$) | Number of Observations[a] | Mean $[M + H + 1]^+/[M + H]^+$ | SD | SEM | CV (%) |
|---|---|---|---|---|---|
| Multiplier Voltage at 1500 volts | | | | | |
| 5.0[b,e] | 5 | 0.08427 | 0.00148 | 0.00066 | 1.8 |
| 10[e] | 7 | 0.08117 | 0.00138 | 0.00052 | 1.7 |
| 20[d] | 5 | 0.09296 | 0.00178 | 0.00080 | 1.9 |
| 50[b,d] | 5 | 0.1030 | 0.0012 | 0.0006 | 1.2 |
| $1.0 \times 10^{2[f]}$ | 5 | 0.1339 | 0.0007 | 0.0003 | 0.53 |
| Multiplier Voltage at 2000 volts | | | | | |
| 1.0[e] | 4 | 0.08518 | 0.00471 | 0.00235 | 5.5 |
| 5.0[c,e] | 5 | 0.09422 | 0.00160 | 0.00072 | 1.7 |
| 50[c,d] | 6 | 0.1235 | 0.0023 | 0.0009 | 1.8 |

[a] is the number of observations represent consecutive 20 $\mu l$ injections.
[b,c] are the same L-leucine sample analyzed on different multiplier settings on the same day.
[d,e,f] Denote the L-leucine sample analyzed on day d, e, or f. Abbreviations: SD, standard deviation; SEM, standard error of the mean, SEM = $SD/n^{1/2}$; CV, coefficient of variation, CV = $SD/([M + H + 1]^+/[M + H]^-) \times 100$.

Figure 11:
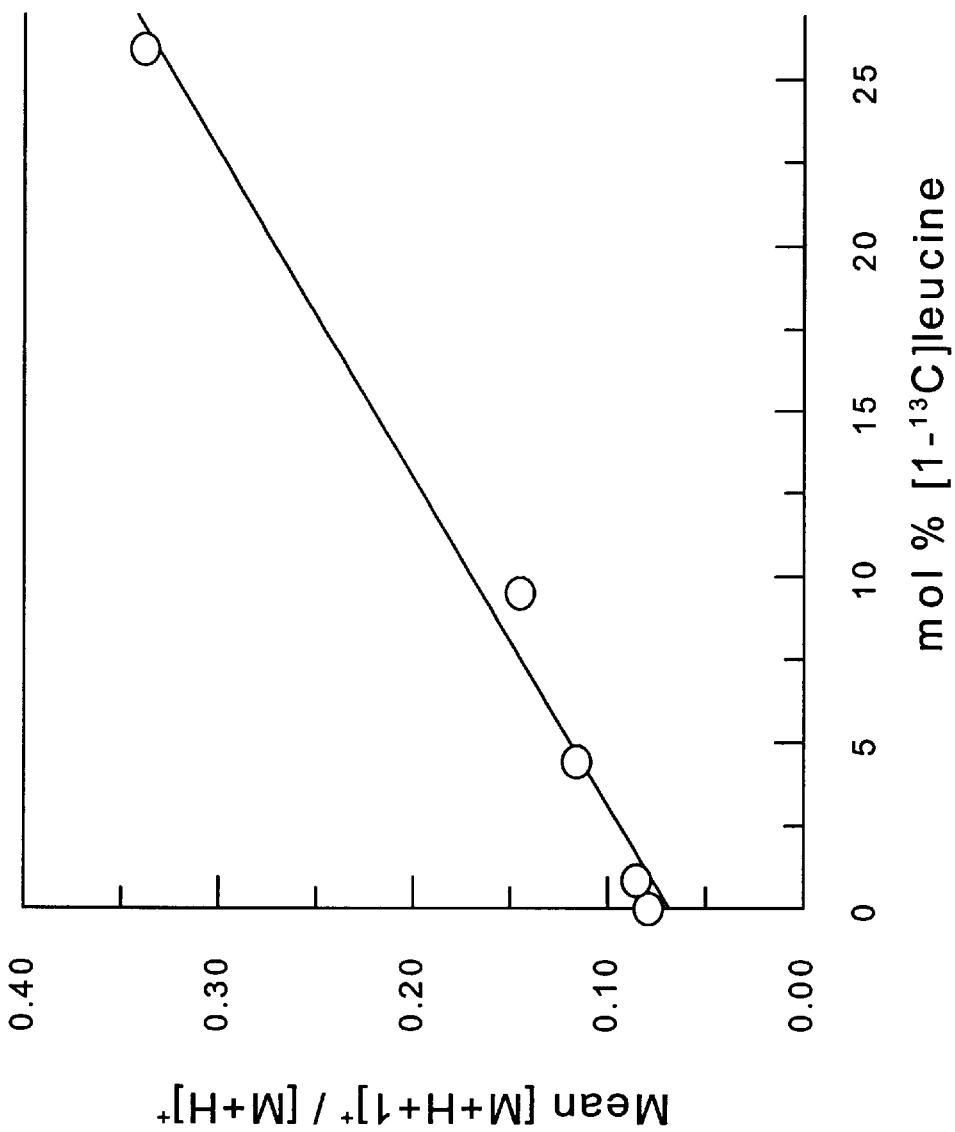
FIG. 11 is an isotope dilution curve generated by the adding varying amounts of [1-$^{13}$C]leucine as described in Example 14. The concentration of the sample used for this analysis was 25 ng/μl. The plot of mole percent [1-$^{13}$C] leucine and the measured isotope ratio ([M+H+1]+[M+H]+) was constructed and the linear regression analysis performed using GraFit Version 3.0, Erithacus Software, Ltd. The standard curve generated is y=0.0101x+0.0685 with a correlation coefficient of 0.993. Each point is the average of three (n=3) isotope ratio determinations.

Isotope Dilution. The isotope dilution curve generated by the addition of varying amounts of [1-$^{13}$C]leucine shown in FIG. 11 demonstrates that the response is linear in the range from 0 to 25%. Plotting the observed versus calculated ratios yields a line with a correlation coefficient of 0.993. Further, analysis of a sample that had 0.85 mole percent [1-$^{13}$C] leucine added was easily detected (0.0852±0.0021, Mean±SD) and calculated to contain 0.0077 indicating that atom per cent increases of less than 1% in the $[M+H+1]^+/[M+H]^+$ ratio can be easily detected and quantified.

Figure 12:
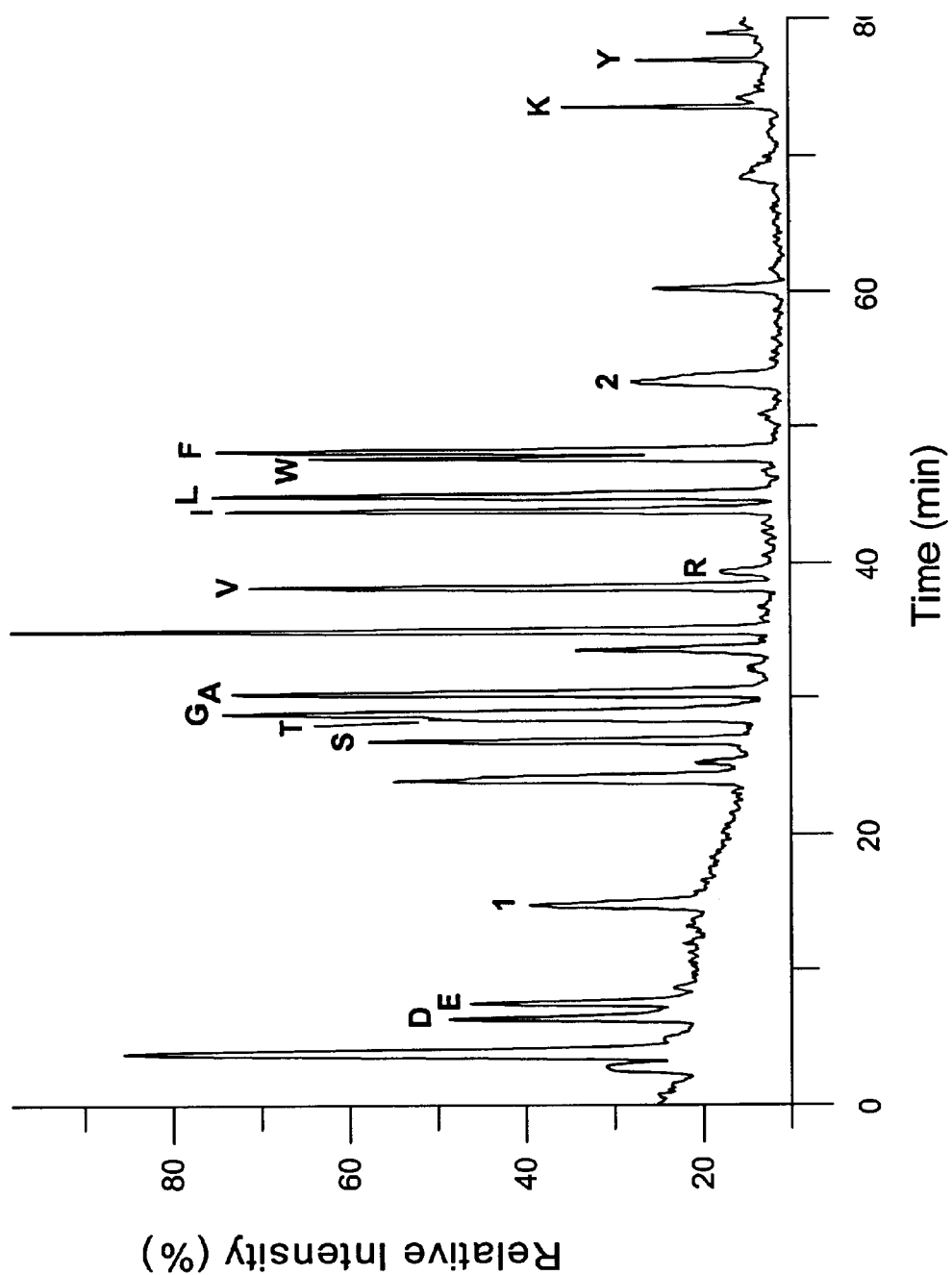
FIG. 12 is a total ion chromatograph of a mixture of DNS-Amino Acids as described in Example 14. An injection of 10 μl of 10 μM of a mixture of DNS-amino acids was made using a gradient and scanning program. The assignment of each DNS-amino acid was determined by the m/z value of the [M+H]+ ion. Peak 1 is dansyl sulfonic acid (252 m/z) and Peak 2 is the dansyl amide (251 m/z). The peak eluting before the DNS-Asp is the injection peak.
Figure 13:
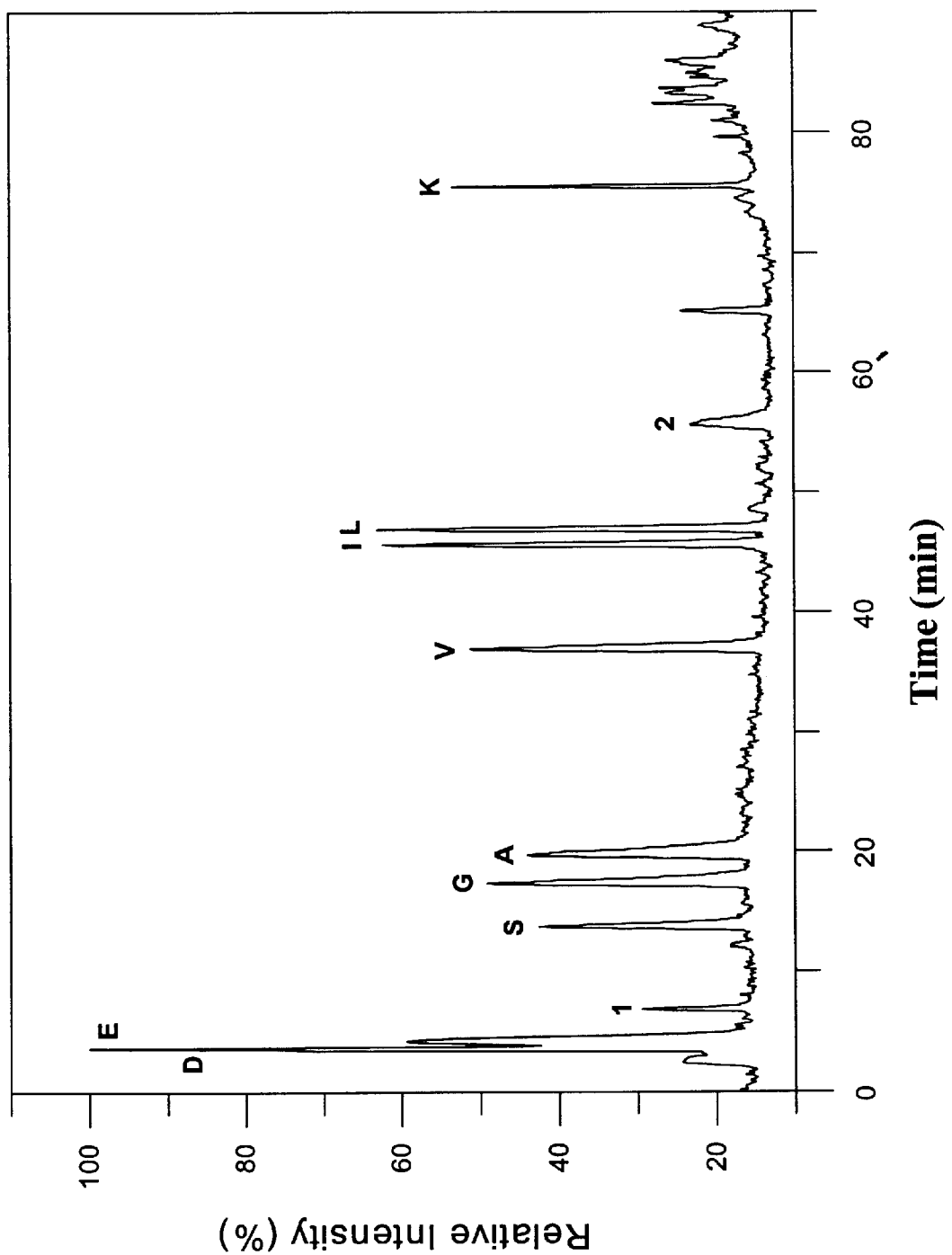
FIG. 13 is a total ion chromatograph of a mixture of DNS-amino Acids corresponding to the C-Terminal peptide (SEQ ID NO: 2) standard described in Example 14. An injection of 10 μl of 10 μM of a mixture of DNS-amino acids was made. The assignment of each DNS-amino acid was determined by the m/z value of the [M+H]+ ion. Peak 1 is dansyl sulfonic acid (252 m/z) and Peak 2 is the dansyl amide (251 m/z).
Figure 14:
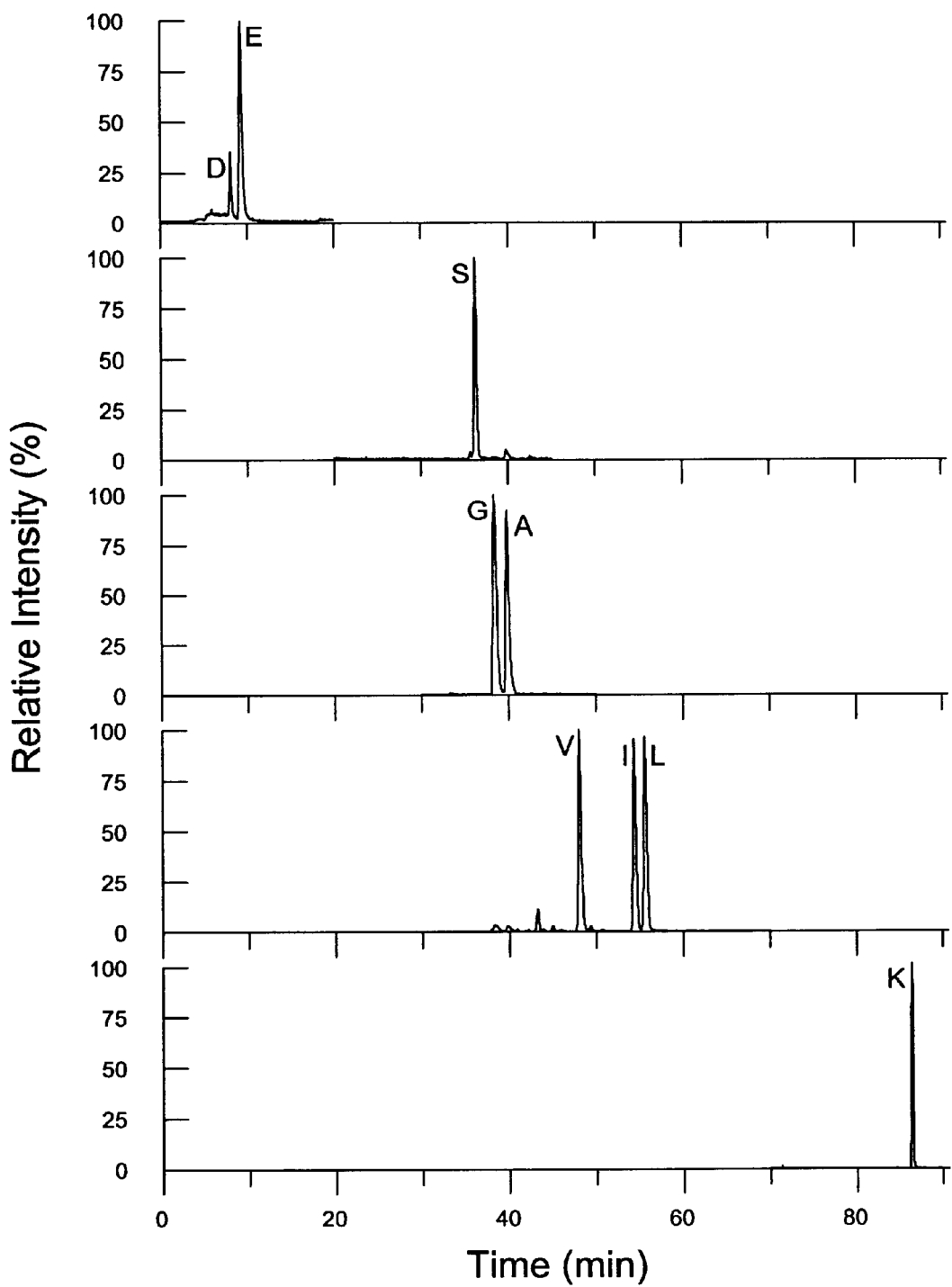
FIG. 14 is selected ion chromatographs of DNS-Amino Acids. An injection of 10 μl of 30 μM of a mixture of DNS-amino acids was made. The assignment of each DNS-amino acid was determined by the m/z value of the [M+H]+ ion. For isotope ratio measurements, each peak corresponding to the [M+H]+ ion was integrated with the appropriate background subtracted. The isotope ratio was determined by taking the ratio of the [M+H+1]+/[M+H]+ integrated areas.

Results for LC-MS Isotope Ratio Measurements. The reversed-phased HPLC method developed for LC-MS analysis was performed using a standard containing a mixture of DNS-amino acids. The total ion current (TIC) chromatograph appears in FIG. 12 with each DNS-amino acid identified by the m/z value of the $[M+H]^+$ ion. The TIC chromatograph for a mixture of DNS-amino acids corresponding to the amino acids produced by CTP (SEQ ID NO: 2) hydrolysis is shown in FIG. 13. Selected ion chromatographs generated by a typical SIM acquisition for each DNS-amino acid produced by CTP (SEQ ID NO: 2) hydrolysis is shown in FIG. 14. The precision and reproducibility of the isotope ratio measurements of a mixture of DNS-amino acids produced from C-terminal peptide hydrolysis are shown in Table 14-4.

TABLE 14-4

LC-MS determination of isotope ratios of C-Terminal peptide (SEQ ID NO: 2) residues Isotope Ratio[b]

| Residue[a] | Trial 1 | Trial 2 | Trial 3 | Mean | SD | CV |
|---|---|---|---|---|---|---|
| Ser | .182 | 0.187 | 0.179 | 0.183 | 0.004 | 2.3 |
| Asp | 0.189 | 0.195 | 0.190 | 0.192 | 0.003 | 1.7 |
| Glu | 0.200 | 0.204 | 0.203 | 0.202 | 0.002 | 1.0 |
| Lys[c] | 0.361 | 0.366 | 0.377 | 0.368 | 0.008 | 2.2 |
| Ala | 0.181 | 0.182 | 0.180 | 0.181 | 0.001 | 0.48 |
| Val | 0.204 | 0.202 | 0.204 | 0.203 | 0.001 | 0.68 |
| Leu | 0.213 | 0.210 | 0.212 | 0.212 | 0.002 | 0.90 |
| Gly | 0.169 | 0.167 | 0.170 | 0.169 | 0.001 | 0.80 |
| Ile | 0.214 | 0.211 | 0.211 | 0.212 | 0.001 | 0.69 |

[a] The isotope ratios listed are those of the corresponding dansyl derivative analyzed by LC-MS.
[b] Each trial represents a different peptide hydrolysis and LC-MS analysis performed on different days.
[c] The value for the Lys residue corresponds to the diDNS-Lys derivative.

Discussion. Three methods have been developed to measure amino acid isotope ratios: (1) GC-MS, (2) direct flow injection ESI-MS, (3) reversed-phase HPLC-ESI-MS (LC-MS).

Developing a GC-MS Method to Determine the Isotope Ratio of Amino Acids. Initially a method using GC-MS was developed to determine the isotope ratio of amino acids. The developed methodology appears in FIG. 15. The first step requires the acetylation of the amino acid, in this case, acetylating leucine to form N-acetyl-leucine (NAL). In this form GC-MS analysis is not possible. NAL needs to be chemically modified before GC-MS analysis such that (1) it can be chromatographically separated and (2) upon entering the ion volume of the MS it will ionize with minimal fragmentation. Pentafluorobenzyl esters analyzed by electron capture-negative chemical ionization (EC-NCI) in which dissociative electron capture produces the analyte of interest, accomplishes both goals. Under defined instrumental conditions this method, as compared to other available methods, is more sensitive. The higher sensitivity achievable with EC-NCI is the result of (1) virtually no background and (2) no fragmentation of the analyte. In addition, using GC-MS with selected-ion monitoring (SIM) allows for the identification of fmol to pmol amounts of material in a complex mixture. In SIM, the MS is set to monitor a number of ions during the time interval the analyte elutes from the GC capillary column, thus recording most of the ion current at the selected mass values of the analyte of interest. The analyte is then identified when the monitored ion elutes with the appropriate retention time.

Figure 15:
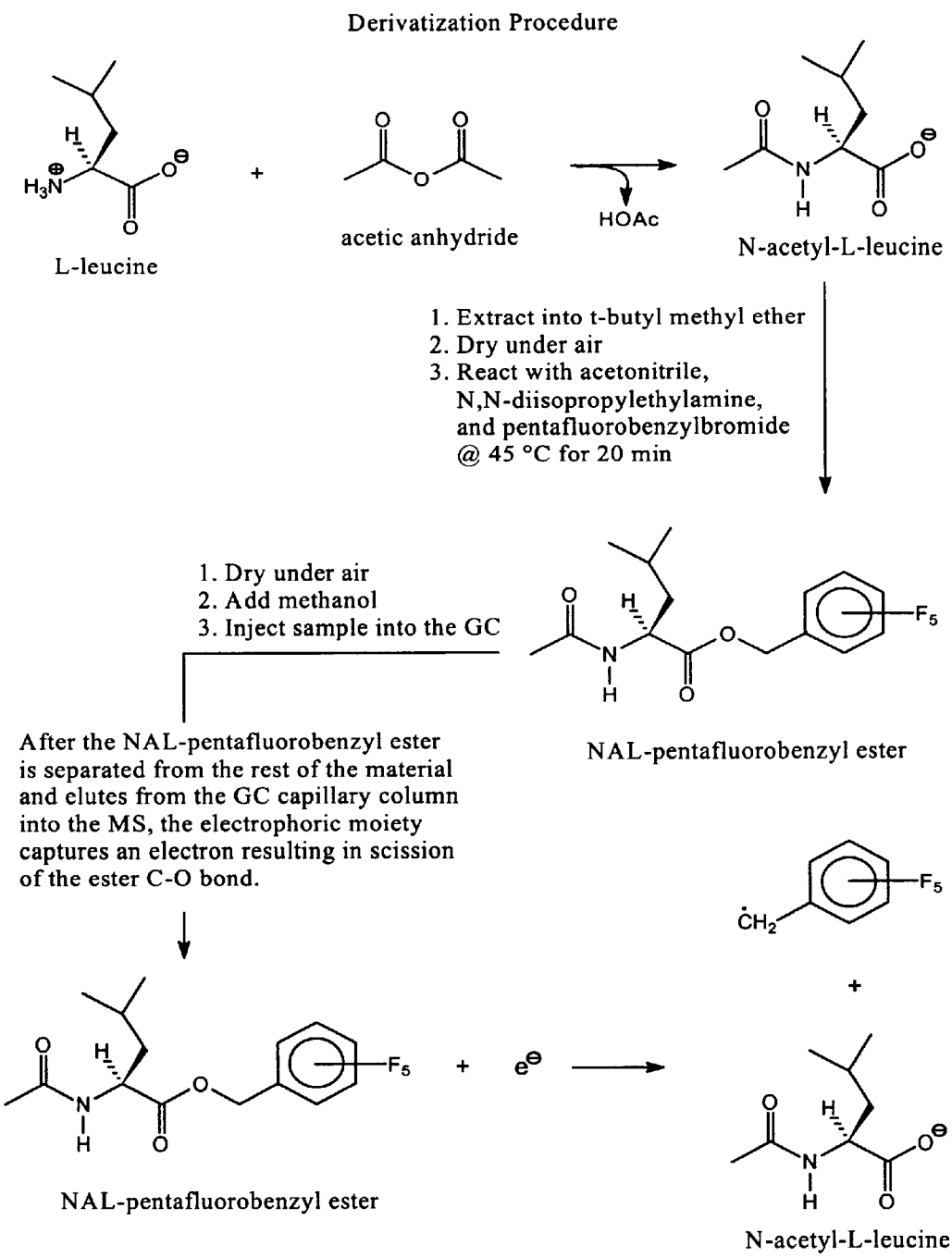
FIG. 15 is an amino acid derivatization procedure for isotope ratio measurements using GC-MS.

As shown in FIG. 15, the NAL pentafluorobenzyl ester contains a species (an electrophore) with a high electron affinity that accepts a thermalized electron with subsequent cleavage of the benzylic carbon-ester oxygen bond to produce a pentafluorobenzyl radical and the original carboxylate. The anionic NAL molecule has a mass to charge (m/z) ratio of 172 and is detected by the MS in the SIM mode. In order to detect the other naturally occurring isotopes, the MS is programmed in the selected ion monitoring mode to selectively monitor ions of the following m/z values $[M-H-1]^-$, $[M-H]^-$, $[M-H+1]^-$, $[M-H+2]^-$, and $[M-H+3]^-$. The chromatographic ion peaks (selected-ion current profiles) for $[M-H]^-$ and $[M-H+1]^-$ at the characteristic retention time (or scan numbers) are integrated, and the isotope ratio is determined by obtaining the ratio of $[M-H+1]^-/[M-H]^-$ areas.

One of skill in the art will recognize that the method described in this example can be applied to the other amino acids. However, depending on whether there are any nucleophilic functionalities contained in the side chains, derivatives other than the N-acetylated amino acid pentafluorobenzyl esters will possibly result. The ε-amino of Lys, the β-sulfhydryl of Cys, and to a lesser extent the p-hydroxyl of Tyr and the azolinium nitrogen of His will become acetylated. Incomplete acetylation of the p-hydroxyl of Tyr and the azolinium nitrogen of His may result in two pentafluorobenzyl moieties being incorporated into the derivatized amino acid. The β and γ-carboxylate oxygens of Asp and Glu, respectively, will be esterified by pentafluorobenzyl-bromide to form carboxylic ester linkages. The β-hydroxyl of Ser and Thr and the guanidinium nitrogens of Arg are poor nucleophiles and are not modified under the derivatization conditions. These possible modifications need to be kept in mind when the NCI mass spectrum is initially examined.

Developing a ESI-MS Method to Determine the Isotope Ratio of Amino Acids. A method for determining isotope ratios with high precision using ESI-MS has been demonstrated in this example. The intent of the example was to develop a method of measuring amino acid isotope ratios in order to quantify the amount of $^1H/^2H$ exchange into C—H bonds of amino acids, present either free in solution or as part of a peptide. It can also applied to biochemical studies involving amino acid metabolism and to the measurement of kinetic isotope effects on enzyme reactions.

The method described herein requires only that the amino acid be purified prior to analysis and uses electrospray ionization. The advantage of electrospray ionization is two-fold: first, it generates a constant ion current that can be prolonged as long as desired by increasing sample volume; second, there is no fragmentation of the analyte (or contaminants) that can generate background peaks that lead to gross errors in isotope ratio measurements. This is a particular advantage in the case of amino acids, where derivatization with reactive reagents, can generate byproducts that are not completely removed by GC and will then contribute to variable background signals potentially introducing large errors into the isotope ratio measurements.

Electrospray ionization has not previously been reported as an ionization method for isotope ratio measurements of simple organic compounds. The ability to detect and quantify a single $^{13}C$ or $^2H$ atom is essential to measuring isotope effects with these atoms. The results in this example clearly demonstrate that a standard quadrupole is capable of generating sufficient mass resolution for precise isotope ratios of $[M+H+1]^+/[M+H]^+$ to be determined.

Our initial studies in this example required from 40–200 nanomole of amino acid, significantly more than the detection limits of femtomole to picomole quantities routinely claimed. While this is a seemingly large amount for an electrospray-mass spectrometric method, it is an amount routinely available in the determination of kinetic isotope effects, i.e. less than one ml of one mM analyte, and is significantly less than required for most measurements made with an isotope ratio mass spectrometer. These determinations were done with an aged ion multiplier. Replacement of the ion multiplier has subsequently reduced sample requirements by 50–100 fold.

While we have reported the isotope ratio measurements on only three amino acids in this example, the relative electrospray efficiencies of 12 neutral amino acids have been reported and vary in sensitivity by less than 5-fold without optimization. We chose arginine because of the difficulties in its derivatization and because it has the potential to appear as the doubly protonated species when analyzed by electrospray ionization-mass spectrometry. In this example, arginine could be detected as the $[M+2H]^{2+}$ ion in the calibration cocktail, but not when it was present as the pure amino acid in the described solvent. Proline was selected because, as a secondary amine, it had the potential to behave differently than primary amines, and leucine was included as a typical amino acid. This isotope ratio methodology should be readily applicable to any other amino acids or other compounds that generate satisfactory $[M+H]^+$ ions. The ability to generate constant ion currents over significant times suggests that electrospray could be adapted as an ionization method for isotope ratio mass spectrometers with multiple detectors, permitting very high precision measurements to be made.

Developing a LC-MS Method to Determine the Isotope Ratio of Amino Acids/Isotope Ratio measurements using LC/MS. In this example, 0.2 M $NH_4HCO_3$ buffered solvents were used to achieve nearly baseline resolution for a mixture of 20 DNS-amino acids. In order to make use of this HPLC method for LC/MS, the buffer concentration was lowered to 1.0 mM $NH_4HCO_3$. A concentration of 2.0 mM $NH_4HCO_3$ was also tried, but the retention times were essentially identical. Lowering the buffer concentration resulted in decreased resolution for several of the DNS-amino acids, based on the total ion current (TIC) chromatograph, as expected. Changes in linear gradient profiles were made to achieve baseline resolution for nearly all DNS-amino acids, with particular attention given to DNS-Ile and DNS-Leu. The partial overlap of a few peaks, e.g. DNS-Thr and DNS-Gly, were not problematic because the masses of the eluting DNS-amino acids were separated by at least 12 u, permitting SIM data acquisition and isotope ratio measurements to be performed. This is just one of the advantages of using MS over PDA detection making LC/MS the preferred technique in many bioanalytical applications.

Currently, the LC/MS analysis time is 2 hours in column washing and equilibration time between sample injections is considered. Faster LC/MS analysis times could be achieved using steeper gradients without regard to peak resolution, which is suitable for identifying the DNS-amino acids but is unacceptable for isotope ratio determination for several reasons. First, in order to determine isotope ratios using ESI-MS it is necessary to collect enough data points to obtain an average intensity per scan that will minimize the error of measurement due to the not having enough ion current produced for a given amount of scanning time. This can occur several ways. First, the DNS-amino acid may elute too rapidly for a given MS acquisition, resulting in an insufficient number of data points. The number of data points acquired could be expanded by decreasing the dwell time of each ion used in the selected ion monitoring (SIM) acquisition, but too low a dwell time results in more noise in the spectrum that results in additional variance in the isotope ratio measurement. The second manner involves the co-elution of DNS-amino acids that require several SIM acquisitions to be run simultaneously, thus encountering the difficulties described above for faster SIM dwell times.

Our method of ESI-MS using direct flow injection to measure isotope ratios was applied to inline reversed-phase HPLC purification of DNS-amino acids. For the first injection of a given sample of DNS-amino acids, MS detection was performed using a profile acquisition (170–700 u, ⅛ u step size, 100 ms scan delay with a scan time of 2 seconds). This initial scanning acquisition was performed for two reasons. First, the elution times for each of the DNS-amino acids were identified for the given sample and reversed-phase HPLC purification conditions. Because the sample flow rate (25–30 µl/min) was obtained by a variable solvent splitting, an initial analysis of the sample was required to measure the retention times. The retention times typically varied by 1–2 min. Second, the mass of the $[M+H]^+$ ion (the predominate ionic species) of the DNS-amino acids was determined and this value was used to define the SIM acquisition. It was observed that the m/z of the $[M+H]^+$ ion varied by 0.1 u on different days.

The SIM acquisition was immediately performed after the full scan acquisition. In analyzing the internal reference 2,4-DNP-Leu (isolated during the peptide purification), the isotope ratio measurements were conducted using direct flow injection. Analysis of the DNS-amino acids of the CTP (SEQ ID NO: 2) using LC/MS required a more elaborate SIM acquisition program. Typically SIM acquisitions for the isotope ratio determinations involve monitoring five ions: $[M+H-1]^+$, $[M+H]^+$, $[M+H+1]^+$, $[M+H+2]^+$, and $[M+H+3]^+$. However, the most important ions to monitor are the $[M+H-1]^+$ ion (as an arbiter of mass resolution) and the $[M+H]^+$ and $[M+H+1]^+$ ions (for the isotope ratio determination). The data acquisition available using Mass Lynx and the Micromass Quattro II Triple Quadrupole Mass Spectrometer consists of 8 functions (time events) with each event capable of monitoring 8 ions. Thus for each function, two molecules can be monitored, each with up to four ionic species, resulting in a maximum of 16 DNS-amino acids. This means that peptides containing up to 16 different residues can be analyzed with one analysis using the LC/MS method implemented with this software. The dwell times (the period of time the quadrupole scans for each ion SIM acquisitions used in previous ESI-MS isotope ratio measurements) have either been 40 ms to 400 ms.

LC-MS vs. direct flow injection for isotope ratio measurements. There are many advantages of using LC/MS over the previous method of direct flow injection analysis (infusion) to make isotope ratio measurements. For direct infusion, each DNS-amino acid requires a separate desalting or purification step, with subsequent solvent removal by drying under $N_2$ or vacuum centrifugation. Also with infusion, the presence of background peaks (due contaminants present in the solvent and/or the sample) can lead to suppression of the analyte ion current and thus (1) prevent an accurate isotope ratio measurement or (2) require more analyte for a proper analysis. Using the LC-MS method decreases the sample handling time dramatically. The need for separate HPLC purification by UV detection and sample work up necessary to perform ESI-MS is eliminated. The LC-MS method uses inline reversed-phase HPLC coupled to ESI-MS permitting isotope ratios to be measured in a manner similar to direct infusion, obviating the need for separate DNS-amino acid isolation and ESI-MS using direct flow injection or direct infusion. By expediting the DNS-amino acid measurements, the time for residue analysis of a given peptide was reduced from approximately one week to ninety minutes.

The increase in speed afforded by the LC-MS method preserves the accuracy but reduces the precision of the isotope ratio measurement. As shown in Table 14-1 the overall precision of measuring the isotope ratio using LC-MS is around 0.3%. However, LC-MS measurements made with the aliphatic amino acids are nearly 0.1%, identical with the values obtained using direct flow injection analysis. The higher standard deviation in isotope ratio measurements using LC-MS for the DNS-Ser, DNS-Asp and DNS-Glu could be due to a lower ionization efficiency and that of diDNS-Lys being the highest due to the presence of twelve additional carbons when compared to the monodansyl derivatives. Considering that the method of alkyl $^1H/^2H$ exchange can facilitate at least a 1% deuterium incorporation into amino acid residues, the LC-MS method is capable of measuring this difference. The LC-MS method also permits isotope ratios to be measured on a smaller amounts of material than permitted by direct infusion. The direct infusion method required more material for analysis because of the separate isolation of DNS-amino acids prior to ESI-MS analysis. The lower background present in the LC-MS analysis results in a higher signal:noise ratio, thus requiring less material per analysis.

Example 15

Identification of Hydroxyl Radical Induced $^1H/^2H$ Exchange by $^2H$-NMR

Introductory Remarks. The exposure of all twenty naturally occurring amino acids to radiolytically generated hydroxyl radical under anaerobic conditions, in the presence of dithiothreitol and $D_2O$, resulted in an irreversible incorporation of $^2H$ into the side chains of these residues. This incorporation was detected and quantified by $^2H$ NMR. Integration of the observed $^2H$ resonances provides a measurement of the relative propensity towards $^1H/^2H$ exchange that is, in descending order, L>I>V>R>K>Y>P>H>F>T>A> [C, S, D, N, E, Q, G, W]. In methionine, $^1H/^2H$ exchange into both methionine and methionine sulfoxide is observed. Within the alkyl amino acids, $^1H/^2H$ exchange was detected in all of the side chain carbons, but minimal exchange into the α-carbon was observed. Integration of the $^2H$ NMR resonances within a single spectrum permitted the relative reactivity of each position to be determined. The aromatic residues incorporated $^2H$ largely into the beta methylene protons, however with tyrosine and histidine, additional $^1H/^2H$ exchange into the aromatic rings was detected. The methylene groups of the acidic residues, aspartate and glutamate, as well as the polar residues, asparagine, glutamine and serine, are deactivated towards the hydroxyl radical resulting in no $^1H/^2H$ exchange identifiable by $^2H$ NMR. Accessing the intermolecular competition of the different amino acid residues towards $^1H/^2H$ exchange in addition to characterizing and quantifying their intramolecular sites of $^2H$ incorporation will serve as markers to probe macromolecular surfaces and their interactions. There is also a potential for using $^1H/^2H$ exchange to characterize protein conformational changes. Here we report the $^2H$ NMR analysis of the exchange process that permits the location of the $^1H/^2H$ exchange within the side chains of the amino acid to be quantified and identified with atomic rather than residue resolution.

Materials. Amino acids and 2,2-dimethyl-2-silapentane-5-sulfonate (DSS) were purchased from Sigma, Aldrich and Fischer Scientific. $D_2O$ (99.9 atom % D) and $H_2O$ ($^2H$ depleted, [$^2H$]=natural abundance $10^{-2}$) were from Aldrich. Dithiothreitol (DTT) was from Boehringer Mannheim. Semiconductor Grade 4.8 nitrous oxide ($N_2O$) was from Praxair (Cleveland Ohio).

Preparation of amino acid samples for $^2H$ NMR. From 10 mM stock solutions of each of 18 of the standard amino acids in $H_2O$, 5 ml of 2.5 mM solutions were prepared in 13×100 mm test tubes and dried on a speed vacuum concentrator. Solubility constraints limited the concentrations of tyrosine and tryptophan to 2 mM. The amino acid residues were redissolved in 5 ml of 5 mM sodium phosphate buffer in $D_2O$, pD 7.2 and transferred into 12 ml glass vials sealed with Teflon lined silicone septa at room temperature. To each amino acid solution, freshly prepared aliquots of DTT dissolved in $D_2O$ were added to achieve a final concentration of 250 mM DTT in each vial. With 20 G needles connected to Teflon rubber tubing, the samples were bubbled with $N_2O$ for at least 2 hours to saturate the solution with $N_2O$ and to remove atmospheric $O_2$ through the outlet needle. To maintain a slight positive pressure of $N_2O$, a rubber bulb was inflated with $N_2O$ and secured on the cap of the vial during irradiation.

Radiolysis to effect $^1H/^2$ exchange into Amino Acids. Reductive anaerobic $^1H/^2H$ exchange was achieved by exposing the amino acids in the glass vials to gamma rays from a $^{137}Cs$ irradiator. The dose rate of 3018 Rads/min (0.5 Gy/s) and the G(OH radical) value of $5.6×10^{-7}$ mol/J for $N_2O$ saturated solutions allowed the time of exposure to be calculated using equation (15-1).

$$Time_{(min)} = \frac{[OH \text{ radical}]_{mM}}{Dosage_{rads/min} \times G(OH) \times 1.04 \times 10^{-6} \text{ mM}} \quad 15\text{-}1$$

The amino acid solutions were exposed to 500 μM OH radical after which they were removed from the irradiator and an additional 100 μM DTT was added to each vial. Further bubbling with $N_2O$ was done for 15 minutes and the reaction completed by exposure to an additional 500 μM OH radical.

Sample preparation for NMR analyses. The irradiated samples were concentrated in a speed vacuum concentrator and exchanged with $H_2O$ three to four times to remove solvent $D_2O$. In preparation for $^2H$ NMR, the residues were dissolved in 500 mL of $^2H$ depleted water and placed in 5mm NMR tubes. The concentration of the amino acids, except tyrosine and tryptophan, from 5 mL for irradiation to 0.5 ml for NMR analyses resulted in mM samples which enhanced the signal.

$^1H$ and $^2H$ NMR spectroscopy. A Varian Inova 600 MHz NMR instrument operating at 599.908 MHz (14.1 T) with a broad band probe was used to collect the $^1H$ NMR spectra. Thisequated to a resonance frequency of 92.106 MHz for $^2H$. The spectrometer's electronics were tuned for $^2H$ acquisition with the appropriate 5-point stick inserted into the probe. Prior to tuning, the lock power was turned off and a ¼ wavelength broadband preamp cable corresponding to a 60–130 MHz range attached to the wavelength jack. A sample containing an equivalent isotopic mixture of water [$^2H(50\%)$]$H_2O$ was used to obtain the shim file used for acquisition of both $^1H$ and $^2H$ spectra. The data were then acquired on the amino acid samples dissolved in $^2H$-depleted $H_2O$ with broadband proton decoupling and solvent ($D_2O$) pre-saturation. All the spectra were acquired at 25° C. with sweep widths of 6.6 and 1.5 kHz for $^1H$ and $^2H$, respectively. Processing of the $^1H$ NMR data was done referencing the chemical shift signals to the methyl groups of DSS. The acquired data were processed using Varian software on an SGI $O_2$ computer.

Figure 16:
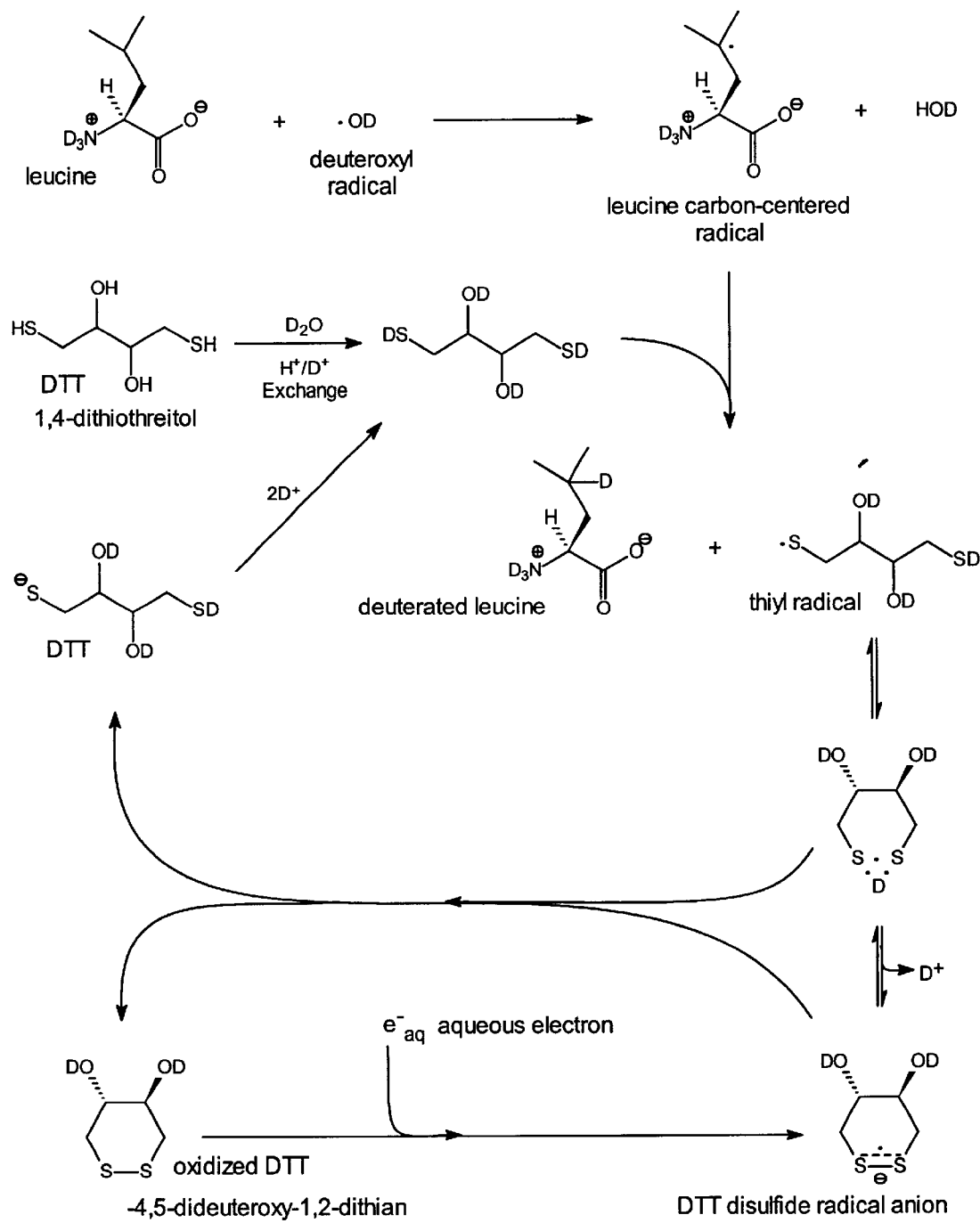
FIG. 16 is a scheme for $^1$H/$^2$H exchange into amino acids.

Isolation of site specific isotope enrichments into amino acids. The $^2H$ chemical shifts in ppm are identical to the corresponding $^1H$ chemical shifts, except for small intrinsic isotope shifts. On this premise, the chemical shifts obtained were correlated with those of the $^1H$ NMR of the corresponding standard amino acids acquired with the same instrument. Any observable scalar coupling between $^1H$ and $^2H$, $J(^1H, ^2H)$ which is known to be 6.51 times smaller than the corresponding $J(^1H, ^1H)$ coupling was eliminated by proton decoupling. The $^2H$ nucleus has a magnetic quadrupolar moment as a result of its spin quantum number of 1. The relaxation of the $^2H$ nucleus is therefore dominated by an efficient quadrupolar mechanism accounting for the complete loss of any NOE's. The $J(^2H, ^2H)$ scalar coupling are ignored since they characteristically are only 2.4% of the $J(^1H, ^1H)$ coupling. These factors simplify the resonances observed in the $^2H$ NMR spectra to singlets that are characteristic of the various sites in the amino acid side chain and whose relative integration becomes a direct measurement of relative $^2H$ enrichment. Since each amino acid was dissolved at identical concentrations and exposed to the same amount of hydroxyl radical, the integrations of each spectrum should be comparable to each other as well, which permits the intermolecular propensity for $^1H/^2H$ exchange to be assessed from the relative integrations $^2H$ NMR spectra of the different amino acids. Results and Discussion. Elucidating the sites of hydroxyl radical mediated $^1H/^2H$ exchange into the side chains of amino acids is very important for two reasons. Understanding the reactions of the hydroxyl radical with amino acids will serve in unraveling the reaction pathways of the deleterious effects of hydroxyl radical induced oxidation in biological systems. Secondly this irreversible amino acid side chain modification will serve as markers to probe solvent accessibility and interactions between peptides and proteins. The relative propensity of the different amino acids to get isotopically enriched and their mechanisms of incorporation is discussed in this section of Example 15. Shown in FIG. 16 is the a mechanism of $^1H/^2H$ exchange into amino acids. At low concentrations, DTT serves more efficiently as an alkyl radical trap by donating a $^2H$ atom, than as a hydroxyl radical scavenger. This reactivity with C-centered radicals has been shown to occur with second order rate constants of ~$10^7$ $M^{-1}s^{-1}$. The $^2H$ NMR results reported here are the first NMR characterization of the oft-invoked, thiol-mediated "repair reactions" of C-centered radicals.

DTT is preferred over other thiols because it is less prone to air oxidation, permitting dilute solutions to be prepared without a rapid loss of its reducing capability, and because the DTT thiyl radical quenches itself by forming a stable six-membered ring disulfide radical anion. The DTT disulfide radical anion disproportionates to oxidized and reduced DTT. The chemical shift assignments shown in Table 15-1 summarize the sites of enrichment of the amino acids susceptible to $^1H/^2H$ exchange.

TABLE 15-1

Assignment of observed $^2H$ NMR resonances. The amino acid order is indicative of relative incorporation into the entire amino acid. The intramolecular order also represents the relative integration of each position.

| AMINO ACID | Position | $^2H$ Resonance Assignment (ppm) |
| --- | --- | --- |
| L-leucine | methyl | δ0.90 |
| L-leucine | methine and methylene | δ1.63. |
| L-isoleucine | δ-methyl | δ0.89 |
| L-isoleucine | γ methylene | δ1.40 |
| L-isoleucine | γ methyl | δ1.20. |
| L-isoleucine | β-methine | δ1.99 |
| L-valine | diastereotopic methyls | δ0.95 |
| L-valine | methine | δ2.19. |
| L-arginine | β-methylene | δ1.85 |
| L-arginine | γ methylene | δ1.60 |
| L-arginine | δ methylene | δ3.18. |
| L-lysine | ε methyl | δ2.96 |
| L-lysine | β-methylene | δ1.85 |
| L-lysine | δ methylene | δ1.74 |
| L-lysine | γ methylene | δ1.45. |
| L-tyrosine | Phenyl $^3H$ and 5H | δ6.86 |
| L-tyrosine | β-methylene | δ3.16 |
| L-histidine | β-methylene | δ3.24 |
| L-histidine | imidazole 4H | δ7.87 |
| L-histidine | imidazole 2H | δ7.10. |
| L-proline | β-methylene | δ2.29 |
| L-proline | γ-methylene | δ1.96 |
| L-proline | δ-methylene | δ3.22. |
| L-phenylalanine | β-methylene | δ3.22. |
| L-methionine | ε-methyl | δ2.09 |
| L-methionine | γ-methylene | δ2.58 |
| Methionine sulfoxide | γ-methylene | δ3.06. |
| L-threonine | γ-methyl | δ1.28. |
| L-alanine | methyl group | δ1.42. |

The relative propensity to undergo the $^1H/^2H$ exchange reaction is indicated by being listed in descending order of enrichment. The absence of the polar amino acid residues, glycine, cysteine and tryptophan does not indicate that exchange does not occur in these residues, only that with the less sensitive $^2H$ NMR detection method that it could not be detected. We estimate the limit of detection to be between ca 0.25 mM $^2H$, which corresponds to less than 1% of the amino acid residues having incorporated $^2H$ at a given position. Because of the concentration step, the effective hydroxyl radical concentration generated was 10 mM $^1H/^2H$.

$^2H$ NMR is a unique tool to detect the sites of modification by $^1H/^2H$ exchange because the observed peaks are necessarily singlets due to negligible $^1H/^2H$ and $^2H/^2H$ coupling. The chemical shifts of $^2H$ NMR can be compared directly to those of the corresponding $^1H$ NMR making the assignments straightforward. Also, integration of the peaks gives us the relative reactivities of the different sites of incorporation and their propensities towards exchange.

The aliphatic amino acids have the greatest susceptibility to $^1H/^2H$ exchange with incorporation being effected into the side chain C-centers, illustrating separable reactivities of the primary and secondary sites. The rate constants for the reactions of the hydroxyl radical with amino acids range from $7.7 \times 10^7$ $M^{-1}s^{-1}$ at the lower end for alanine to high values like $1.3 \times 10^{10}$ $M^{-1}s^{-1}$ for tyrosine. The highly susceptible aliphatic residues to this OH radical induced exchange fall within this range. At physiological pH, the αH atoms of the amino acids are unreactive to the hydroxyl radical due to deactivation by the protonated amino group present in the zwitterionic state. This is demonstrated by the lack of $^2H$ incorporation into glycine.

Figure 20:
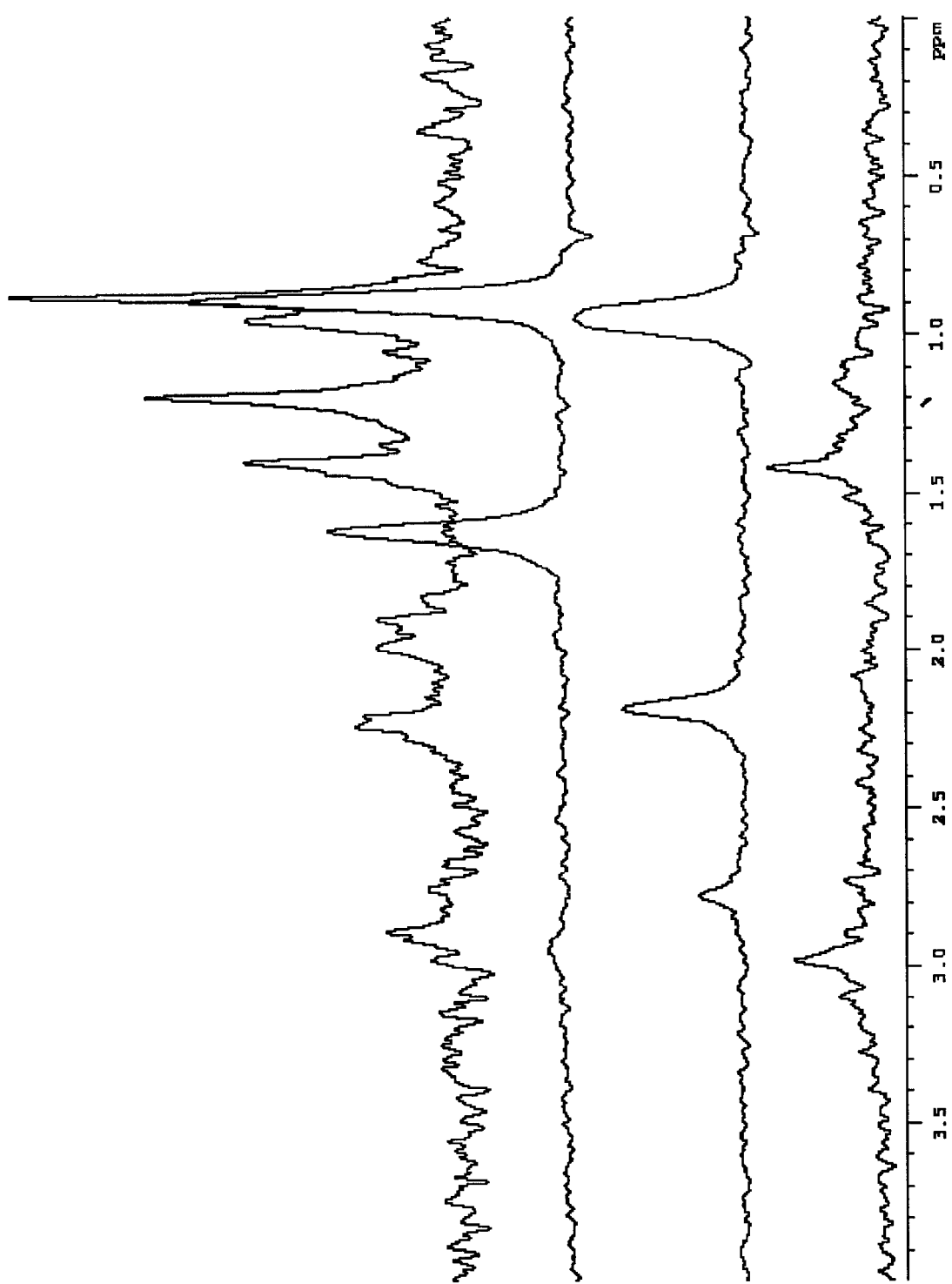
FIG. 20 is the $^2$H NMR spectra of alanine, valine, leucine and isoleucine done at 25° C. illustrating the sites of OH radical induced alkyl $^1$H/$^2$H exchange. The spectra were collected on a Varian Inova 600 MHz NMR (92 MHz resonance frequency in $^2$H) spectrometer with its electronics tuned to $^2$H. The $^2$H NMR chemical shifts were correlated with those of the $^1$H NMR of the same amino acid samples, taken, referenced to DSS. The relative ratios of incorporation determined by integration of the peaks demonstrate an increase in $^1$H/$^2$H exchange with increase in the number of side chain alkyl groups.

FIG. 20 shows $^1H/^2H$ exchange into L-alanine, L-valine, L-leucine and L-isoleucine. $^2H$ incorporation can be identified in each of the alkyl carbons the aliphatic amino acids. There is a direct relationship between the amount of $^1H/^2H$ exchange and the number of aliphatic C—H bonds. The most prominent result is that $^1H$ $^2H$ exchange was increased the greater the distance from the α-carbon. The incorporation into the methyl groups increased in the order: Ala, Val, Ile, Leu. Integration of the $^2H$ NMR peaks shows enrichment of the methyl sites to be 1.4 times greater than the methine and methylene protons of leucine. The sites of enrichment in L-isoleucine for the β-methine, γ-methylene, γ-methyl, and δ-methyl groups in the ratio 1.3:1:1:2 respectively. After normalizing to the number of protons under each peak the yields showed a 4:1:1.5:2 ratio for the four sites respectively. This implies that the β-methine protons are most prone to incorporation relative to the methylene and methyl protons. Valine also showed a 2.1 fold greater incorporation into the methyl groups when compared to the methine group. However after normalizing the yield to the number of protons under each peak we show that there is a 1.4 fold greater incorporation into the methine and methylene sites relative to the methyl sites of leucine. Similarly in valine, incorporation of $^2H$ is 2.85 times greater into the methine proton when compared to the methyl protons. One of the most important rate-determining steps of the reactions of hydroxyl radical with hydrocarbons is the abstraction of the C-centered hydrogen atoms. Using dynamical calculations, employing the variational transition state theory, the rate constants of different sites of propane were investigated, demonstrating that the H-abstraction rates of secondary sites are significantly higher than those of the primary sites. The three primary hydrogen atoms of the side chain methyl groups of these amino acids show slightly different dynamic behaviors and are not chemically equivalent in the abstraction reactions. Our results show that the amount of $^2H$ incorporated per site is a cumulative effect of the total number of H-atoms at that site. Hence our experimental observations are consistent with these theoretical findings. Knowledge of the relative stabilities and structures of radicals caused by the hydroxyl radical on amino acid residues is valuable for predicting sites of free radical-induced oxidative damage and estimation of the propagation of damage from the initiation sites. The mechanism of incorporation involves direct abstraction of a hydrogen atom to create C-centered radicals and replacement of the hydrogen atom with $^2H$ donated by DTT.

Figure 21:
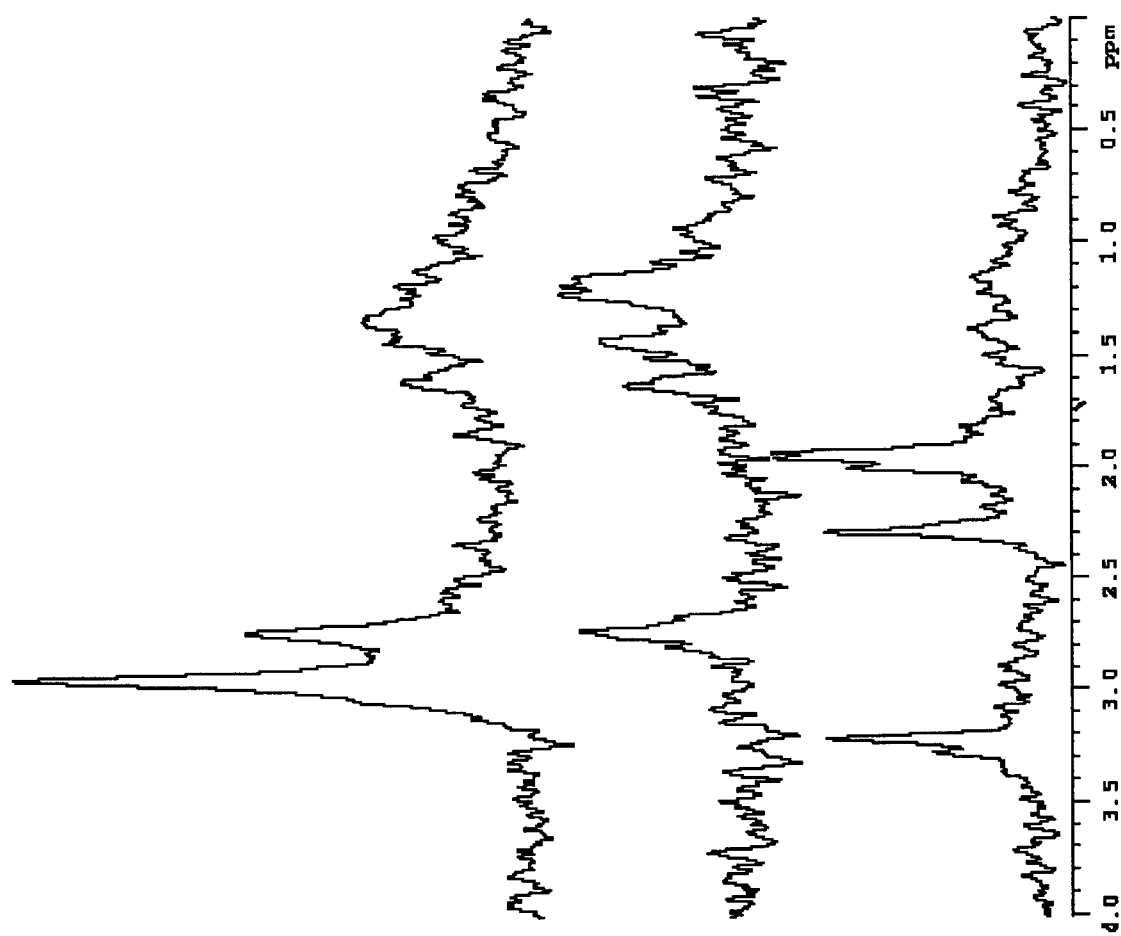
FIG. 21 is the $^2$H NMR spectra of proline, lysine and arginine done at 25° C. illustrating the sites of OH radical induced alkyl $^1$H/$^2$H exchange. The spectra were collected on a Varian Inova 600 MHz NMR (92 MHz resonance frequency in $^2$H) spectrometer with its electronics tuned to $^2$H. The $^2$H NMR chemical shifts were correlated with those of the $^1$H NMR of the same amino acid samples, taken, referenced to DSS. Incorporation into the d-methylene group of arginine and the e methylene group of lysine suggests that the side chain guanidinium ion of arginine and the ammonium ion of lysine do not deactivate these alkyl carbon centers. Similarly for proline, there was minimal deactivation towards the OH radical by the amino group on the neighboring methylene carbons. Processing of the spectra was done maintaining the same vertical scale for all three spectra.

Incorporation of $^2H$ into L-arginine, L-proline and L-lysine is shown in FIG. 21. L-arginine shows incorporation into all the methylene side chain carbons, the ratio of enrichment into the three sites, $\delta CH_2$, $\gamma CH_2$, and $\beta CH_2$ being 11:3:1. As in L-arginine, L-lysine incorporates $^2H$ into the side chain methylene C-centers, $\epsilon CH_2$, $\gamma CH_2$, $\delta CH_2$, and $\beta CH_2$ protons with a ratio of 3.3:3:1.3:1 respectively. This trend demonstrates more incorporation into the alkyl sites furthest away from the α-carbon illustrating more deactivation by the ionized amino and carboxylate groups of the α position relative to the side chain amino group. The γ protons of proline were most prone to exchange showing 2.7 fold greater incorporation than the β-protons while the δ-protons showed exchange 1.4 times greater than the β-protons.

Figure 17:
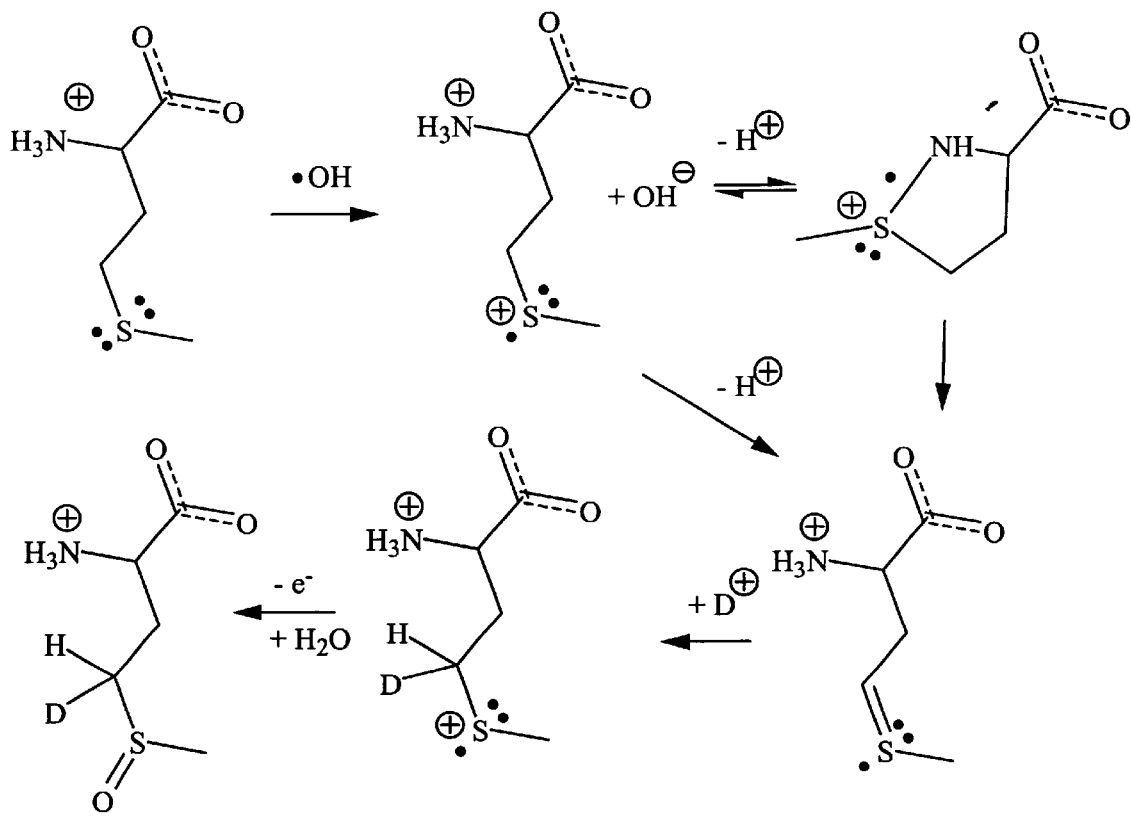
FIG. 17 is a scheme for acid base exchange from a radical intermediate.
Figure 22:
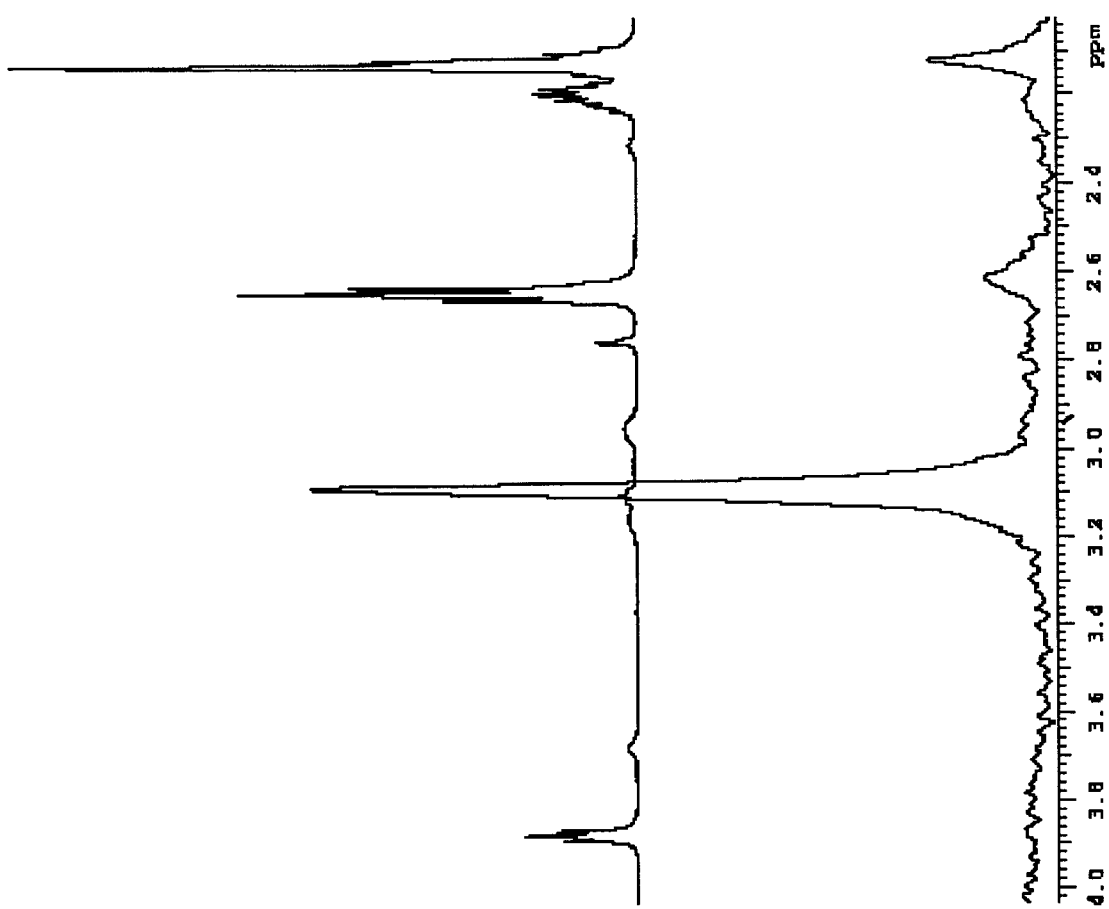
FIG. 22 is the $^1$H (top panel) and $^2$H NMR (bottom panel) spectra of methionine subjected to OH radical mediated $^1$H/$^2$H exchange. The $^2$H NMR spectrum indicates minimal incorporation into the γ-CH$_2$ and the ε-CH$_3$ groups of methionine and a larger amount of exchange into the γ-CH$_2$ group of methionine sulfoxide. The ratio of the ε-CH$_3$ group of methionine to the ε-CH$_3$ group of methionine sulfoxide (2.73 ppm) shown in the $^1$H NMR spectrum shows the absence of non-exchanged methionine sulfoxide protons.

FIG. 22 shows the results of the $^1H/^2H$ exchange into methionine. The $^1H$ NMR spectrum of the reaction following the reaction shows a trace of the γ-methylene protons of methionine sulfoxide at 3.1 ppm. In the $^2H$ NMR, this resonance attributed to methionine sulfoxide represents at least 500 μM $^2H$γ-methionine sulfoxide (or 50 μM in the irradiated solution). Because no other amino acids demonstrated signs of oxidation, the formation of this amount of methionine sulfoxide cannot be attributed to oxidation by adventitious $O_2$. The high concentration of $^2H$ in the γ-methylene of methionine sulfoxide implies that the mechanism for forming the sulfoxide involves the possibility for exchange of these methylene hydrogens. This may be as simple as an acid base exchange from a radical intermediate as shown in FIG. 17.

Figure 23:
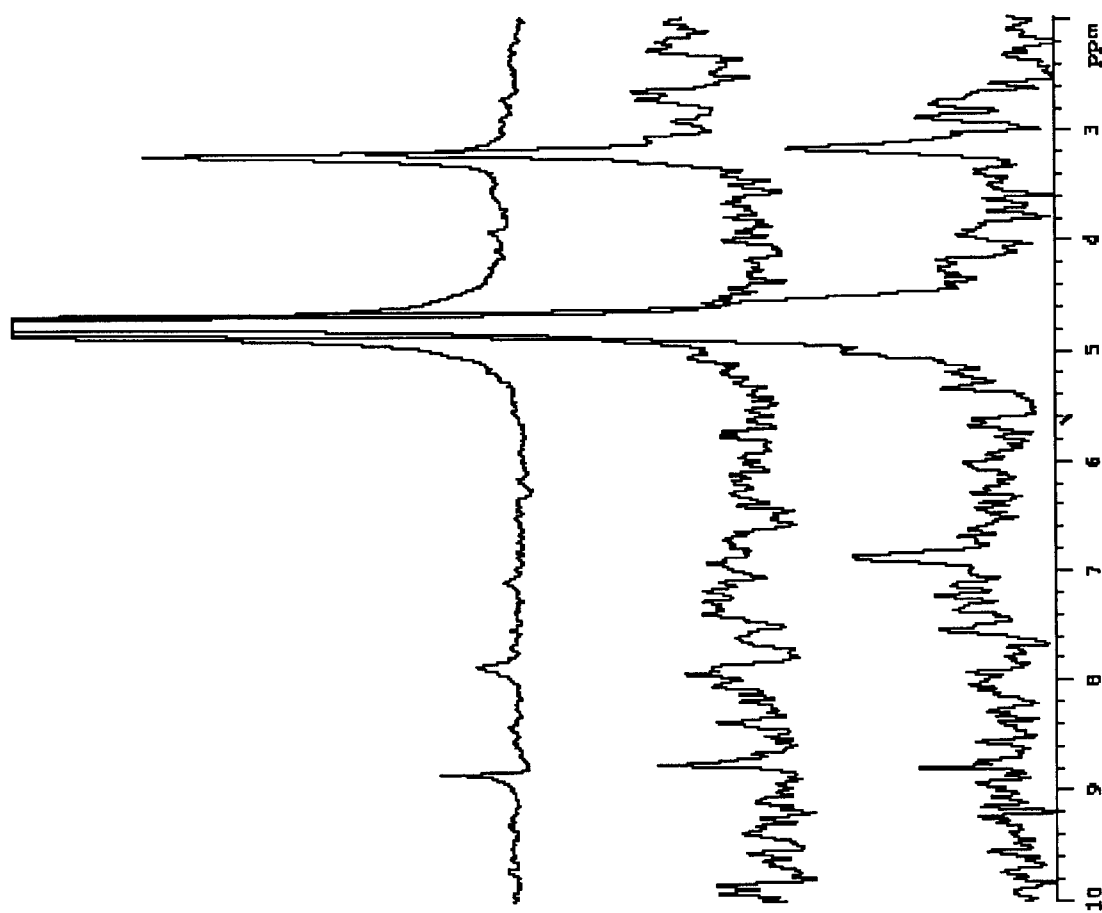
FIG. 23 is the $^2$H spectra of the aromatic amino acid residues, tyrosine, phenylalanine and histidine. The spectra were collected on a Varian Inova 600 MHz NMR (92 MHz resonance frequency in $^2$H) spectrometer with its electronics tuned to $^2$H. The $^2$H NMR chemical shifts were correlated with those of the $^1$H NMR of the same amino acid samples, taken, referenced to DSS. Exchange occurred predominantly into the β-methylene protons of all three amino acids. The low signal to noise ratio of the tyrosine spectrum is due to its low solubility at 25° C. The concentration of tyrosine used was approximately half of all the other amino acids. Incorporation into the rings of these aromatic residues is minimal except in tyrosine where $^1$H/$^2$H exchange occurs in the meta position. The peak at 8.6 ppm is a contaminant.

Methionine reacts with hydroxyl radical by H-abstraction as well, as suggested by the observation of $^2H$ incorporation into the γ- and ε-positions of methionine and a barely detectable incorporation into the β-methylene. The integration ratio of 1:1.5 ratio for γ:ε indicates that the γ-methylene and ε-methyl hydrogens are equally prone to exchange. The $^1H/^2H$ exchange into aromatic amino acids is shown in FIG. 23. The β protons of L-histidine, L-phenylalanine and L-tyrosine were the major target sites for incorporation. In histidine 81% of the total incorporation occurred in the β position, 13% in the $^2H$ position of the ring and only a trace found in the H4 position of the ring. Phenylalanine shows incorporation only into its β position while 63% of the total $^2H$ incorporated into tyrosine is found in its β position and the remaining 37% exchanges into the ortho (3,5) position of the aromatic ring.

Figure 18:
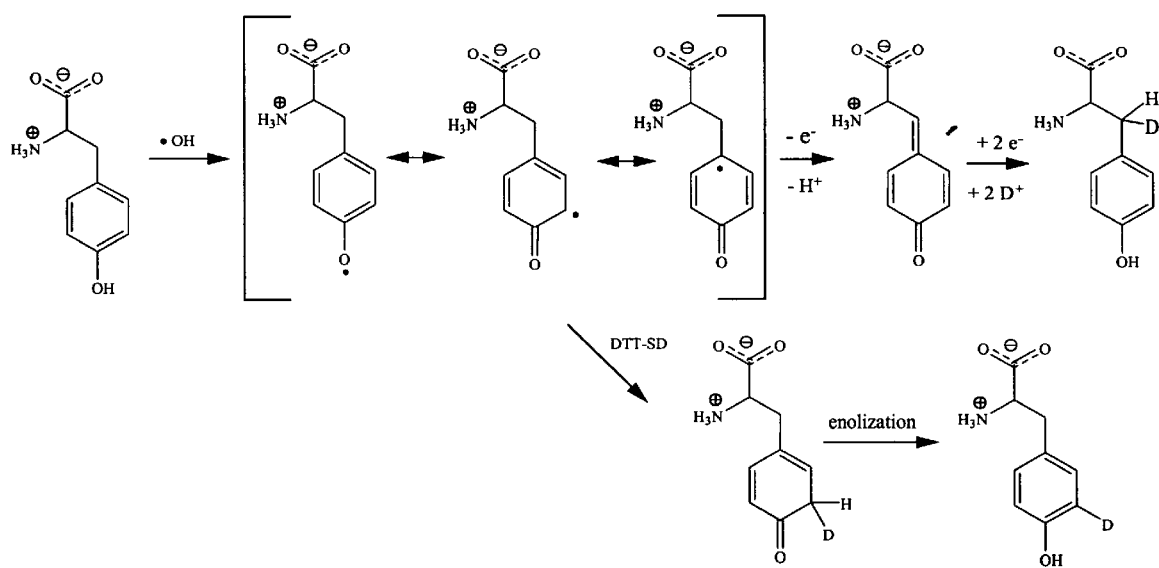
FIG. 18 is a scheme for rearomatization of the phenol ring by enolization, which results in the potential incorporation of $^2$H.

The incorporation of $^2H$ into the ortho position of the phenyl ring of tyrosine suggests abstraction of phenoxyl hydrogen tyrosine. The phenoxyl radical has significant radical character at the ortho positions, such that spin traps are incorporated at this position, and o,o-dityrosine is an identified reaction product of oxidation of tyrosine. $^2H$ atom donation to the o-position results in the formation of the keto tautomer of tyrosine. Enolization rearomatizes the phenol ring, resulting in the potential incorporation of $^2H$, as shown in FIG. 18. A primary kinetic isotope effect on enolization will preferentially retain the $^2H$ label at the o-position. The tyrosyl radical may alternatively be transiently oxidized to the quinone methide. Reduction of the quinone methide would result in $^2H$ incorporation into the β-methylene. The significantly greater $^2H$ incorporation into the tyrosine β-methylene than observed in phenylalanine is suggestive of this mechanism, although a resonance effect of the p-hydroxyl group may also be responsible for the enhanced $^1H/^2H$ exchange at the tyrosine β-methylene.

Figure 19:
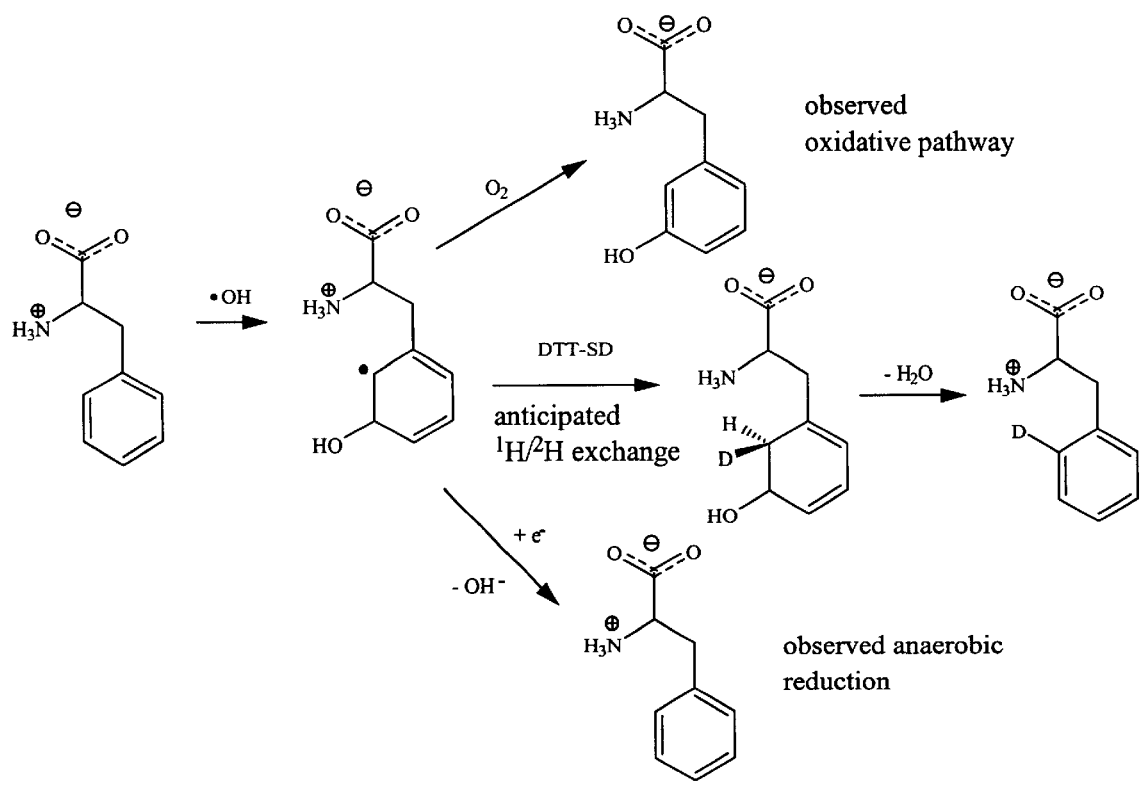
FIG. 19 is a description of the mechanism for the observed anaerobic reduction of phenylalanine.

The absence of $^1H/^2H$ exchange into phenylalanine aromatic ring was unexpected. Pulse radiolysis studies and the characterization of the aerobic reaction products of hydroxyl radical with phenylalanine both indicate that the hydroxyl radical readily adds to the aromatic ring to form a 1-hydroxy-2,4-cyclohexadienyl radical. Under aerobic conditions, the radical is oxidized, forming o-, m- and p-tyrosine. The anticipated reaction of this radical under our anaerobic reaction conditions was for DTT to trap the radical by $^2H$ atom donation. Subsequent rearomatization by dehydration would result in partial $^2H$ atom incorporation into the ring, as shown in FIG. 19. The absence of observed exchange excludes this route of reactivity. The absence of any detectable oxidized products in the $^1H$ NMR requires that the hydroxy cyclohexadienyl radical be reduced back to phenylalanine.

The absence of exchange into the α-carbon of the amino acids has been attributed to the deactivation by the protonated amine. The results of the studies in this Example suggest that the carboxylate and carboxamide are also functional groups that deactivate H atom abstraction from vicinal C—H bonds. This can be seen directly in the $^1H/^2H$ exchange into proline, where both the γ-methylene and a C—H are bonded to the amino group, but exchange is observed only into the γ-methylene. Similarly, $^1H/^2H$ exchange is observed into the ε-methylene of lysine where the ε-amino group is protonated and into the δ-methylene of arginine which is vicinal to the partially positively charged N of the guanidinium group. The deactivating character of the carboxylate and carboxamide groups is reinforced by the absence of $^1H/^2H$ exchange detected by $^2H$ NMR into Glu, Gln, Asp and Asn in these studies.

Concluding remarks. The hydroxyl radical mediated alkyl $^1H/^2H$ exchange has been studied with all twenty naturally occurring amino acids by $^2H$ NMR analysis. Our results show that $^1H/^2H$ exchange may be identified among the different kinds of amino acids with the aliphatic residues showing the most incorporation. The aliphatic residues show differential rates of exchange into the different alkyl sites. Incorporation into the methine and methylene carbons was more prominent confirming the theoretical observation that the secondary carbons are more reactive than the primary carbons. The aromatic residues show exchange prominently into their β-carbons, but that only Tyr and His have mechanisms that permit $^1H/^2H$ exchange into the ring positions. $^1H/^2H$ exchange into methionine shows formation of and incorporation into methionine sulfoxide, implicating a different mechanism of hydroxyl radical reactivity under anaerobic conditions. The $^2H$ NMR has permitted the sites of modification by $^1H/^2H$ exchange into the amino acids and quantified the relative propensities of these amino acids towards exchange. Identification of the preferred sites of H-atom abstraction permits a better assessment of the reactive surface of the amino acid in peptides and proteins.

Example 16

Hydroxyl Radical Induced $^1H/^2H$ Exchange Into the Non Aβ Component of Alzheimer's Plaques (NAC).

In this example, the use of an oxygen trapping system is disclosed. Although the oxygen trap in the example uses 10 μM pyruvate, one of skill in the art will appreciate that any useful concentration of pyruvate can be used in the oxygen trap. For example, one useful range of pyruvate is 1 to 100 μM. Furthermore, there is no requirement that pyruvate be used in the oxygen trap. In fact rather than using pyruvate, any oxidase and its associated substrate may be used. For example, glucose oxidase or protocatechuate may be used in the oxygen trap. Furthermore, although catalase is used in the oxygen trap and is desirable because it reduces the amount of hydrogen pyroxide generated, there is no absolute requirement that catalase be used in the oxygen trap.

$^1H/^2H$ exchange into NAC has been achieved under standard conditions of($D_2O$) phosphate buffer, pD 7.0, 100 μM DTT deaerated under vacuum and saturated with 1 atm semiconductor grade $N_2O$. Traces of $O_2$ are scavenged using an oxygen trap that includes 10 μM pyruvate with catalytic amounts of pyruvate oxidase and catalase. Kemptide, a hexapeptide having the sequence Arg-Arg-Ala-Ser-Leu-Gly (SEQ ID NO: 3), is included as a standard peptide. Irradiation with $^{137}Cs$ results in the $^1H/^2H$ exchange into the NAC that may be quantified by MALDI mass spectrometry. Following irradiation, the solvent exchangeable protons are removed evaporating to dryness in a Savant centrifugal evaporator, dissolving the residue in $H_2O$ and reduced to dryness. After three cycles the residue is stored until mass spectral analysis. Just prior to MALDI analysis, the residue is redissolved in $H_2O$ loaded onto a C18 Ziptip (Millipore), washed with 10 ml of $H_2O$ and eluted with ~2 µl of a saturated solution of a-cyano-4-hydroxycinnamic acid in 70% acetonitrile. The eluate is dropped directly on the MALDI target and allowed: to dry. The isotopic composition of the peptide and small protein are simultaneously determined by acquiring the MALDI spectra. Care should be taken to keep the laser intensity low enough so that the ion detector is not saturated. Saturation of the detector results in inaccurate isotope ratios. $^1H/^2H$ exchange is detected in both the kemptide and in NAC. The kemptide serves as a positive control with no solvent inaccessible residues. The NAC is a 35 residue protein, $M_r$ 3260. The extension of the $^1H/^2H$ exchange to peptides of this size demonstrates that significant $^1H/^2H$ exchange occurs prior to oxidation, aggregation or other destructive side reaction. Normalizing the amount of $^1H/^2H$ exchange observed in the kemptide to the number and type of residues allows the prediction of how much $^1H/^2H$ exchange should be observed in the NAC if all of the residues are solvent accessible. The ~10-fold lower incorporation indicates that in the NAC protein the tertiary structure protects the aliphatic carbons from exposure to hydroxyl radical.

Conclusion

The present invention is not to be limited in scope by the exemplified embodiments, which are intended as illustrations of single aspects of the invention, and any methods for the use thereof which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A method of labeling a percentage of the solvent-accessible, reduced carbon atoms in a peptide or protein with heavy hydrogen, the method comprising:
   (i) generating hydroxyl radical in a solution for a time and under conditions effective to achieve a total equivalent concentration of hydroxyl radical of at least 10 μM, wherein said solution comprises the peptide or protein, an electron scavenger source, a heavy hydrogen source, a heavy hydrogen donor, and an oxygen trapping system, wherein the oxygen trapping system optionally comprises catalase; and (ii) adding an amount of a heavy hydrogen donor to the solution to replace heavy hydrogen donor that is depleted during step (i);

wherein, when the total equivalent concentration of hydroxyl radical is achieved in step (i), the concentration of $O_2$ dissolved in the solution is sufficiently low that a substantial number of the carbon-centered radicals formed in step (i) are repaired by donation of a hydrogen isotope by the heavy hydrogen donor.

2. The method of claim 1, wherein the electron scavenger source is selected from the group consisting of solvated $N_2O$, ascorbate, tetranitromethane, nitrate, $CCl_4$, a thiol, a disulfide, a fluorinated aromatic compound, and a nitro aromatic compound.

3. The method of claim 1, wherein the heavy hydrogen source in the solution is $D_2O$ present in the solution at a molar ratio to total solution of at least 0.1 percent.

4. The method of claim 1, wherein the total equivalent concentration of hydroxyl radical is achieved by a method selected from the group consisting of exposing a light sensitive hydroperoxide in said solution to light, exposing said solution to γ-rays, exposing said solution to accelerated electrons, exposing said solution to β-radiation, exposing said solution to $^{137}Cs$ radiolysis, exposing said solution to $^{60}Co$ radiolysis, exposing said solution to $^{32}PO_4$ radiolysis, exposing said solution to Cu $K_\alpha$ radiation, exposing said solution to molybdenum $K_\alpha$ radiation, exposing said solution to synchrotron radiation, exposing said solution to neutron radiation, exposing said solution to an electronic plasma generated by a radio frequency, and exposing said solution to electronic plasma generated by high voltage.

5. A method of labeling a solvent-accessible, reduced carbon atom in a peptide or protein with deuterium, the method comprising generating a total equivalent concentration of hydroxyl radical of at least 10 μM in an aqueous $N_2O$ saturated solution that includes at least 50 picomoles of the peptide or protein, a molar ratio of $D_2O$ to total solution of at least 0.1 percent, at least 5 μM reduced dithiothreitol and an oxygen trapping system, the oxygen trapping system optionally comprising catalase, for a time and under conditions effective to label said solvent-accessible, reduced carbon atom;

wherein the hydrogen atom abstractor reacts with the solvent-accessible, reduced carbon atom in the peptide or protein to form a corresponding carbon-centered radical of the solvent-accessible, reduced carbon atom and the reduced dithiothreitol donates the deuterium to the carbon-centered radical thereby labeling the solvent-accessible, reduced carbon atom in the peptide or protein with the deuterium;

with the proviso that when the total equivalent concentration of hydroxyl radical is generated, the solution has an $O_2$ concentration of less than 6 μM.

6. The method of claim 5, wherein the total equivalent concentration of hydroxyl radical is generated by a method selected from the group consisting of exposing a light sensitive hydroperoxide in said solution to light, exposing said solution to γ-rays, exposing said solution to accelerated electrons, exposing said solution to β-radiation, exposing said solution to $^{137}Cs$ radiolysis, exposing said solution to $^{60}Co$ radiolysis, exposing said solution to $^{32}PO_4$ radiolysis, exposing said solution to Cu $K_\alpha$ radiation, exposing said solution to molybdenum $K_\alpha$ radiation, exposing said solution to synchrotron radiation, exposing said solution to neutron radiation, exposing said solution to an electronic plasma generated by a radio frequency, and exposing said solution to a plasma generated by high voltage.

7. A method of labeling a solvent-accessible, reduced carbon atom in a peptide or protein with deuterium, the method comprising:

(i) irradiating an $N_2O$ saturated aqueous solution with a $^{137}Cs$ γ-ray source for a period of time sufficient to generate a total equivalent concentration of hydroxyl radical of at least 10 μM, the solution comprising at least 50 picomoles of the peptide or protein, a molar ratio of $D_2O$ to total solution of at least 0.1 percent, at least 5 μM reduced dithiothreitol, and an oxygen trapping system, wherein the oxygen trap system optionally comprises catalase;

(ii) adding an amount of reduced, water-soluble dithiothreitol to the solution to replace reduced dithiothreitol depleted in step (i);

(iii) contacting the solution with $N_2O$ gas, having less than 3000 parts per million $O_2$, for at least five minutes; and (iv) repeating steps (i) thru (iii) until a cumulative total equivalent concentration of hydroxyl radical of 10 μM to 10 mM is achieved in the $N_2O$ saturated aqueous solution thereby labeling said solvent-accessible, reduced carbon atom.

8. A method of determining the amount of deuterium which has been incorporated into an amino acid of a peptide or protein comprising:

(a) labeling a solvent-accessible, reduced carbon atom in a peptide or protein with deuterium by generating a hydrogen atom abstractor in a solution comprising the peptide or protein, a heavy hydrogen source, a heavy hydrogen donor, and an oxygen trapping system, for a time and under conditions effective to label a solvent-accessible, reduced carbon atom on said peptide or protein, wherein the solution is substantially oxygen free when the hydrogen atom abstractor is generated and wherein said oxygen trapping system optionally comprises catalase;

(b) sequentially hydrolyzing the peptide or protein into a plurality of hydrolyzed amino acids after the hydrogen atom abstractor is generated;

(c) optionally, derivatizing the plurality of hydrolized amino acids prior to purification;

(d) purifying a sequentially hydrolyzed amino acid selected from the plurality of hydrolyzed amino acids; and (e) quantifying the amount of deuterium covalently bonded to a solvent-accessible, reduced carbon atom of the sequentially hydrolyzed amino acid.

9. A method of labeling a solvent-accessible, reduced carbon atom in a peptide or protein with a deuterium atom, the method comprising achieving a total equivalent concentration of hydroxyl radical of at least 10 μM in an aqueous $N_2O$ saturated solution comprising at least 50 picomoles of the peptide or protein, a molar ratio of $D_2O$ to total solution of at least 0.1 percent, at least 5 μM reduced dithiothreitol, and an oxygen trapping system, the oxygen trapping system optionally comprising catalase, for a time and under conditions effective to label said solvent-accessible, reduced carbon atom;

wherein hydroxyl radical reacts with the solvent-accessible, reduced carbon atom in the peptide or protein to form a corresponding carbon-centered radical of the solvent-accessible, reduced carbon atom and the reduced dithiothreitol donates the deuterium to the carbon-centered radical thereby labeling the solvent-accessible reduced carbon atom in the peptide or protein with the deuterium;

with the proviso that when the total equivalent concentration of hydroxyl radical is achieved, the aqueous $N_2O$ saturated solution has an $O_2$ concentration of less than 6 $\mu$M.

10. A method of labeling a solvent-accessible, reduced carbon atom in a peptide or protein with deuterium, the method comprising:

(i) irradiating an $N_2O$ saturated aqueous solution with a $^{137}Cs$ γ-ray source for a period of time sufficient to generate a total equivalent concentration of hydroxyl radical of at least 10 $\mu$M, the solution comprising at least 50 picomoles of the peptide or protein, a molar ratio of $D_2O$ to total solution of at least 0.1 percent, at least 5 $\mu$M reduced dithiothreitol, and an oxygen trapping system, wherein said oxygen trapping system optionally comprises catalase;

(ii) adding an amount of reduced, water-soluble dithiothreitol to the solution to replace reduced dithiothreitol depleted in step (i);

(iii) contacting the solution with $N_2O$ gas, having less than 3000 parts per million $O_2$, for at least five minutes; and (iv) repeating steps (i) thru (iii), under conditions effective to label said solvent-accessible, reduced carbon atom, until a cumulative total equivalent concentration of hydroxyl radical of 10 $\mu$M to 10 mM is generated in the $N_2O$ saturated aqueous solution.

11. A method of labeling solvent-accessible, reduced carbon atoms in a peptide or protein, the method comprising:

generating a hydrogen atom abstractor in a solution comprising the peptide or protein, a heavy hydrogen source, a heavy hydrogen donor, and an oxygen trapping system, for a time and under conditions effective to label said solvent-accessible, reduced carbon atoms; wherein:

(i) the solution is substantially oxygen free when the hydrogen atom abstractor is generated in the solution;

(ii) the heavy hydrogen donor is selected from the group consisting of a reduced water soluble thiol, $H_2S$, L-Ascorbic Acid, (±)-α-tocopherol, a phenol, a water soluble phosphine, and a water soluble phosphite;

(iii) the hydrogen atom abstractor reacts, during said generating step, with said solvent-accessible, reduced carbon atoms to form corresponding carbon-centered radicals and the heavy hydrogen donor donates a heavy hydrogen to each said corresponding carbon-centered radical; and (iv) said oxygen trapping system optionally comprises catalase;

with the proviso that when the heavy hydrogen donor is a water soluble phosphine or water soluble phosphite, the heavy hydrogen donor contains a bond selected from the group consisting of P—H, P—D, and P—T.

12. The method of claim 11, wherein the solution is made substantially oxygen free by contacting the solution with a gas, having less than 3000 parts per million $O_2$, for at least an amount of time that is sufficient to make the concentration of $O_2$ dissolved in the solution 6 $\mu$M or less.

13. The method of claim 12, wherein the gas is selected from the group consisting of $N_2O$, $N_2$, argon, helium, and anoxic mixtures thereof.

14. The method of claim 11, wherein the solution is made substantially oxygen free by contacting the solution with a $N_2O$ gas, having less than 3000 parts per million $O_2$ for a sufficient amount of time such that at least five percent of the carbon-centered radicals, which are formed by a reaction of the hydrogen atom abstractor with reduced, solvent-accessible carbon atoms in the peptide or protein, are repaired by donation of a hydrogen isotope by the heavy hydrogen donor.

15. The method of claim 11, wherein the hydrogen atom abstractor is selected from the group consisting of peroxonitrous acid, hydrogen atom, hydroperoxyl radical, alkoxyl radical, alkyl radical, singlet oxygen, metal oxo species, and hydroxyl radical.

16. The method of claim 11, wherein the hydrogen atom abstractor is hydroxyl radical, and the solution includes an electron scavenger source when the total equivalent concentration of hydroxyl radical is generated.

17. The method of claim 16, wherein the total equivalent concentration of hydroxyl radical is generated by a metal-catalyzed Fenton reaction or by radiation.

18. The method of claim 16, wherein the electron scavenger source is selected from the group consisting of solvated $N_2O$, ascorbate, tetranitromethane, nitrate, $CCl_4$, a thiol, a disulfide, a fluorinated aromatic compound, and a nitro aromatic compound.

19. The method of claim 16, wherein the total equivalent concentration of hydroxyl radical that is generated in the solution is at least 10 $\mu$M.

20. The method of claim 16, wherein the total equivalent concentration of hydroxyl radical is generated by a method selected from the group consisting of exposing a light sensitive hydroperoxide in said solution to light, exposing said solution to γ-rays, exposing said solution to accelerated electrons, exposing said solution to β-radiation, exposing said solution to $^{137}Cs$ radiolysis, exposing said solution to $^{60}Co$ radiolysis, exposing said solution to $^{32}PO_4$ radiolysis, exposing said solution to Cu $K_\alpha$ radiation, exposing said solution to molybdenum $K_\alpha$ radiation, exposing said solution to synchrotron radiation, exposing said solution to neutron radiation, exposing said solution to an electronic plasma generated by a radio frequency, and exposing said solution to an electronic plasma generated by a high voltage.

21. The method of claim 11, wherein the solution is made substantially oxygen free by bubbling the solution with argon for five minutes or longer, and then bubbling the solution with $N_2O$ gas, having less than 500 parts per million $O_2$, until a concentration of $O_2$ dissolved in the solution when the hydrogen atom abstractor is generated is sufficiently low that a substantial number of the corresponding carbon-centered radicals, formed by the reaction of the hydrogen atom abstractor with solvent-accessible, reduced carbon atoms in the peptide or protein, are repaired by donation of a hydrogen isotope by the heavy hydrogen donor.

22. The method of claim 11, wherein the heavy hydrogen source in the solution is $D_2O$ present in the solution at a molar ratio to total solution of at least 0.1 percent.

23. The method of claim 11, wherein the solvent-accessible, reduced carbon atom is in a side chain of a residue on the peptide or protein.

24. The method of claim 1, wherein the total equivalent concentration of hydroxyl radical is generated by a metal-catalyzed Fenton reaction or by radiation.

25. The method of claim 5 wherein the total equivalent concentration of hydroxyl radical is generated by a metal-catalyzed Fenton reaction or by radiation.

26. A method of labeling a solvent-accessible, reduced carbon atoms in a peptide or protein with deuterium, the method comprising:
generating a hydrogen atom abstractor in a substantially oxygen free solution comprising the peptide or protein, a deuterium source, a heavy hydrogen donor, and an oxygen trapping system, for a time and under conditions effective to label said solvent-accessible, reduced carbon atoms to form corresponding carbon-centered radicals and the heavy hydrogen donor donating a deuterium to each said corresponding carbon-centered radical, wherein said oxygen trapping system optionally comprises catalase.

27. The method of claim 26, wherein the solution is made substantially oxygen, free by contacting the solution with a gas, having less than 3000 parts per million $O_2$, for at least an amount of time that is sufficient to make the concentration of $O_2$ dissolved in the solution 6 $\mu$M or less.

28. The method of claim 27, wherein the gas is selected from the group consisting of $N_2O$, $N_2$, argon, helium, and anoxic mixtures thereof.

29. The method of claim 26, wherein the solution is made substantially oxygen free by contacting the solution with a $N_2O$ gas, having less than 3000 parts per million $O_2$, for a sufficient amount of time such that a substantial number of the carbon-centered radicals, which are formed by a reaction of the hydrogen atom abstractor with reduced solvent-accessible, reduced carbon atoms in the peptide or protein, are repaired by donation of a hydrogen isotope by the heavy hydrogen donor.

30. The method of claim 26, wherein the hydrogen atom abstractor is selected from the group consisting of peroxonitrous acid, hydrogen atom, hydroperoxyl radical, alkoxyl radical, alkyl radical, singlet oxygen, metal oxo species, and hydroxyl radical.

31. The method of 26, wherein the hydrogen atom abstractor is hydroxyl radical, and the solution includes an electron scavenger source when the total equivalent concentration of hydroxyl radical is generated.

32. The method of claim 31, wherein the total equivalent concentration of hydroxyl radical is generated by a metal-catalyzed Fenton reaction or by radiation.

33. The method of claim 31, wherein the electron scavenger source is selected from the group consisting of solvated $N_2O$, ascorbate, tetranitromethane, nitrate, $CCl_4$, a thiol, a disulfide, a fluorinated aromatic compound, and a nitro aromatic compound.

34. The method of claim 31, wherein the electron scavenger source is solvated $N_2O$ derived from $N_2O$ gas bubbled into the solution prior to the generation of the total equivalent concentration of hydroxyl radical.

35. The method of claim 31, wherein the total equivalent concentration of hydroxyl radical is generated by a method selected from the group consisting of exposing a light sensitive hydroperoxide in said solution to light, exposing said solution to γ-rays, exposing said solution to accelerated electrons, exposing said solution to β-radiation, exposing said solution to $^{137}Cs$ radiolysis, exposing said solution to $^{60}Co$ radiolysis, exposing said solution to $^{32}PO_4$ radiolysis, exposing said solution to Cu $K_\alpha$ radiation, exposing said solution to molybdenum $K_\alpha$ radiation, exposing said solution to synchrotron radiation, exposing said solution to neutron radiation, exposing said solution to an electronic plasma generated by a radio frequency, and exposing said solution to an electronic plasma generated by a high voltage.

36. The method of claim 26, wherein the solution is made substantially oxygen free by bubbling the solution with argon for five minutes or longer, and then bubbling the solution with $N_2O$ gas, having less than 500 parts per million $O_2$, until a concentration of $O_2$ dissolved in the solution when the hydrogen atom abstractor is generated is sufficiently low that a substantial number of the corresponding carbon-centered radicals, formed by the reaction of the hydrogen atom abstractor with solvent-accessible, reduced carbon atoms in the peptide or protein, are repaired by donation of a hydrogen isotope by the heavy hydrogen donor.

37. A method of labeling a solvent-accessible, reduced carbon atom in a peptide or protein, the method comprising:
generating a hydrogen atom abstractor in a substantially oxygen free solution comprising the peptide or protein, a heavy hydrogen source, a heavy hydrogen donor, an electron scavenger source, and an oxygen trapping system, for a time and under conditions effective to label said solvent-accessible, reduced carbon atom, the hydrogen atom abstractor reacting with said solvent-accessible, reduced carbon atom to form the corresponding carbon-centered radical with the heavy hydrogen donor donating a heavy hydrogen to said corresponding carbon-centered radical, wherein said oxygen trapping system optionally comprises catalase.

38. The method of claim 37, wherein the hydrogen atom abstractor is selected from the group consisting of peroxonitrous acid, hydrogen atom, hydroperoxyl radical, alkoxyl radical, alkyl radical, singlet oxygen, metal oxo species, and hydroxyl radical.

39. The method of claim 37, wherein the total equivalent concentration of hydroxyl radical is generated by a metal-catalyzed Fenton reaction or by radiation.

40. The method of claim 1, wherein said oxygen trapping system comprises an oxidase and a substrate of said oxidase.

41. The method of claim 40, wherein said oxidase is pyruvate oxidase, glucose oxidase or protocatechuate.

42. The method of claim 40, wherein said oxidase is pyruvate oxidase and said substrate is pyruvate.

43. The method of claim 5, wherein said oxygen trapping system comprises an oxidase and a substrate of said oxidase.

44. The method of claim 43, wherein said oxidase is pyruvate oxidase, glucose oxidase or protocatechuate.

45. The method of claim 43, wherein said oxidase is pyruvate oxidase and said substrate is pyruvate.

46. The method of claim 7, wherein said oxygen trapping system comprises an oxidase and a substrate of said oxidase.

47. The method of claim 46, wherein said oxidase is pyruvate oxidase, glucose oxidase or protocatechuate.

48. The method of claim 46, wherein said oxidase is pyruvate oxidase and said substrate is pyruvate.

49. The method of claim 8, wherein said oxygen trapping system comprises an oxidase and a substrate of said oxidase.

50. The method of claim 49, wherein said oxidase is pyruvate oxidase, glucose oxidase or protocatechuate.

51. The method of claim 49, wherein said oxidase is pyruvate oxidase and said substrate is pyruvate.

52. The method of claim 9, wherein said oxygen trapping system comprises an oxidase and a substrate of said oxidase.

53. The method of claim 52, wherein said oxidase is pyruvate oxidase, glucose oxidase or protocatechuate.

54. The method of claim 52, wherein said oxidase is pyruvate oxidase and said substrate is pyruvate.

55. The method of claim 10, wherein said oxygen trapping system comprises an oxidase and a substrate of said oxidase.

56. The method of claim 55, wherein said oxidase is pyruvate oxidase, glucose oxidase or protocatechuate.

57. The method of claim 55, wherein said oxidase is pyruvate oxidase and said substrate is pyruvate.

58. The method of claim 11, wherein said oxygen trapping system comprises an oxidase and a substrate of said oxidase.

59. The method of claim 58, wherein said oxidase is pyruvate oxidase, glucose oxidase or protocatechuate.

60. The method of claim 58, wherein said oxidase is pyruvate oxidase and said substrate is pyruvate.

61. The method of claim 26, wherein said oxygen trapping system comprises an oxidase and a substrate of said oxidase.

62. The method of claim 61, wherein said oxidase is pyruvate oxidase, glucose oxidase or protocatechuate.

63. The method of claim 61, wherein said oxidase is pyruvate oxidase and said substrate is pyruvate.

64. The method of claim 37, wherein said oxygen trapping system comprises an oxidase and a substrate of said oxidase.

65. The method of claim 64, wherein said oxidase is pyruvate oxidase, glucose oxidase or protocatechuate.

66. The method of claim 64, wherein said oxidase is pyruvate oxidase and said substrate is pyruvate.

67. A method of labeling a percentage of the solvent-accessible, reduced carbon atoms in a peptide or protein with heavy hydrogen, the method comprising:

(i) generating hydroxyl radical in a solution for a time and under conditions effective to achieve a total equivalent concentration of hydroxyl radical of at least 10 $\mu$M, wherein said solution comprises the peptide or protein, an electron scavenger source, a heavy hydrogen source, a heavy hydrogen donor, and an oxygen trapping system, wherein the oxygen trapping system optionally comprises catalase; and (ii) adding an amount of a heavy hydrogen donor to the solution to replace heavy hydrogen donor that is depleted during step (i); and (iii) optionally repeating steps (i) and (ii) until a cumulative total equivalent concentration of hydroxyl radical generated in the solution is sufficient to produce carbon-centered radicals of said percentage of solvent-accessible, reduced carbon atoms in said peptide or protein;

wherein, when the total equivalent concentration of hydroxyl radical is achieved in step (i), the concentration of $O_2$ dissolved in the solution is sufficiently low that a substantial number of the carbon-centered radicals formed in step (i) are repaired by donation of a hydrogen isotope by the heavy hydrogen donor.

* * * * *